(12) United States Patent
Gerg et al.

(10) Patent No.: US 10,982,007 B2
(45) Date of Patent: *Apr. 20, 2021

(54) DETECTION OF A POSTTRANSLATIONALLY MODIFIED POLYPEPTIDE BY A BIVALENT BINDING AGENT

(71) Applicant: Roche Diagnostics Operations, Inc., Indianapolis, IN (US)

(72) Inventors: Michael Gerg, Munich (DE); Dieter Heindl, Paehl (DE); Christian Klein, Bonstetten (CH); Alfred Mertens, Schriesheim (DE); Volker Schmid, Penzberg (DE); Michael Schraeml, Penzberg (DE); Monika Soukupova, Wessobrunn (DE); Michael Tacke, Munich (DE)

(73) Assignee: Roche Diagnostics Operations, Inc., Indianpolis, IN (US)

( * ) Notice: Subject to any disclaimer, the term of this patent is extended or adjusted under 35 U.S.C. 154(b) by 163 days.

This patent is subject to a terminal disclaimer.

(21) Appl. No.: 15/465,439

(22) Filed: Mar. 21, 2017

(65) Prior Publication Data

US 2017/0275381 A1  Sep. 28, 2017

Related U.S. Application Data

(63) Continuation of application No. 13/923,618, filed on Jun. 21, 2013, now abandoned, which is a continuation of application No. PCT/EP2011/073560, filed on Dec. 21, 2011.

(30) Foreign Application Priority Data

Dec. 23, 2010 (EP) .................................... 10196687
Jul. 13, 2011 (EP) .................................... 11173832

(51) Int. Cl.
*C07K 16/46* (2006.01)
*G01N 33/531* (2006.01)

(52) U.S. Cl.
CPC ......... *C07K 16/468* (2013.01); *G01N 33/531* (2013.01)

(58) Field of Classification Search
None
See application file for complete search history.

(56) References Cited

U.S. PATENT DOCUMENTS

| | | |
|---|---|---|
| 4,948,882 A | 8/1990 | Ruth |
| 5,451,463 A | 9/1995 | Nelson et al. |
| 5,519,142 A | 5/1996 | Hoess et al. |
| 5,541,313 A | 7/1996 | Ruth |
| 5,571,894 A | 11/1996 | Wels et al. |
| 5,585,481 A | 12/1996 | Arnold, Jr. et al. |
| 5,587,458 A | 12/1996 | King et al. |
| 5,635,602 A | 6/1997 | Cantor et al. |
| 5,817,786 A | 10/1998 | Ruth |
| 5,849,879 A | 12/1998 | Nguyen et al. |
| 5,885,793 A | 3/1999 | Griffiths et al. |
| 5,932,448 A | 8/1999 | Tso et al. |
| 6,153,190 A | 11/2000 | Young et al. |
| 6,248,516 B1 | 6/2001 | Winter et al. |
| 6,531,581 B1 | 3/2003 | Nardone et al. |
| 6,569,619 B1 | 5/2003 | Sivaraja |
| 2003/0219827 A1 | 11/2003 | Comb et al. |
| 2004/0224372 A1 | 11/2004 | Li et al. |
| 2005/0214833 A1 | 9/2005 | Carter et al. |
| 2006/0199207 A1 | 9/2006 | Mitysiak |
| 2008/0044834 A1 | 2/2008 | Heyduk |
| 2008/0075712 A1 | 3/2008 | Hattori et al. |
| 2008/0131883 A1 | 6/2008 | Adams et al. |
| 2008/0280778 A1 | 11/2008 | Urdea |
| 2008/0312103 A1 | 12/2008 | Nemoto et al. |
| 2009/0137782 A1 | 5/2009 | Old et al. |
| 2010/0021943 A1 | 1/2010 | An et al. |
| 2010/0026617 A1 | 2/2010 | Su et al. |
| 2010/0062436 A1 | 3/2010 | Jarosch et al. |
| 2010/0081792 A1 | 4/2010 | Grant et al. |
| 2010/0266617 A1 | 10/2010 | Carven et al. |

FOREIGN PATENT DOCUMENTS

| | | |
|---|---|---|
| EP | 0061888 B1 | 10/1982 |
| EP | 0292128 A1 | 11/1988 |
| EP | 0313219 B1 | 4/1989 |
| EP | 0423839 B1 | 4/1991 |
| EP | 0523978 B1 | 1/1993 |

(Continued)

OTHER PUBLICATIONS

Mack et al., Dependence of Avidity on Linker Length for a Bivalent Ligand Bivalent Receptor Model System, |J. Am. Chem. Soc. 2012, 134, 333-345 (Year: 2012).*
Edwards et al., The Remarkable Flexibility of the Human Antibody Repertoire; Isolation of Over One Thousand Different Antibodies to a Single Protein, BLyS; J. Mol. Biol., 2003, vol. 334, pp. 103-118.
Lloyd et al., Modelling the human immune response: performance of a 10" human antibody repertoire against a broad panel of therapeutically relevant antigens; Protein Engineering, Design & Selection, 2009, vol. 22, No. 3, pp. 159-168.

(Continued)

*Primary Examiner* — Andrea S Grossman
(74) *Attorney, Agent, or Firm* — Stinson LLP

(57) ABSTRACT

A bivalent binding agent having a first monovalent binder that binds to a polypeptide epitope of a target polypeptide, a second monovalent binder that binds to a posttranslational polypeptide modification on the target polypeptide and a linker. Further disclosed are methods for the detection of a posttranslationally modified target polypeptide, for making the disclosed bivalent binding agent, and for use of the disclosed bivalent binding agent in histological staining procedures.

3 Claims, 26 Drawing Sheets

Specification includes a Sequence Listing.

(56) References Cited

FOREIGN PATENT DOCUMENTS

| | | |
|---|---|---|
| EP | 0618192 B1 | 10/1994 |
| EP | 0786468 B1 | 7/1997 |
| EP | 1074563 A1 | 2/2001 |
| EP | 1184665 A1 | 3/2002 |
| EP | 1186613 | 3/2002 |
| EP | 1431298 B1 | 3/2002 |
| EP | 1538221 B1 | 6/2005 |
| WO | 8902439 A1 | 3/1989 |
| WO | 8902931 A1 | 4/1989 |
| WO | 8912642 A1 | 12/1989 |
| WO | 9008156 A1 | 7/1990 |
| WO | 9201047 A1 | 1/1992 |
| WO | 9211388 A1 | 7/1992 |
| WO | 9215682 A1 | 9/1992 |
| WO | 9305060 A1 | 3/1993 |
| WO | 9316185 A1 | 8/1993 |
| WO | 9404550 A1 | 3/1994 |
| WO | 9410308 A1 | 5/1994 |
| WO | 9505399 A1 | 2/1995 |
| WO | 9705156 A1 | 2/1997 |
| WO | 9743451 A1 | 11/1997 |
| WO | 9906587 A1 | 2/1999 |
| WO | 00067744 A1 | 2/2000 |
| WO | 0142505 A3 | 6/2001 |
| WO | 0218643 A2 | 3/2002 |
| WO | 2003002609 A2 | 1/2003 |
| WO | 03019145 A3 | 3/2003 |
| WO | 03104249 A3 | 12/2003 |
| WO | 2004081051 A1 | 9/2004 |
| WO | 2005035753 A1 | 4/2005 |
| WO | 2006137932 A2 | 12/2006 |
| WO | 2007059816 A1 | 5/2007 |
| WO | 2007062177 A2 | 5/2007 |
| WO | 2007069092 A3 | 6/2007 |
| WO | 2008012543 A1 | 1/2008 |
| WO | 2008048970 A2 | 4/2008 |
| WO | 2008157379 A2 | 12/2008 |
| WO | 2009072812 A2 | 6/2009 |

OTHER PUBLICATIONS

Morocho, et al., "Novel Biotin Phosphoramidites with Super-long Tethering Arms," Nucleosides, Nucleotides & Nucleic Acids, 2003, pp. 1439-1441, vol. 22, Nos. 5-8.
Rheinnecker, et al., Multivalent Antibody Fragments with High Functional Affinity for a Tumor-Associated Carbohydrate Antigen, Journal of Immunology, 1996, pp. 2989-2997, vol. 157.
Ren, et al., "A Biocompatible Condensation Reaction for the Labeling of Terminal Cysteine Residues on Proteins," Angewandte Chemie International Edition, 2009, pp. 9658-9662, vol. 48.
Roget, et al., "Synthesis and use of labelled nucleoside phosphoramidite building blocks bearing a reporter group: biotinyl, dinitrophenyl, pyrenyl and dansyl," Nucleic Acids Research, 1989, pp. 7643-7651, vol. 17, No. 19.
Seela, et al., "Oligodeoxyribonucleotides containing 1,3= propanediol as nucleoside substitute," Nucleic Acids Research, 1987, pp. 3113-3129, vol.15, No. 7.
Su, et al., "Novel Non-Nucleosidic Phosphoramidites for Oligonucleotide Modification and Labeling," Bioorganic & Medicinal Chemistry Letters, 1997, pp. 1639-1644, vol. 7, No. 13.
Sunbul et al. "Site specific protein labeling by enzymatic post-translational modification," Organic & Biomolecular Chemistry, 2009, pp. 3361-3371, vol. 7.
Taki, et al., "Transglutaminase-mediated N- and C-terminal fluorescein labeling of a protein can support the native activity of the modified protein," Protein Engineering, Design & Selection, 2004, pp. 119-126, vol. 17, No. 2.
Taylor, et al., "Native Chemical Ligation: SemiSynthesis of Post-translationally Modified Proteins and Biological Probes," Nucleic Acids and Molecular Biology, 2009, pp. 65-96, vol. 22.
Wang, et al., "Site-Specific Fluorescent Labeling of DNA Using Staudinger Ligation," Bioconjugate Chemistry, 2003, pp. 697-701, vol. 14.
Wojczewski, et al., "Fluorescent Oligonucleotides-Versatile Tools as Probes and Primers for DNA and RNA Analysis," Synlett, 1999, pp. 1667-1678, No. 10.
Seo, et al., Post-translational Modifications and Their Biological Functions: Proteomic Analysis and Systematic Approaches, Journal of Biochemistry and Molecular Biology, 2004, pp. 35-44, vol. 37, No. 1.
Williams, et al., Creating Protein Affinity Reagents by Combining Peptide Ligands on Synthetic DNA Scaffolds, Journal of the American Chemical Society, 2009, pp. 17233-17241, vol. 131.
Wright, et al., Phage display of chelating recombinant antibody libraries, Molecular Immunology, 2007, pp. 2860-2869, vol. 44.
Behrens, et al., "Synthesis of Achiral Linker Reagents for Direct Labelling of Oligonucleotides on Solid Supports," Nucleosides & Nucleotides, 1999, pp. 291-305, vol. 18, No. 2.
Brennan, et al., "Preparation of Bispecific Antibodies by Chemical Recombination of Monoclonal Immunoglobulin G1 Fragments," Science, Jul. 1985, pp. 81-83, vol. 229.
Bruck, et al., "Purification of Mouse Monoclonal Antibodies from Ascitic Fluid by DEAE Alfi-Gel Blue Chromatography," Methods in Enzymology, 1986, pp. 587-596, vol. 121.
Caldas, et al., Humanization of the anli-CD18 antibody 6.7: an unexpected effect of a framework residue in binding to antigen, Molecular Immunology, 2003, pp. 941-952, vol. 39.
Carter, et al., "High Level *Escherichia Coli* Expression and Production of a Bivalent Humanized Antibody Fragment," Nature Bio/Technology, Feb. 1992, pp. 163-167, vol. 10.
Cheong, et al., Affinity Enhancement of Bispecific Antibody Against Two Different Epilopes in the Same Antigen, Biochemical and Biophysical Research Communications, 1990, pp. 795-800, vol. 173, No. 3.
Chien, et al., Significant structural and functional change of an antigen-binding site by a distant amino acid substitution: Proposal of a structural mechanism, Proceedings of the National Academy of Sciences USA, 1989, pp. 5532-5536, vol. 86.
Cocca, et al., Tandem Affinity Tags for the Purification of Bivalent Anti-DNA Single-Chain Fv Expressed in *Echerichia coli*, Protein Expression and Purification, 1999, pp. 290-298, vol. 17.
Cocuzza, et al., "A Phosphoramidite Reagent for Automated Solid Phase Synthesis of 5'-Biotinylated Oligonucleotides," Tetrahedron Letters, 1989, pp. 6287-6290, vol. 30, No. 46.
Colman, P., Effects of amno acid sequence changes on antibody-antigen interactions, Res. Immunology, 1994, vol. 145, No. 1, pp. 33-36.
De Graaf, et al., Nonnatural Amino Acids for Site-Specific Protein Conjugation, Bioconjugate Chemistry, Jul. 2009, pp. 1281-1295, vol. 20, No. 7.
Dekruif, et al., Leucine zipper dimerized bivalent and bispecific SCFV antibodies from a phage display library. [Abst. 308], Immunotechnology, 1996, pp. 298-299, vol. 2.
Dekruif, et al., Leucine Zipper Dimerized Bivalent and Bispecific SCFV Antibodies from a Semi-synthetic Antibody Phage Display Library, The Journal of Biological Chemistry, 1996, pp. 7630-7634, vol. 271, No. 13.
Dong, et al., "Stable IgG-like Bispecific Antibodies Directed toward the Type I Insulin-like Growth Factor Receptor Demonstrate Enhanced Ligand Blockade and Anti-tumor Activity," Journal of Biological Chemistry, Feb. 11, 2011, pp. 4703-4717, vol. 286, No. 6.
Fischer, et al., Bispecific Antibodies: Molecules Thal Enable Novel Therapeutic Strategies, Pathobiology, 2007, pp. 3-14, 74.
Francois, et al., "Construction of a Bispecific Antibody Reacting with the α- and β-Chains of the Human IL-2 Receptor," The Journal of Immunology, May 15, 1993, pp. 4610-4619, vol. 150, No.10.
Frese, et al., "Formylglycine Aldehyde Tag-Protein Engineering through a Novel Post-translational Modification," ChemBioChem, 2009, pp. 425-427, vol. 10.
Galfre, et al., "[1] Preparation of Monoclonal Antibodies: Strategies and Procedures," Methods in Enzymology, 1981, pp. 3-46, vol. 73.
Gautier, et al., "An Engineered Protein Tag for Multiprotein Labeling in Living Cells," Chemistry & Biology, Feb. 2008, pp. 128-136, vol. 15.

(56) References Cited

OTHER PUBLICATIONS

Giusti, et al., Somatic diversification of S107 from an antiphosphocholine to an anti-DNA autoantibody is due to a single base change in its heavy chain variable region, Proceedings of the National Academy of Sciences USA, 1987, pp. 2926-2930, vol. 84.

Hackenberger, et al., "Chemoselective Ligation and Modification Strategies for Peptides and Proteins," Angewandte Chemie International Edition, 2008, pp. 10030-10074, vol. 47.

Harlow et al., Antibodies: A Laboratory Manual (1998), Cold Spring Harbor Laboratory press, Cold Spring Harbor, NY, pp. 23-26.

Hayden, et al., Antibody engineering, Current Opinion in Immunology, 1997, pp. 201-212, vol. 9.

Hey, et al. "Artificial, non-antibody binding proteins for pharmaceutical and industrial applications," Trends in Biotechnology, Oct. 2005, pp. 514-522, vol. 23, No. 10.

Hoppe, et al., "A parallel three stranded a-helical bundle at the nucleation site of collagen triple-helix formation," FEBS Letters, 1994, pp. 191-195, vol. 344.

Hudson, et al., "Engineered antibodies," Nature Medicine, Jan. 2003, pp. 129-134, vol. 9, No. 1.

Iyer, Radhakrishnan P. et al., "Abasic oligodeoxyribonucleoside phosphorothioates: synthesis and evaluation as anti-HIV-1 agents," Nucleic Acids Research, 1990, pp. 2855-2859, vol. 18, No. 10.

Jarvius, et al., "In Situ Detection of Phosphorylated Platelet-derived Growth Factor Receptor β Using a Generalized Proximity Ligation Method", Molecular & Cellular Proteomics, 2007, pp. 1500-1509, vol. 6.

Kostelny, et al., Formation of a Bispecific Antibody by the Use of Leucine Zippers, The Journal of immunology, 1992, pp. 1547-1553, vol. 148, No. 5.

Landschulz, et al., "The Leucine Zipper: A Hypothetical Structure Common to a New Class of DNA Binding Proteins," Science, 1988, pp. 1759-1764, vol. 240.

Ledbetier, et al., "CD28 Ligation in T-Cell Activation: Evidence for Two Signal Transduction Pathways," Blood, Apr. 1, 1990, pp. 1531-1539, vol. 75, No. 7.

Lee, et al., Humanization of an angonistic anti-death receptor 4 single chain variable fragment antibody and avidity-mediated enhancement of its cell death-inducing activity, Molecular Immunology, 2010, pp. 816-824, vol. 47.

Lederman et al. "A single amino acid substitution in a common African allele of the CD4 molecule ablates binding of the monoclonal antibody, OKT4" Mol Immunol. 1991, vol. 11, pp. 1171-1181.

Machida, et al., Module Assembly for Protein-Surface Recognition: Geranylgeranyltransferase I Bivalent inhibitors for Simultaneous Targeting of Interior and Exterior Protein Surfaces, Chemistry & European Journal, 2008, pp. 1392-1401, vol. 14.

Mann, et al., Proteomic analysis of post-translational modifications, Nature Biotechnology, J003, pp. 255-261, vol. 21.

Mao, et al., "Sortase-Mediated Protein Ligation: A New Method for Protein Engineering," Journal of the American Chemical Society, 2004, pp. 2670-2671, vol. 126.

McKeen, et al., "Synthesis of fluorophore and quencher monomers for use in Scorpion primers and nucleic acid structural probes," Organic & Biomolecular Chemistry, 2003, pp. 2267-2275, vol. 1.

Meyer, et al., "Oligonucleotide Sequential Bis-Conjugation via Click-Oxime and Click-Huisgen Procedures," Journal of Organic Chemistry, 2010, pp. 3927-3930, vol. 75.

Morimoto, et al., "Single-step purification of F(ab')2 fragments of mouse monoclonal antibodies (immunoglobulins G1) by hydrophobic interaction high performance liquid chromatography using TSKgel Phenyl-5PW," Journal of Biochemical and Biophysical Methods, 1992, pp. 107-117, vol. 24.

Nelson, et al., "Oligonucleotide labeling methods 3. Direct labeling of oligonucleotides employing a novel, non-nucleosidic, 2-aminobuytl-1, 3-propanediol backbone," Nucleic Acids Research, 1992, pp. 6253-6259, vol. 20, No. 23.

Neri, et al., High-affinity Antigen Binding by Chelating Recombinant Antibodies (CRAbs), Journal of Molecular Biology, 1995, pp. 367-373, vol. 246.

Otrock, et al., "Vascular endothelial growth factor family of ligands and receptors: Review," Blood Cells, Molecules, and Diseases, 2007, pp. 258-268, vol. 38.

Pack, et al., Miniantibodies: Use of Amphipathic Helices to Produce Functional, Flexibly linked Dimeric Fv Fragments with High Avidity in *Escherichia coli*, Biochemistry, 1992, pp. 1579-1584, vol. 31, No. 6.

Pack, et al., Tetravalent Miniantibodies with High Avidity Assembling in *Escherichia coli*, Journal of Molecular Biology, 1995, pp. 28-34, vol. 246.

Pon, R., "A Long Chain Biotin Phosphoramidite Reagent for the Automated Synthesis of 5'-Biotinylated Oligonucleotides," Tetrahedron Letters, 1991, pp. 1715-1718, vol. 32, No. 14.

Proft, T., "Sortase-mediated protein ligation: an emerging biotechnology tool for protein modification and immobilisation," Biotechnology Letters, 2010, pp. 1-10, vol. 32.

Prokhorenko, et al., "Incorporation of a Pyrene Nucleoside Analogue into Synthetic Oligodeoxynucleotides Using a Nucleoside-Like Synthon," Bioorganic & Medicinal Chemistry Letters, 1995, pp. 2081-2084, vol. 5, No. 18.

Putnam, William C. and Bashkin, James K., "Synthesis and Evaluation of RNA Transesterification Efficiency Using Stereospecific Serinol-Terpyridine Conjugates," Nucleosides, Nucleotides, and Nucleic Acids, 2005, pp. 1309-1323, vol. 24, No. 9.

Ramzaeva, et al., "Oligonucleotides Functionalized by Fluorescein and Rhodamine Dyes: Michael Addition of Methyl Acrylate to 2'-Deoxypseudouridine," Helvetica Chimica Acta, 2000, pp. 1108-1126, vol. 83.

\* cited by examiner

Fab' 8.1.2

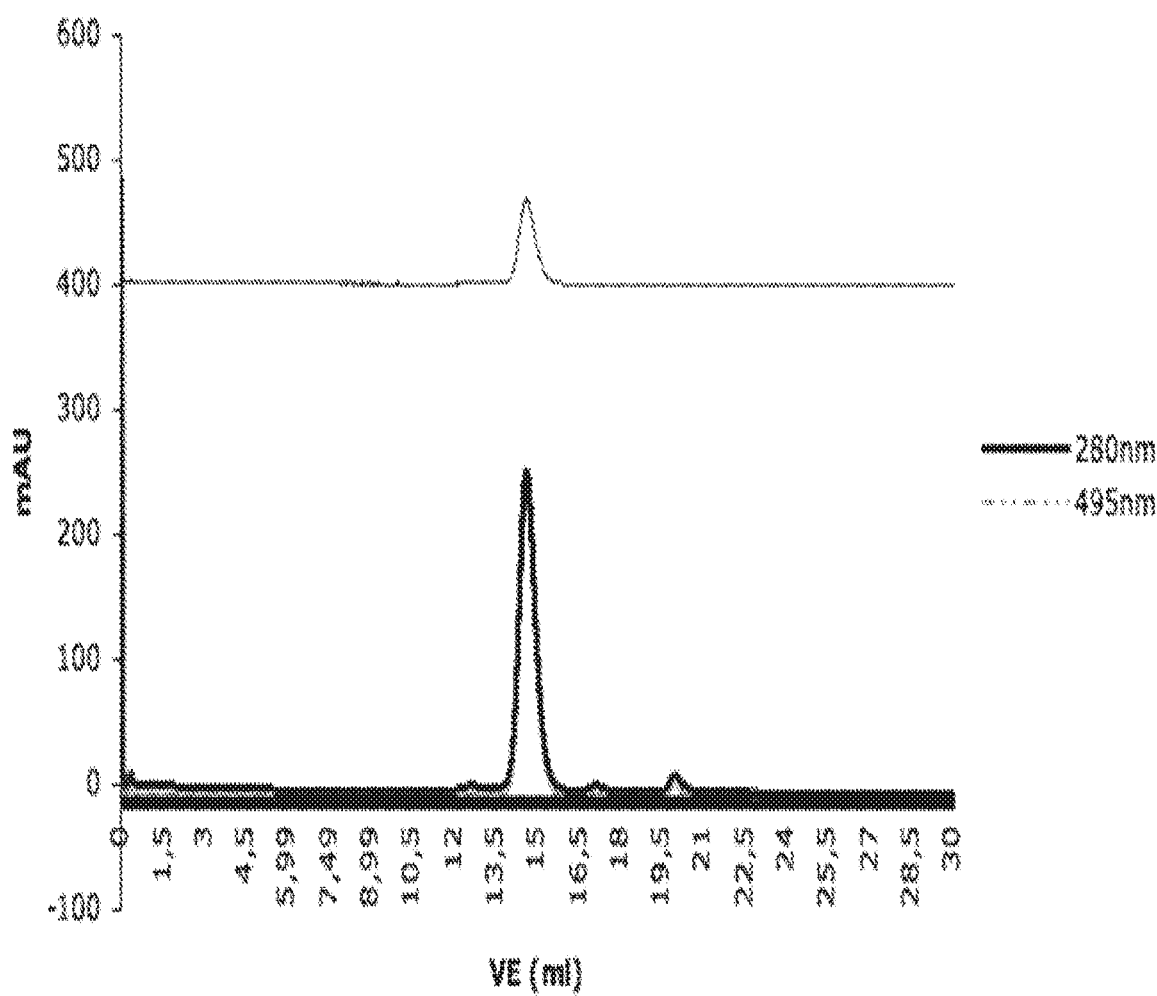

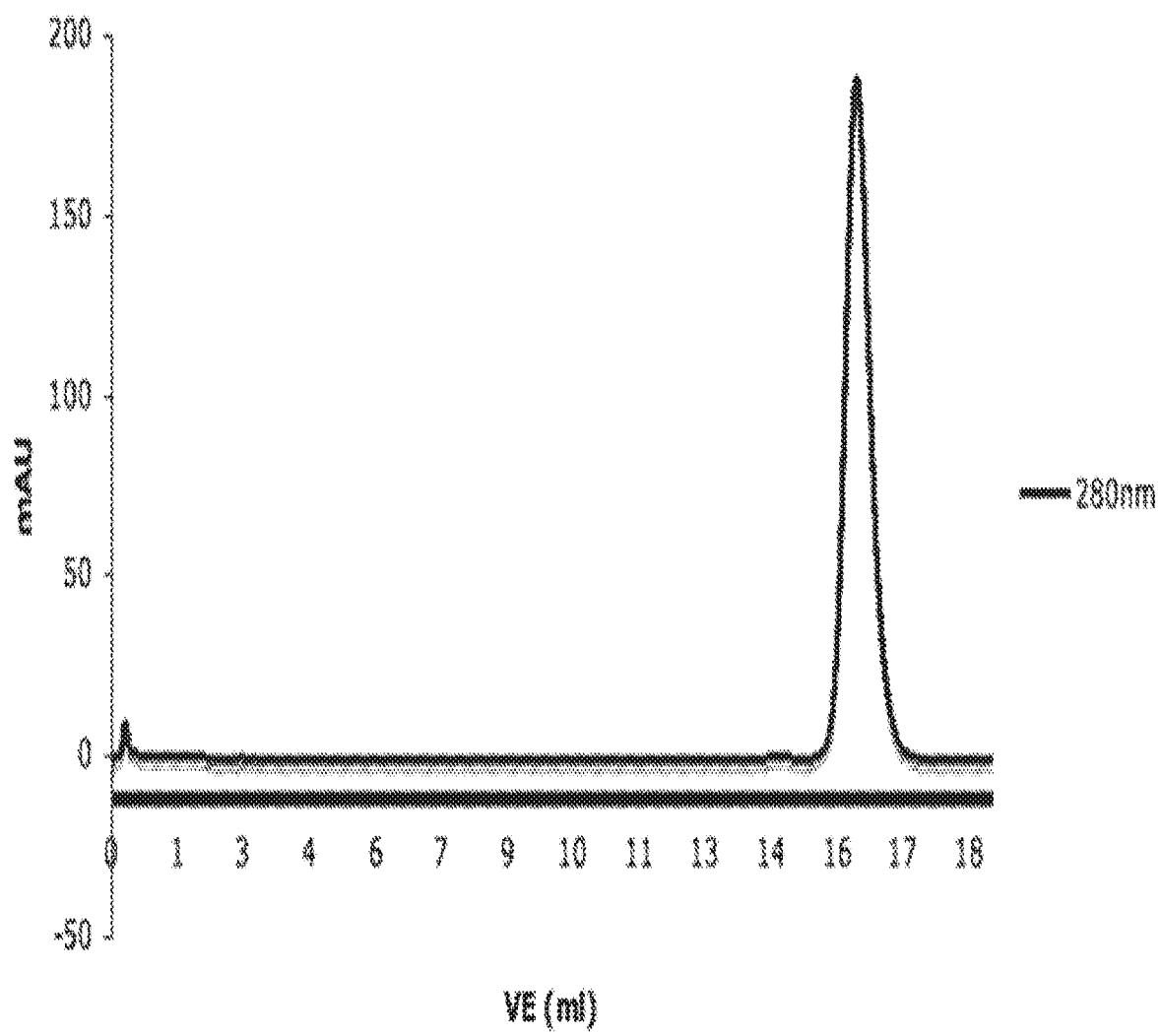

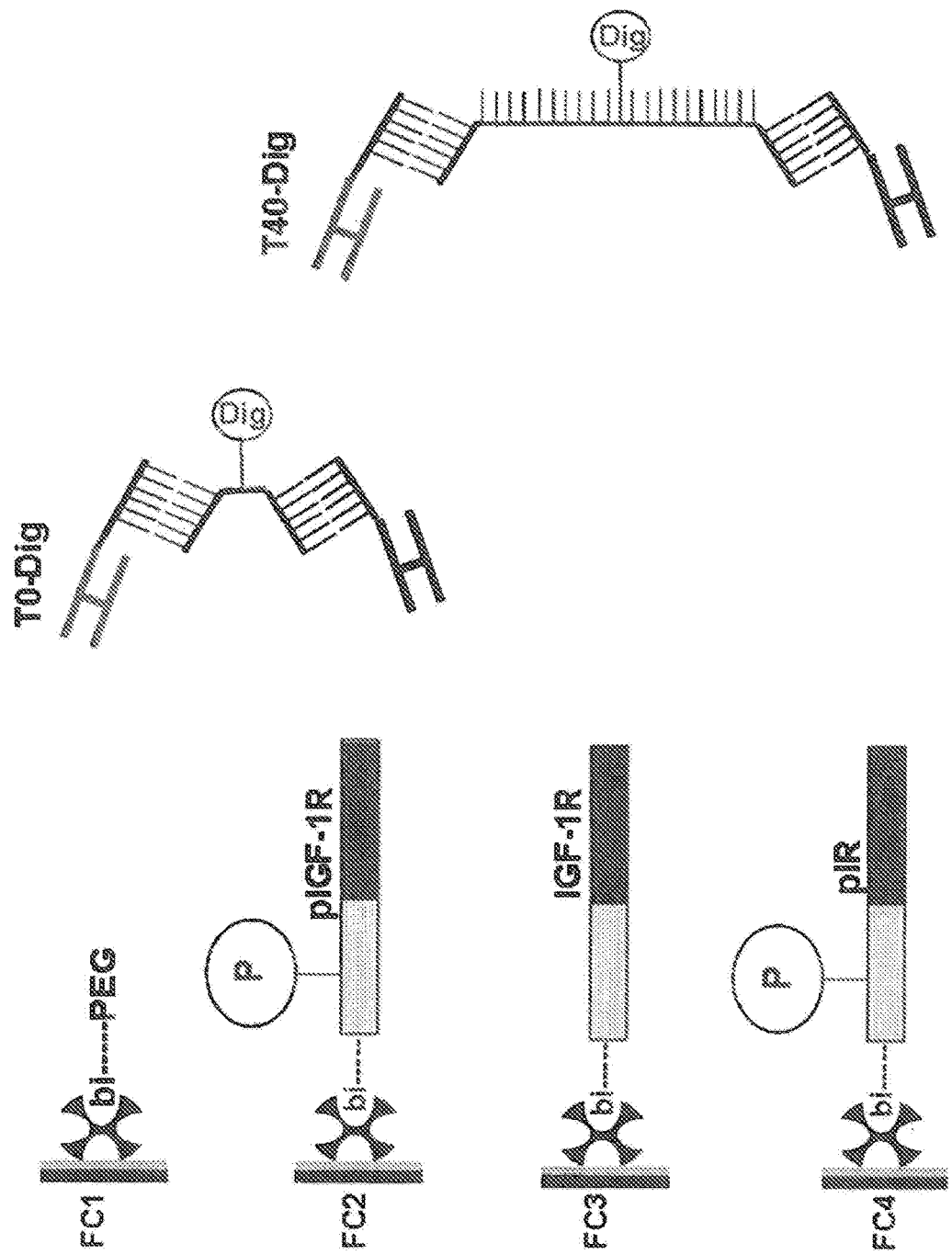

FIG. 9

| Linker | Analyte | ssFab 1 | ssFab 2 | ka (1/Ms) | kd (1/s) | t1/2 diss (min) | KD (M) | KD (nM) |
|---|---|---|---|---|---|---|---|---|
| T40 | pIGF-1R | 8.1.2 | 1.4.168 | 2.24E+06 | 2.79E-05 | 414 | 1.25E-11 | 0.01 |
| T40 | pIGF-1R | 8.1.2 | - | 1.17E+06 | 2.21E-02 | 0.5 | 1.89E-08 | 19 |
| T40 | pIGF-1R | - | 1.4.168 | 1.96E+06 | 4.19E-03 | 3 | 2.14E-09 | 2 |
| T40 | pINR | 8.1.2 | 1.4.168 | 1.57E+06 | 3.70E-02 | 0.3 | 2.36E-08 | 24 |
| T40 | pINR | 8.1.2 | - | 1.36E+06 | 4.45E-02 | 0.3 | 3.27E-08 | 33 |
| T40 | pINR | - | 1.4.168 | n.i. | n.i. | n.i. | n.i. | n.i. |
| T40 | IGF-1R | 8.1.2 | 1.4.168 | 2.73E+06 | 2.66E-03 | 4.3 | 9.73E-10 | 1 |
| T40 | IGF-1R | 8.1.2 | - | n.i. | n.i. | n.i. | n.i. | n.i. |
| T40 | IGF-1R | - | 1.4.168 | 3.30E+06 | 3.62E-03 | 3 | 1.10E-09 | 1 |
| T0 | pIGF-1R | 8.1.2 | 1.4.168 | 1.75E+06 | 6.01E-05 | 192 | 3.44E-11 | 0.03 |
| T0 | pIGF-1R | 8.1.2 | - | 1.03E+06 | 2.22E-02 | 1 | 2.15E-08 | 22 |
| T0 | pIGF-1R | - | 1.4.168 | 1.12E+06 | 2.91E-03 | 4 | 2.59E-09 | 3 |
| T0 | pINR | 8.1.2 | 1.4.168 | 1.70E+06 | 4.18E-02 | 0.3 | 2.46E-08 | 25 |
| T0 | pINR | 8.1.2 | - | 1.09E+06 | 4.83E-02 | 0.2 | 4.41E-08 | 44 |
| T0 | pINR | - | 1.4.168 | n.d | n.d. | n.d | n.d. | n.d. |
| T0 | IGF-1R | 8.1.2 | 1.4.168 | 1.98E+06 | 2.38E-03 | 5 | 1.20E-09 | 1 |
| T0 | IGF-1R | 8.1.2 | - | n.i. | n.i. | n.i. | n.i. | n.i. |
| T0 | IGF-1R | - | 1.4.168 | 2.41E+06 | 3.26E-03 | 4 | 1.35E-09 | 1 |

FIG. 14
H322M Xenograft
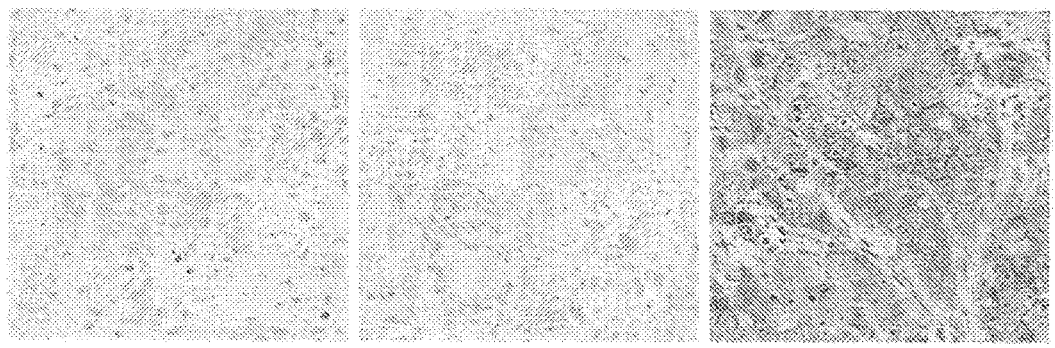
ssFab' 30.4.33
ssFab' 1.4.168
Dual Binder

FIG. 16

| Linker | Analyte | ssFab 1 | ssFab 2 | ka (1/Ms) | kd (1/s) | t1/2 diss (min) | KD (M) | KD (nM) |
|---|---|---|---|---|---|---|---|---|
| HEG 8xC18 | pIGF-1R | 30.4.33 | 1.4.168 | 1.24E+06 | 1.39E-05 | 830 | 1.12E-11 | 0.011 |
| | | 30.4.33 | - | 7.35E+05 | 1.57E-03 | 7.3 | 2.02E-09 | 2 |
| | | - | 1.4.168 | 1.09E+06 | 3.22E-03 | 3.5 | 2.96E-09 | 3 | ssFab' 30.4.33

DETECTION OF A POSTTRANSLATIONALLY MODIFIED POLYPEPTIDE BY A BIVALENT BINDING AGENT

CROSS-REFERENCE TO RELATED APPLICATIONS

This application is a continuation application of U.S. patent application Ser. No. 13/923,618, filed Jun. 21, 2013, which is a continuation of International Application No. PCT/EP2011/073560, filed Dec. 21, 2011, which claims the benefit of European Patent Application No. 10196687.7, filed Dec. 23, 2010, and European Patent Application No. 11173832.4, filed Jul. 13, 2011, the disclosures of which are hereby incorporated by reference in their entirety.

SEQUENCE LISTING

A paper copy of the Sequence Listing and a computer readable form of the Sequence Listing containing the file named "27204_US2ST_ST25.txt", which is 17,469 bytes in size (as measured in MICROSOFT WINDOWS EXPLORER), are provided herein and are herein incorporated by reference. This Sequence Listing consists of SEQ ID NOs:1-29.

BACKGROUND OF THE DISCLOSURE

The primary structure of a polypeptide, i.e. its sequence, is determined by the nucleic acid coding for it. However, knowing the primary structure of a polypeptide is only part of the story. Many polypeptides—estimates range from 50 to 90%—undergo secondary modifications. Dependent e.g. on the type of secondary modification, the percentage of modified polypeptides and/or e.g. on the exact position/location of a secondary modification, a polypeptide with one and the same primary structure can assume quite different biological functions.

Secondary protein modifications finely tune the cellular functions of each protein. Understanding the relationship between post-translational modifications and functional changes ("posttranslatomics") is enormous effort going on all around the world, not unlike to the human genome project. Proteomics, combined with separation technology and mass spectrometry, makes it possible to dissect and characterize the individual parts of post-translational modifications and provide a systemic analysis.

While some decade ago a protein has been thought of as a linear polymer of amino acids, it first became evident that such polypeptide chain may be decorated with simple amino acid modifications. However, very complicated modifications in one protein are lately discovered in many processes. A variety of chemical modifications have been observed in a single protein and these modifications alone or in various combinations occur in a time- and signal-dependent manner. Post-translational modifications of proteins determine their tertiary and quaternary structures and regulate their activities and functions. The progress in "posttranslatomics" has led to many ground-breaking insights into the interplay of secondary modification and biological function for example in relation to regulation of biochemical pathways and to disease states involving these proteins.

Detection and quantitation of a secondarily modified polypeptide, however, requires sophisticated tools and techniques. Frequently various types of separation and optionally fragmentation techniques are combined with mass spectroscopy in order to identify a posttranslationally modified polypeptide.

The immunological detection of a posttranslationally modified polypeptide has consistently turned out to be rather difficult. Various types of problems may be encountered. It may be difficult to obtain a required immunogen in sufficient purity and quantity. The antibodies obtained according to standard immunization and screening methods may not have the required specificity and/or affinity. Especially when there is a need for an antibody of highly reproducible, consistent quality, e.g. a monoclonal antibody, it may turn out very demanding to obtain such an antibody. Such antibody would have to bind strongly to an epitope consisting of the secondary modification and parts of the polypeptide carrying it. However, many binding agents generated by routine procedures show cross-reactions to other polypeptides with the same kind of posttranslational modification, do not exhibit the required affinity to the epitope recognized and/or show cross-reactivity to the non-modified polypeptide.

Many of the larger polypeptides even comprise several sites for one type of posttranslational modification to occur. There may be e.g. several threonine residues that are glycosylated in a statistical manner. Assessing the glycosylation status of such polypeptide might require several different antibodies with specificity for each of the positions potentially carrying the posttranslational modification.

BRIEF SUMMARY OF THE DISCLOSURE

The present disclosure relates to a bivalent binding agent consisting of a first monovalent binder that binds to a polypeptide epitope of a target polypeptide, a second monovalent binder that binds to a posttranslational polypeptide modification on the target polypeptide and a linker. Further disclosed is a method for the detection of a posttranslationally modified target polypeptide by aid of such bivalent binding agent, a method of making such bivalent binding agent and the use of such bivalent agent in histological staining procedures.

The present disclosure provides a binding agent that binds to a posttranslationally modified polypeptide with high affinity, and can be produced reproducibly in virtually unlimited quantity and uncompromised quality.

Posttranslational polypeptide modifications are crucial for modulating and/or regulating the property and/or activity of a polypeptide. One advantageous method for use in the detection of a certain type of secondary modification on a target polypeptide would be by means of a specific binding agent.

The present embodiment relates to a bivalent binding agent binding a posttranslationally modified target polypeptide consisting of two monovalent binders that are linked to each other via a linker, wherein the first monovalent binder binds to a polypeptide epitope of said target polypeptide, wherein the second monovalent binder binds to a posttranslational polypeptide modification, wherein each monovalent binder has a kdiss in the range of $5 \times 10^{-3}$/sec to $10^{-4}$/sec, and wherein the bivalent binding agent has a kdiss of $3 \times 10^{-5}$/sec or less.

Also disclosed is a method for obtaining a bivalent binding agent that specifically binds a posttranslationally modified target polypeptide, the method comprising the steps of selecting a first monovalent binder that binds to a non-posttranslationally modified epitope of said target polypeptide with a kdiss of between $5 \times 10^{-3}$/sec to $10^{-4}$/sec, selecting a second monovalent binder that binds to a posttranslational polypeptide modification with a Kdiss of $5 \times 10^{-3}$/sec to $10^{-4}$/sec, coupling both monovalent binders by a linker, and selecting a bivalent binding agent having a Kdiss-value of $3 \times 10^{-5}$/sec or less.

Also disclosed herein as some embodiments comprising methods of using the novel bivalent binding agent, for example in an immunohistochemical procedure.

BRIEF DESCRIPTION OF THE FIGURES

The features of this disclosure, and the manner of attaining them, will become more apparent and the disclosure itself will be better understood by reference to the following description of embodiments of the disclosure taken in conjunction with the accompanying drawing.

FIG. 1 B presents an analytical gel filtration experiments assessing efficiency of the anti-pIGF1-R dual binder assembly. Diagrams a, b and c show the elution profile of the individual dual binder components (flourescein-ssFab' 1.4.168, CY5™-ssFab' 8.1.2 and linker DNA (T=0); ssFab' denotes a Fab'-fragment conjugated to a single-stranded oligonucleotide). The thicker (bottom) curve represents absorbance measured at 280 nm indicating the presence of the ssFab' proteins or the linker DNA, respectively. The thinner top curve in b) and d) (absorbance at 495 nm) indicates the presence of fluorescein and the thinner top curve in a) and the middle curve in d) (absorbance at 635 nm) indicates the presence of CY5™. Comparison of the elution volumes of the single dual binder components ($VE_{ssFab'\ 1.4.168}$ ~15 ml; $VE_{ssFab'\ 8.1.2}$ ~15 ml; $VE_{linker}$ ~16 ml) with the elution volume of the reaction mix ($VE_{mix}$ ~12 ml) demonstrates that the dual binder assembly reaction was successful (rate of yield: ~90%). The major 280 nm peak that represents the eluted dual binder nicely overlaps with the major peaks in the 495 nm and 635 nm channel, proving the presence of both ssFab' 8.1.2 and ssFab'1.4.168 in the peak representing the bivalent binding agent.

FIG. 1 C presents an analytical gel filtration experiments assessing efficiency of the anti-pIGF1-R dual binder assembly. Diagrams a, b and c show the elution profile of the individual dual binder components (flourescein-ssFab' 1.4.168, CY5™-ssFab' 8.1.2 and linker DNA (T=0); ssFab' denotes an Fab'-fragment conjugated to a single-stranded oligonucleotide). The thicker (bottom) curve represents absorbance measured at 280 nm indicating the presence of the ssFab' proteins or the linker DNA, respectively. The thinner top curve in b) and d) (absorbance at 495 nm) indicates the presence of fluorescein and the thinner top curve in a) and the middle curve in d) (absorbance at 635 nm) indicates the presence of CY5™. Comparison of the elution volumes of the single dual binder components ($VE_{ssFab'\ 1.4.168}$ ~15 ml; $VE_{ssFab'\ 8.1.2}$ ~15 ml; $VE_{linker}$ ~16 ml) with the elution volume of the reaction mix ($VE_{mix}$ ~12 ml) demonstrates that the dual binder assembly reaction was successful (rate of yield: ~90%). The major 280 nm peak that represents the eluted dual binder nicely overlaps with the major peaks in the 495 nm and 635 nm channel, proving the presence of both ssFab' 8.1.2 and ssFab'1.4.168 in the peak representing the bivalent binding agent.

FIG. 1 D presents an analytical gel filtration experiments assessing efficiency of the anti-pIGF1-R dual binder assembly and shows the elution profile after the 3 components needed to form the bivalent binding agent had been mixed in a 1:1:1 molar ratio. The thicker (bottom) curve represents absorbance measured at 280 nm indicating the presence of the ssFab' proteins or the linker DNA, respectively. The thinner top curve in b) and d) (absorbance at 495 nm) indicates the presence of fluorescein and the thinner top curve in a) and the middle curve in d) (absorbance at 635 nm) indicates the presence of CY5™. Comparison of the elution volumes of the single dual binder components ($VE_{ssFab'\ 1.4.168}$ ~15 ml; $VE_{ssFab'\ 8.1.2}$ ~15 ml; $VE_{linker}$ ~16 ml) with the elution volume of the reaction mix ($VE_{mix}$ ~12 ml) demonstrates that the dual binder assembly reaction was successful (rate of yield: ~90%). The major 280 nm peak that represents the eluted dual binder nicely overlaps with the major peaks in the 495 nm and 635 nm channel, proving the presence of both ssFab' 8.1.2 and ssFab'1.4.168 in the peak representing the bivalent binding agent.

FIG. 2 shows a scheme of the BIACORE™ experiment. Schematically and exemplarily, two binding molecules in solution are shown: The T0-T-Dig (linker 16), bivalent binding agent and the T40-T-Dig (linker 15), bivalent binding agent. Both these bivalent binding agents only differ in their linker-length (a central digoxigenylated T with no additional T versus 40 additional Ts (20 on each side of the central T-Dig), between the two hybridizing nucleic acid sequences). Furthermore, ssFab' fragments 8.1.2 and 1.4.168 were used.

FIG. 9 is kinetic data of the dual binder experiment. T40-T-Bi linker dual binder with ssFab' 8.1.2 and ssFab' 1.4.168 (=T40 in the Figure) shows a 1300-fold lower off-rate (kd=2.79E−05/s) versus pIGF-1R when compared to pIR (kd=3.70E−02/s)

FIG. 13 B presents Results from IHC experiments with FFPE 3T3 cell pellets. The detection molecule composed of an 8×C18 linker molecule (linker 14 of example 2.4) and only ssFab' 1.4.168 or only ssFab' 30.4.33 did not produce a staining on any of the tested FFPE 3T3 cell pellets (rows 1&2). In contrast, detection with the full dual binder molecule (consisting of both ssFab' fragments+8×C18 linker) led to a staining—but only on IGF-1R overexpressing cells that were stimulated with IGF-1 (row 3). No cross-reactivity was observed on cells overexpressing IR even when phosphorylation of IR had been induced.

FIG. 13 C presents IHC experiment comparing the performance of anti-pIGF-1R dual binders with different linker length (linkers contained 2×C18, 4×C18, 6×C18 or 8×C18 spacers, see example 2.4) on IGF-1R-overexpressing FFPE 3T3 cells that had been stimulated with IGF-1 to induce IGF-1R phosphorylation FIG. 14 is an immunostaining of H322M xenograft sections. 10 μg/ml per ssFab' fragment (ssFab' 30.4.33 or/and ssFab' 1.4.168, respectively) and an equimolar amount of 8×C18 linker molecule were used for detection. A biotin label within the linker molecule served as a detection tag for the streptavidin-based Ventana iVIEW DAB detection kit FIG. 16 is a table summarizing the kinetic data of the dual binder experiment. The dual binder containing both ssFab' 30.4.33 and ssFab' 1.4.168 shows a 230-fold lower off-rate (kd=1.39E−05/s) than ssFab' 1.4.168 (kd=3.22E−03/s) and a 110-fold lower off-rate than ssFab' 30.4.33 (kd=1.57E−03/s) alone

FIG. 20 B presents Results from IHC experiments with Hek293 cell pellets. The detection molecule composed of an 4×C18 linker molecule (linker 12 of example 2.4) and only ssFab 4.1.15 or only ssFab 7.2.32 did not produce a staining on any of the tested FFPE Hek293 cell pellets (rows 1&2). In contrast, detection with the full dual binder molecule (consisting of both ssFab fragments+4×C18 linker) led to a staining—but only on wild-type HER3 overexpressing cells that were stimulated with NRG1-β1 (row 3; column 2). No staining was observed on unstimulated cells (row 3; column 1) and NRG1-β1-stimulated cells that overexpress mutated HER3(Y>F) (lacking the Tyr1289 phosphorylation site) instead of wild-type HER3 (row 3; column 3), respectively.

Figure 1A:
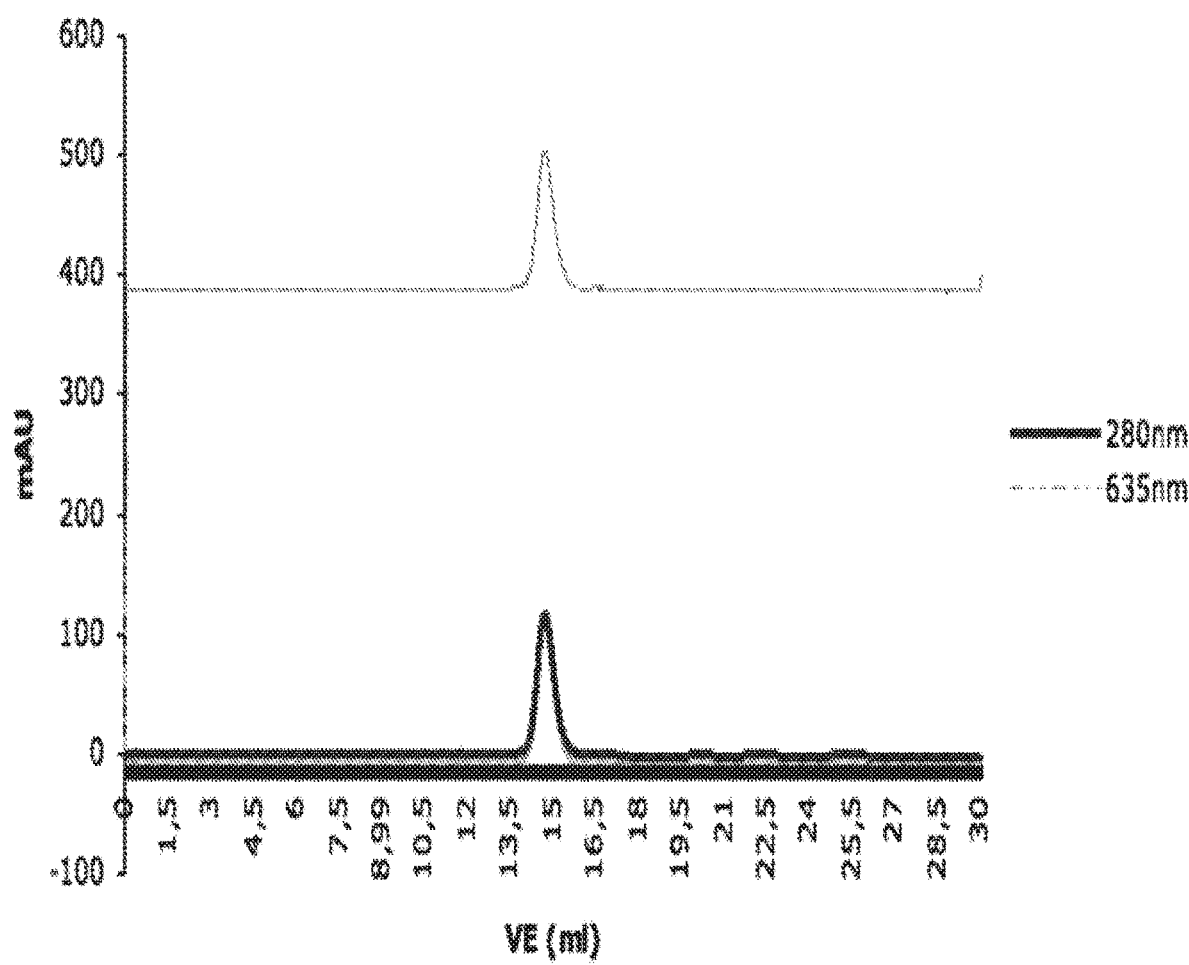
FIG. 1 A presents an analytical gel filtration experiments assessing efficiency of the anti-pIGF1-R dual binder assembly. Diagrams a, b and c show the elution profile of the individual dual binder components (flourescein-ssFab' 1.4.168, CY5™-ssFab' 8.1.2 and linker DNA (T=0); ssFab' denotes an Fab'-fragment conjugated to a single-stranded oligonucleotide). The thicker (bottom) curve represents absorbance measured at 280 nm indicating the presence of the ssFab' proteins or the linker DNA, respectively. The thinner top curve in b) and d) (absorbance at 495 nm) indicates the presence of fluorescein and the thinner top curve in a) and the middle curve in d) (absorbance at 635 nm) indicates the presence of CY5™. Comparison of the elution volumes of the single dual binder components ($VE_{ssFab'\ 1.4.168}$ ~15 ml; $VE_{ssFab'\ 8.1.2}$ ~15 ml; $VE_{linker}$ ~16 ml) with the elution volume of the reaction mix ($VE_{mix}$ ~12 ml) demonstrates that the dual binder assembly reaction was successful (rate of yield: ~90%). The major 280 nm peak that represents the eluted dual binder nicely overlaps with the major peaks in the 495 nm and 635 nm channel, proving the presence of both ssFab' 8.1.2 and ssFab'1.4.168 in the peak representing the bivalent binding agent.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

BRIEF DESCRIPTION OF THE SEQUENCE LISTING

```
Antibody fragments
                                         SEQ ID NO: 1
V_H (mAb 1.4.168):
QCDVKLVESG GGLVKPGGSL KLSCAASGFT FSDYPMSWVR

QTPEKRLEWV ATITTGGTYT YYPDSIKGRF TISRDNAKNT

LYLQMGSLQS EDAAMYYCTR VKTDLWWGLA YWGQGTLVTV SA

SEQ ID NO: 2
V_L (mAb 1.4.168):
QLVLTQSSSA SFSLGASAKL TCTLSSQHST YTIEWYQQQP

LKPPKYVMEL KKDGSHTTGD GIPDRFSGSS SGADRYLSIS

NIQPEDESIY ICGVGDTIKE QFVYVFGGGT KVTVLG

SEQ ID NO: 3
V_H (mAb 8.1.2):
EVQLQQSGPA LVKPGASVKM SCKASGFTFT SYVIHWVKQK

PGQGLEWIGY LNPYNDNTKY NEKFKGKATL TSDRSSSTVY

MEFSSLTSED SAVYFCARRG IYAYDHYFDY WGQGTSLTVS S

SEQ ID NO: 4
V_L (mAb 8.1.2):
QIVLTQSPAI MSASPGEKVT LTCSASSSVN YMYWYQQKPG

SSPRLLIYDT SNLASGVPVR FSGSGSVTSY SLTISRMEAE

DAATYYCQQW STYPLTFGAG TKLELK
```

```
                                         SEQ ID NO: 19
V_H (mAb 30.4.33):
EVQLQESGPE VAKPGASVKM SCKASGYTFT DYIIHWVKQR

PGQDLEWIGY INPYNDKSKY NEKFKDKATL TSDRSSSTSY

MDLSTLTSDD SAVYYCTRHG YYRSDGFDYW GQGTTLTVSS

SEQ ID NO: 20
V_L (mAb 30.4.33):
DIVLTQSPTI MSASPGEKVT MTCRASSSVS SSSLHWYQQK

PGSSPKLWIY STSTLASGVP ARFSGSGSGT SYSLTISGVE

TEDAATYYCQ QYGTSPYTFG SGTKVDIK

SEQ ID NO: 21
V_H (mAb 7.2.32):
EFEVQLQESG GGLVQPKGSL QLSCAASGFT FNTYAMHWVR

QAPGKGLEWV ARIRTESSDY ATDYADSVKD RFIISRDDSQ

NMLYLQMNNL KSEDTAIYYC VRSSGFDYWG QGTTLTVSSS

SEQ ID NO: 22
V_L (mAb 7.2.32):
DIQMTQSPSL PVSLGDQASI SCRSSQSLVH DNGNTYLHWF

LQKPGQSPKL LIYKVSNRFS GVPDRFGGSG SGTDFTLKIS

GVEAEDLGVY FCSQGTHVPT FGGGTKLEIK

SEQ ID NO: 23
V_H (mAb 4.1.15):
EFEVQLQESG PELVKPGTSV TISCKTSGYA FSNSWMSWVK

QRPGQGLEWI GRIFPGNGDT DYNGNFRAKA TLTADKSSST

AFMQLSRLTS VDSAVYFCAR SRGLRQGAGF AYWGQGTLVT VSA

SEQ ID NO: 24
V_L (mAb 4.1.15):
DIVMTQSPSS LAMSVGQKAT MSCKSSQSLL NSSTQRNYLA

WYQQKPGQSP KLLVYFASTR ESGVPDRFIG SGSGTDFTLT

ISSVQAEDLA AYFCQQHYSN PRTFGGGTKL EIK
```

Sequences of ssDNA
a) 19mer ssDNA (covalently bound with 3' end to Fab' of anti-TroponinT MAB b or Fab' 8.1.2 to phosphorylated IGF-1R, respectively): 5'-A GTC TAT TAA TGC TTC TGC-3'(SEQ ID NO:5)
b) 17mer ssDNA (covalently bound with 5' end to Fab' of anti-TroponinT MAB a or Fab' 1.4.168 to IGF-1R, respectively): 5'-AGT TCT ATC GTC GTC CA-3'(SEQ ID NO:6)
c) complementary 19mer ssDNA (used as part of a linker): 5'-G CAG AAG CAT TAA TAG ACT-3'(SEQ ID NO:7)
d) complementary 17mer ssDNA (used as part of a linker): 5'-TGG ACG ACG ATA GAA CT-3' (SEQ ID NO:8)

Sequences of Troponin T Epitopes
SEQ ID NO:9=ERAEQQRIRAEREKEUUSLKDRIEKRR-RAERAEamide, wherein U represents ß-Alanin. (The epitope "A" for antibody anti-Troponin antibody a.)
SEQ ID NO:10=SLKDRIERRRAERAEOOERAEQQRI-RAEREKEamide, wherein O represents Amino-trioxa-octanoic-acid. (The epitope "B" for antibody anti-Troponin antibody b.)

```
Sequences of IGF-1R/IR epitopes
SEQ ID NO: 11 = FDERQPYAHMNGGRKNERALPLPQSST;
IGF-1R (1340-1366)
```

-continued
SEQ ID NO: 12 = YEEHIPYTHMNGGKKNGRILTLPRSNPS;
hIR (1355-1382)

Protein linker and tag-sequences
SEQ ID NO: 13 = GGGGS (=G4S) motif
(e.g. as part of a
polypeptide linker)

SEQ ID NO: 14 = YPYDVPDYA (HA-Tag)

SEQ ID NO: 15 = GLNDIFEAQKIEWHE (Avi-Tag)

SEQ ID NO: 16 = LPETGGGSGS (Sortase Cleavage Tag)

Sequences of HER3 epitopes
SEQ ID NO: 17 = PLHPVPIMPTAGTTPDEDYEYMNRQR;
hHER3 (1242-1267)

SEQ ID NO: 18 = PASEQGYEEMRAF; hHER3 (1283-1295)

Sequences of ssDNA for Sortase-mediated Fab
Labeling
SEQ ID NO: 25 = 5'-(Gly)$_2$-Aminolinker-(Spacer C3)3-
AGT TCT ATCGTC GTC CA-Fluorescein-3'(17mer-Oligo)

SEQ ID NO: 26 = 5'-Fluorescein-AGT CTA TTA ATG CTT
CTG C-(Spacer C3)3-Aminolinker-'-(Gly)$_2$-3'
(19mer-Oligo)

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

The present embodiment relates to a bivalent binding agent binding a posttranslationally modified target polypeptide the binding agent consisting of two monovalent binders that are linked to each other via a linker, wherein a) the first monovalent binder binds to a polypeptide epitope of said target polypeptide, b) the second monovalent binder binds to a posttranslational polypeptide modification, c) each monovalent binder has a Kdiss in the range of $5 \times 10^{-3}$/sec to $10^{-4}$/sec, and d) wherein the bivalent binding agent has a Kdiss of $3 \times 10^{-5}$/sec or less.

As disclosed herein, it has surprisingly been found that a posttranslationally modified target polypeptide can be detected by a bivalent binding agent consisting of two monovalent binders that are linked to each other via a linker, wherein the first monovalent binder binds to a polypeptide epitope of said target polypeptide, the second monovalent binder binds to a posttranslational polypeptide modification, wherein each monovalent binder has a Kdiss in the range of $5 \times 10^{-3}$/sec to $10^{-4}$/sec, and wherein the bivalent binding agent has a Kdiss of $3 \times 10^{-5}$/sec or less The bivalent binding agent according to the present disclosure is a binding agent comprising exactly two monovalent binders of different specificity.

In one embodiment the kinetic rate properties of each monovalent binder and of the bivalent binding agent are characterized by BIACORE™ SPR technology as described in detail in the examples.

As the skilled artisan will appreciate the bivalent binding agent described in the present embodiment can be isolated and purified as desired. In one embodiment the present embodiment relates to an isolated bivalent binding agent as disclosed herein. An "isolated" bivalent binding agent is one which has been identified and separated and/or recovered from e.g. the reagent mixture used in the synthesis of such bivalent binding agent. Unwanted components of such reaction mixture are e.g. monovalent binders that did not end up in the desired bivalent binding agent. In one embodiment, the bivalent binding agent is purified to greater than 80%. In some embodiments, the bivalent binding agent is purified to greater than 90%, 95%, 98% or 99% by weight, respectively. In case both monovalent binders are polypeptides purity is e.g. easily determined by SDS-PAGE under reducing or nonreducing conditions using, for example, Coomassie blue or silver stain in protein detection. In case purity is assessed on the nucleic acid level, size exclusion chromatography is applied to separate the bivalent binding agent from side products and the OD at 260 nm is monitored to assess its purity.

The articles "a" and "an" are used herein to refer to one or to more than one (i.e., to at least one) of the grammatical object of the article. By way of example, "an antibody" means one antibody or more than one antibody.

The term "oligonucleotide" or "nucleic acid sequence" as used herein, generally refers to short, generally single stranded, polynucleotides that comprise at least 8 nucleotides and at most about 1000 nucleotides. In an exemplary embodiment an oligonucleotide will have a length of at least 9, 10, 11, 12, 15, 18, 21, 24, 27 or 30 nucleotides. In an exemplary embodiment an oligonucleotide will have a length of no more than 200, 150, 100, 90, 80, 70, 60, 50, 45, 40, 35 or 30 nucleotides. The description given below for polynucleotides is equally and fully applicable to oligonucleotides.

The term oligonucleotide is to be understood broadly and includes DNA and RNA as well as analogs and modification thereof.

An oligonucleotide may for example contain a substituted nucleotide carrying a substituent at the standard bases deoxyadenosine (dA), deoxyguanosine (dG), deoxycytosine (dC), deoxythymidine (dT), deoxyuracil (dU). Examples of such substituted nucleobases are: 5-substituted pyrimidines like 5 methyl dC, aminoallyl dU or dC, 5-(aminoethyl-3-acrylimido)-dU, 5-propinyl-dU or -dC, 5 halogenated -dU or -dC; N substituted pyrimidines like N4-ethyl-dC; N substituted purines like N6-ethyl-dA, N2-ethyl-dG; 8 substituted purines like 8-[6-amino)-hex-1-yl]-8-amino-dG or -dA, 8 halogenated dA or dG, 8-alkyl dG or dA; and 2 substituted dA like 2 amino dA.

An oligonucleotide may contain a nucleotide or a nucleoside analog. I.e. the naturally occurring nucleobases can be exchanged by using nucleobase analogs like 5-Nitroindol d riboside; 3 nitro pyrrole d riboside, deoxyinosine (dI), deoxyxanthosine (dX); 7 deaza -dG, -dA, -dI or -dX; 7-deaza-8-aza -dG, -dA, -dI or -dX; 8-aza -dA, -dG, -dI or -dX; d Formycin; pseudo dU; pseudo iso dC; 4 thio dT; 6 thio dG; 2 thio dT; iso dG; 5-methyl-iso-dC; N8-linked 8-aza-7-deaza-dA; 5,6-dihydro-5-aza-dC; and etheno-dA or pyrollo-dC. As obvious to the skilled artisan, the nucleobase in the complementary strand has to be selected in such manner that duplex formation is specific. If, for example, 5-methyl-iso-dC is used in one strand (e.g. (a)) iso dG has to be in the complementary strand (e.g. (a')).

The oligonucleotide backbone may be modified to contain substituted sugar residues, sugar analogs, modifications in the internucleoside phosphate moiety, and/or be a PNA.

An oligonucleotide may for example contain a nucleotide with a substituted deoxy ribose like 2'-methoxy, 2'-fluoro, 2'-methylseleno, 2'-allyloxy, 4'-methyl dN (wherein N is a nucleobase, e.g., A, G, C, T or U).

Sugar analogs are for example Xylose; 2',4' bridged Ribose like (2'-O, 4'-C methylene)-(oligomer known as LNA) or (2'-O, 4'-C ethylene)-(oligomer known as ENA); L-ribose, L-d-ribose, hexitol (oligomer known as HNA); cyclohexenyl (oligomer known as CeNA); altritol (oligomer known as ANA); a tricyclic ribose analog where C3' and C5' atoms are connected by an ethylene bridge that is fused to a cyclopropane ring (oligomer known as tricycloDNA); glycerin (oligomer known as GNA); Glucopyranose (oligomer known as Homo DNA); carbaribose (with a cyclopentan instead of a tetrahydrofuran subunit); hydroxymethyl-morpholin (oligomers known as morpholino DNA).

A great number of modification of the internucleosidic phosphate moiety are also known not to interfere with hybridization properties and such backbone modifications can also be combined with substituted nucleotides or nucleotide analogs. Examples are phosphorthioate, phosphordithioate, phosphoramidate and methylphosphonate oligonucleotides.

PNA (having a backbone without phosphate and d-ribose) can also be used as a DNA analog.

The above mentioned modified nucleotides, nucleotide analogs as well as oligonucleotide backbone modifications can be combined as desired in an oligonucleotide in the sense of the present embodiment.

The terms "polypeptide" and "protein" are used interchangeably. A polypeptide in the sense of the present embodiment consists of at least 5 amino acids linked by alpha amino peptidic bonds.

A "target polypeptide" is a polypeptide of interest for which a method for determination or measurement is sought. The target polypeptide of the present embodiment is a polypeptide known or suspected to carry a posttranslational polypeptide modification.

A "monovalent binder" according to the present embodiment is a molecule interacting with the target polypeptide at a single binding site with a Kdiss of $5 \times 10^{-3}$/sec to $10^{-4}$/sec. The biophysical characterization of kinetic binding rate properties, respectively the determination of the dissociation rate constant kd(1/s) according to a Langmuir model is, according to some embodiments, analyzed by biosensor-based surface plasmon resonance spectroscopy. In some embodiments the BIACORE™ technology as described in detail in the Examples section is used.

Examples of monovalent binders are peptides, peptide mimetics, aptamers, spiegelmers, darpins, lectines, ankyrin repeat proteins, Kunitz type domains, single domain antibodies, (see: Hey, T. et al., Trends Biotechnol 23 (2005) 514-522) and monovalent fragments of antibodies.

In certain embodiments the monovalent binder is a monovalent antibody fragment, for example a monovalent fragment derived from a monoclonal antibody.

Monovalent antibody fragments include, but are not limited to Fab, Fab'-SH (Fab'), single domain antibody, Fv, and scFv fragments, as provided below.

In an exemplary embodiment at least one of the monovalent binders is a single domain antibody, an Fab-fragment or an Fab'-fragment of a monoclonal antibody.

It also represents an exemplary embodiment that in the bivalent binding agent disclosed herein both the monovalent binders are derived from monoclonal antibodies and are Fab-fragments, or Fab'-fragments or an Fab-fragment and an Fab'-fragment.

Monoclonal antibody techniques allow for the production of extremely specific binding agents in the form of specific monoclonal antibodies or fragments thereof. Particularly well known in the art are techniques for creating monoclonal antibodies, or fragments thereof, by immunizing mice, rabbits, hamsters, or any other mammal with a polypeptide of interest. Another method of creating monoclonal antibodies, or fragments thereof, is the use of phage libraries of sFv (single chain variable region), specifically human sFv. (See e.g., Griffiths et al., U.S. Pat. No. 5,885,793; McCafferty et al., WO 92/01047; Liming et al., WO 99/06587).

Antibody fragments may be generated by traditional means, such as enzymatic digestion or by recombinant techniques. For a review of certain antibody fragments, see Hudson, P. J. et al., Nat. Med. 9 (2003) 129-134.

An Fv is a minimum antibody fragment that contains a complete antigen-binding site and is devoid of constant region. In one embodiment, a two-chain Fv species consists of a dimer of one heavy- and one light-chain variable domain in tight, non-covalent association. In one embodiment of a single-chain Fv (scFv) species, one heavy- and one light-chain variable domain can be covalently linked by a flexible peptide linker such that the light and heavy chains can associate in a dimeric structure analogous to that in a two-chain Fv species. For a review of scFv, see, e.g., Plueckthun, In: The Pharmacology of Monoclonal Antibodies, Vol. 113, Rosenburg and Moore (eds.), Springer-Verlag, New York (1994), pp. 269-315; see also WO 93/16185; and U.S. Pat. Nos. 5,571,894 and 5,587,458. Generally, six hyper variable regions (HVRs) confer antigen-binding specificity to an antibody. However, even a single variable domain (or half of an Fv comprising only three HVRs specific for an antigen) has the ability to recognize and bind antigen.

An Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group.

Various techniques have been developed for the production of antibody fragments. Traditionally, antibody fragments were derived via proteolytic digestion of intact antibodies (see, e.g., Morimoto, K. et al., Journal of Biochemical and Biophysical Methods 24 (1992) 107-117; and Brennan et al., Science 229 (1985) 81-83). For example, papain digestion of antibodies produces two identical antigen-binding fragments, called "Fab" fragments, each with a single antigen-binding site, and a residual "Fc" fragment, whose name reflects its ability to crystallize readily.

Antibody fragments can also be produced directly by recombinant host cells. Fab, Fv and scFv antibody fragments can all be expressed in and secreted from E. coli, thus allowing the facile production of large amounts of these fragments. Antibody fragments can be isolated from the antibody phage libraries according to standard procedures. Alternatively, Fab'-SH fragments can be directly recovered from E. coli (Carter, P. et al., Bio/Technology 10 (1992) 163-167). Mammalian cell systems can be also used to express and, if desired, secrete antibody fragments.

In certain embodiments, a monovalent binder of the present embodiment is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

One of the two monovalent binders, the first monovalent binder, binds to a polypeptide epitope on the target polypeptide.

A "polypeptide epitope" according to the present embodiment—the binding site on the target polypeptide bound by the corresponding monovalent binder—is composed of amino acids. This binder either binds to a linear epitope, i.e. an epitope consisting of a stretch of 5 to 12 consecutive amino acids, or the monovalent binder binds to a tertiary structure formed by the spatial arrangement of several short stretches of the target polypeptide. Tertiary epitopes recognized by a binder, e.g. by the antigen recognition site or paratope of an antibody, can be thought of as three-dimensional surface features of an antigen molecule; these features fit precisely (in)to the corresponding binding site of the binder and thereby binding between binder and target polypeptide is facilitated.

Whereas in bivalent binding agent as disclosed herein the first monovalent binder binds to a polypeptide epitope the second monovalent binder binds to a posttranslational polypeptide modification.

A "posttranslational polypeptide modification" is a covalent modification of an amino acid within or at the end of a polypeptide (protein). The terms secondary modification and post-translational modification are inter-changeable.

Many types of co-valent amino acid modifications are known and have been subject to scientific review articles. The posttranslational modifications described in the review articles by Mann and Jensen (2003) and by Seo and Lee (2004) are herewith included by reference (Mann, M. and Jensen, O. N., Nat. Biotechnol. 21 (2003) 255-261; Seo, J. and Lee, K.-J., Biochem. Mol. Biol. 37/1 (2004) 35-44).

In an exemplary embodiment the posttranslational modification is selected from the group consisting of acetylation, phosphorylation, acylation, methylation, glycosylation, ubiquitinylation, sumoylation, sulfatation and nitration.

Acetylation (+42 Da) is a rather stable secondary modification. Examples are the acetylation which is found on the N-termini of many proteins or the acetylation on lysine or serine residues. Usually acetylation of a lysine residue is found at one or more well-defined position(s) within a polypeptide chain, while other lysine residues are acetylated less frequently or not at all.

Phosphorylation and de-phosphorylation (the net balance of which may be referred to as phosphorylation status) of a protein is known to be one of the key elements in regulating a proteins biological activity. A low percentage of phosphorylated amino acid residues may already be sufficient to trigger a certain biological activity. Phosphorylation results in a mass increase of 80 Da. The amino acids tyrosine (Y), serine (S), threonine (T), histidine (H), and aspartic acid (D) can be phosphorylated. The more complex the biological function of a polypeptide the more complex the corresponding pattern of possible sites of phosphorylation. This is especially known and true for membrane-bound receptors, especially the so-called receptor tyrosine kinases (RTKs). As the nomenclature already suggests, at least part of the intracellular signaling of the RTKs is mediated by the phosphorylation status of certain tyrosine of the intracellular domain of such RTKs.

Polypeptides may be acylated by farnesyl, myristoyl or palmitoyl groups. Acylation usually occurs on the side chain of a cysteine residue.

Methylation as a secondary modification occurs via the side chain of a lysine residue. It has been shown that the binding properties of regulatory proteins that are able to bind to a nucleic acid can e.g. be modulated via methylation.

Glycosylation is a very important secondary modification. It has a major influence on protein-protein interactions, on solubilization of proteins, their stability, aso. Two different types of glycosylation are known: the N-linked (via the amino acid N (asparagine)) side chains and the O-linked side chains (via serine (S) or threonine (T)). Many different polysaccharides (linear or with branched side chains), some containing sugar derivatives like O-Glc-NAc, have been identified.

Ubiquitinylation and sumoylation, respectively, are known to influence the half-life of proteins in the circulation. Ubiquitinylation may serve as a destruction signal, resulting in cleavage and/or removal of ubiquitinylated polypeptides.

Sulfatation via a tyrosine residue (Y) appears to be important in the modulation of protein-protein (cell-cell) interaction as well as in protein ligand-interaction.

Nitration of tyrosine residues (Y) appears to be a hallmark of oxidative damage as e.g. in inflammatory processes.

The posttranslational modification bound by the second monovalent binder may be selected from the group consisting of phosphorylation, glycosylation and acetylation.

As mentioned above, phosphorylation, de-phosphorylation and phosphorylation statuses are key to the regulation of cell signaling and protein activity. This is especially known and true for membrane-bound receptors, especially the so-called receptor tyrosine kinases (RTKs). As the nomenclature already suggests, at least part of the intracellular signaling of the RTKs is mediated by the phosphorylation status of certain tyrosine of the intracellular domain of such RTKs. In one embodiment the present embodiment thus relates to a bivalent binding agent binding to a phosphorylated target protein. Obviously such bivalent binding agent is of great utility in the detection of a phosphorylated target polypeptide.

In an exemplary embodiment the present embodiment relates to a bivalent binding agent as disclosed herein above, wherein the target polypeptide is selected from the group consisting of membrane-bound receptor molecules having an intracellular phosphorylation site and intracellular cell signaling molecules. In such bivalent binding agent the first monovalent binder, binding a polypeptide epitope on the target protein will be specifically binding said receptor molecule or said intracellular cell signaling molecule, whereas the second monovalent binder targeting phosphorylation does not need to specifically bind a phosphorylation site on said target protein. Cross-reactivity with a phosphorylation site on e.g. a related receptor would not impair the specific detection of the target polypeptide, because significant binding requires the both, the binding of the first and the binding of the second monovalent binder.

In some embodiments, the RTK is selected from the group consisting of: ALK, adhesion related kinase receptor (e.g., Axl), ERBB receptors (e.g., EGFR, ERBB2, ERBB3, ERBB4), erythropoietin-producing hepatocellular (EPH) receptors (e.g., EphA1; EphA2, EphA3, EphA4, EphA5, EphA6, EphA7, EphA8, EphB1, EphB2, EphB3, EphB4, EphB5, EphB6), fibroblast growth factor (FGF) receptors (e.g., FGFR1, FGFR2, FGFR3, FGFR4, FGFR5), Fgr, IGFIR, Insulin R, LTK, M-CSFR, MUSK, platelet-derived growth factor (PDGF) receptors (e.g., PDGFR-A, PDGFR-B), RET, ROR1, ROR2, ROS, RYK, vascular endothelial growth factor (VEGF) receptors (e.g., VEGFR1/FLT1, VEGFR2/FLK1, VEGF3), tyrosine kinase with immunoglobulin-like and EGF-like domains (TIE) receptors (e.g., TIE-1, TIE-2/TEK), Tec, TYRO10, insulin-like growth factor (IGF) receptors (e.g., INS-R, IGF-IR, IR-R), Discoidin Domain (DD) receptors (e.g., DDR1, DDR2), receptor for c-Met (MET), recepteur d'origine nantais (RON); also known as macrophage stimulating 1 receptor, Flt3 fins-related tyrosine kinase 3 (Flt3), colony stimulating factor 1 (CSF1) receptor, receptor for c-kit (KIT, or SCFR) and insulin receptor related (IRR) receptors.

In some embodiments the intracellular cell signaling molecule is selected from the group consisting of: AKT, abl, cbl, erbA, ERK, fes, fgr, fms, fos, jun, met, myb, myc, PI3K, raf, ret, ryk, and src. In an exemplary embodiment the present embodiment relates to a bivalent binding agent binding a posttranslationally modified target polypeptide consisting of two monovalent binders that are linked to each other via a linker, wherein a) the first monovalent binder binds to a polypeptide epitope of said target polypeptide, b) the second monovalent binder binds to a posttranslational polypeptide modification, c) each monovalent binder has a Kdiss in the range of $5 \times 10^{-3}$/sec to $10^{-4}$/sec, d) wherein the bivalent binding agent has a Kdiss of $3 \times 10^{-5}$/sec or less and wherein the posttranslational modification is selected from the group consisting of phosphorylation, ubiquitinylation and glycosylation.

In an exemplary embodiment the kinetic rate properties of each monovalent binder and of the bivalent binding agent are characterized by BIACORE™ SPR technology as described in detail in the examples.

In an exemplary embodiment the bivalent binding agent according to the present embodiment will bind to a target polypeptide having a posttranslational modification, wherein the posttranslational modification is phosphorylation.

As discussed a monovalent binder for use in the construction of a bivalent binding agent as disclosed herein has to have a Kdiss from $5 \times 10^{-3}$/sec to $10^{-4}$/sec.

According to some embodiments, the first monovalent binder is specifically binding to a polypeptide epitope. I.e. this binder binds to an epitope that is either not subject to a secondary modification or in the alternative it specifically binds to the native (non-secondarily modified) epitope. Specific binding to a polypeptide epitope is acknowledged if said binder has a Kdiss that is at least 20 times lower for the non-posttranslationally modified polypeptide as compared to the same polypeptide carrying a posttranslational modification. Also in some embodiments the Kdiss of the first monovalent binder to the non-modified polypeptide is at least 30-, 40-, 50-, 80-, 90-, 95- or at least 100-fold higher as compared to the same polypeptide carrying a posttranslational modification in the polypeptide epitope bound by the first monovalent binder.

According to some embodiments, the second monovalent binder is specifically binding to a posttranslational polypeptide modification, i.e., said binder has a Kdiss that is at least 20 times lower for a polypeptide carrying this posttranslational modification as compared to the same non-posttranslationally modified polypeptide. Also, in some embodiments the Kdiss of the second monovalent binder to the polypeptide carrying a posttranslational modification is at least 30-, 40-, 50-, 80-90-, 95- or at least 100-fold lower as compared to same non-modified polypeptide.

As mentioned above the bivalent binding agent according to the present embodiment will have a Kdiss of at most $3 \times 10^{-5}$/sec or lower, i.e. better.

In one embodiment in the bivalent binding agent according to this embodiment each monovalent binder has a Kdiss from $2 \times 10^{-3}$/sec to $10^{-4}$/sec.

In one embodiment in the bivalent binding agent according to this embodiment each monovalent binder has a Kdiss from $10^{-3}$/sec to $10^{-4}$/sec.

The automatic immunohistochemistry staining machines distributed by Ventana Medical Systems Inc. Tucson employ rather stringent washing conditions. An antibody used on the BENCHMARK® analyzer series should have a Kdiss of at most $5 \times 10^{-5}$/sec in order to give a reasonable staining intensity. The better the Kdiss, the better the staining intensity will be. The bivalent binding agent as disclosed herein has a Kdiss of at most $3 \times 10^{-5}$/sec. In a further embodiment the bivalent binding agent as disclosed herein has a Kdiss of $2 \times 10^{-5}$/sec or less or also in some cases of $10^{-5}$/sec or less.

In one embodiment the kinetic rate properties of each monovalent binder and of the bivalent binding agent are characterized by BIACORE™ SPR technology as described in detail in the examples.

The bivalent binding agent according to the present embodiment contains a linker. The linker can either covalently link the two monovalent binders or the linker and the monovalent binders can be bound by two different specific binding pairs a:a' and b:b'.

The linker may for example be composed of appropriate monomers, linked together and to the two monovalent binders by co-valent bonds. In some embodiments the linker will contain sugar moieties, nucleotide moieties, nucleoside moieties and/or amino acids. In certain embodiments the linker will essentially consist of nucleotides, nucleotide analogues or amino acids.

According to some embodiments the linker covalently linking, or binding the two monovalent binders via binding pairs has a length of 6 to 100 nm. Also in some embodiments the linker has a length of 6 to 50 nm or of 6 to 40 nm. In an exemplary embodiment the linker will have a length of 10 nm or longer or of 15 nm or longer. In one embodiment the linker comprised in a bivalent binding agent according to the present embodiment has between 10 nm and 50 nm in length.

The length of non-nucleosidic entities of a given linker (a-S-b) in theory and by complex methods can be calculated by using known bond distances and bond angles of compounds which are chemically similar to the non-nucleosidic entities. Such bond distances are summarized for some molecules in standard text books: CRC Handbook of Chemistry and Physics, 91st edition, 2010-2011, section 9. However, exact bond distances vary for each compound. There is also variability in the bond angles.

It is therefore more practical to use an average parameter (an easy to understand approximation) in such calculation.

In the calculation of a spacer or a linker length the following approximations apply: a) for calculating lengths of nonnucleosidic entities an average bond length of 130 pm with an bond angle of 180° independently of the nature of the linked atoms is used; b) one nucleotide in a single strand is calculated with 500 pm and c) one nucleotide in a double strand is calculated with 330 pm.

The value of 130 pm is based on calculation of the distance of the two terminal carbon atoms of a C(sp3)-C(sp3)-C(sp3) chain with a bond angle of 109° 28' and a distance of 153 pm between two C(sp3) which is approx 250 pm which translates with an assumed bond angle of 180° to and bond distance between two C(Sp3) with 125 pm. Taking in account that heteroatoms like P and S and sp2 and sp1 C atoms could also be part of the spacer the value 130 pm is taken. If a spacer comprises a cyclic structure like cycloalkyl or aryl the distance is calculated in analogous manner, by counting the number of the bonds of said cyclic structure which are part of the overall chain of atoms that are defining the distance As mentioned above, the linker can either covalently link the two monovalent binders or the linker and the monovalent binders can be bound by two different specific binding pairs a:a' and b:b'. Therefore, the bivalent binding agent according to the present embodiment, binding a posttranslationally modified target polypeptide, can be also depicted by the below Formula I:

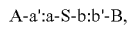

wherein A is a first monovalent binder, binding to a polypeptide epitope of said target polypeptide, wherein B is a second monovalent binder, binding to a posttranslational polypeptide modification, wherein each monovalent binder A and B has a Kdiss in the range of $5 \times 10^{-3}$/sec to $10^{-4}$/sec, wherein a':a as well as b:b' independently are a binding pair or a':a and/or b:b' are covalently bound, wherein a':a and b:b' are different, wherein S is a spacer, wherein — represents a covalent bond, wherein the linker a-S-b has a length of 6 to 100 nm and wherein the bivalent binding agent has a Kdiss of $3 \times 10^{-5}$/sec or less.

The linker L consisting of a-S-b has a length of 6 to 100 nm. In some embodiments the linker L consisting of a-S-b has a length of 6 to 80 nm. In some embodiments the linker has a length of 6 to 50 nm or of 6 to 40 nm. In some embodiments the linker will have a length of 10 nm or longer or of 15 nm in length or longer. In one embodiment the linker has between 10 nm and 50 nm in length. In one embodiment a and b, respectively, are binding pair members and have a length of at least 2.5 nm each.

The spacer S can be construed as required to e.g. provide for the desired length as well as for other desired properties. The spacer can e.g. be fully or partially composed of naturally occurring or non-naturally occurring amino acids, of phosphate-sugar units e.g. a DNA like backbone without nucleobases, of glyco-peptidic structures, or at least partially of saccharide units or at least partially of polymerizable subunits like glycols or acryl amide.

The length of spacer S in a compound according to the present embodiment may be varied as desired. In order to easily make available spacers of variable length, a library, some embodiments may have a simple synthetic access to the spacers of such library. A combinatorial solid phase synthesis of a spacer is possible. Since spacers have to be synthesized up to a length of about 100 nm, the synthesis strategy is chosen in such a manner that the monomeric synthetic building blocks are assembled during solid phase synthesis with high efficiency. The synthesis of deoxy oligonucleotides based on the assembly of phosphoramidite as monomeric building blocks perfectly meet this requirements. In such spacer monomeric units within a spacer are linked in each case via a phosphate or phosphate analog moiety.

The spacer S can contain free positively or/and negatively charged groups of polyfunctional amino-carboxylic acids, e.g. amino, carboxylate or phosphate. For example the charge carriers can be derived from trifunctional aminocarboxylic acids which contain a) an amino group and two carboxylate groups or b) two amino groups and one carboxylate group. Examples of such trifunctional aminocarboxylic acids are lysine, ornithine, hydroxylysine, α,β-diamino propionic acid, arginine, aspartic acid and glutamic acid, carboxy glutamic acid and symmetric trifunctional carboxylic acids like those described in EP-A-0 618 192 or U.S. Pat. No. 5,519,142. Alternatively one of the carboxylate groups in the trifunctional aminocarboxylic acids a) can be replaced by a phosphate, sulphonate or sulphate group. An example of such a trifunctional amino acid is phosphoserine.

The spacer S can also contain uncharged hydrophilic groups. Examples of uncharged hydrophilic groups include ethylene oxide or polyethylene oxide groups with, for example, at least three ethylene oxide units, sulphoxide, sulphone, carboxylic acid amide, carboxylic acid ester, phosphonic acid amide, phosphonic acid ester, phosphoric acid amide, phosphoric acid ester, sulphonic acid amide, sulphonic acid ester, sulphuric acid amide and sulphuric acid ester groups. The amide groups may be primary amide groups, for example carboxylic acid amide residues in amino acid side groups e.g. the amino acids asparagine and glutamine. The esters may be derived from hydrophilic alcohols, such as C1-C3 alcohols or diols or triols.

In one embodiment the spacer S is composed of one type of monomer. For example, the spacer is composed exclusively of amino acids, of sugar residues, of diols, of phospho-sugar units or it can be a nucleic acid, respectively.

In one embodiment, the spacer is DNA. In an exemplary embodiment the spacer is the L-stereoisomer of DNA also known as beta-$_L$-DNA,$_L$-DNA or mirror image DNA. $_L$-DNA features advantages like orthogonal hybridization behaviour, which means that a duplex is formed only between two complementary single strands of L-DNA but no duplex is formed between a single strand of L-DNA and the complementary DNA strand, nuclease resistance and ease of synthesis even of a long spacer. As pointed out ease of synthesis and variability in spacer length are important for a spacer library. Spacers of variable length are extremely utile in identifying the bivalent dual binder according to the present embodiment having a spacer of optimal length thus providing for the optimal distance between the two monovalent binders.

Spacer building blocks, as the name says, can be used to introduce a spacing moiety into the spacer S or to build the spacer S of the linker a-S-b.

Different numbers and kinds of non-nucleotidic as well nucleotidic spacer building blocks are at hand for introducing spacing moieties.

Many different non nucleotidic bifunctional spacer building blocks are known in literature and a great variety is commercially available. The choice of the non nucleotidic bifunctional spacer building is influencing the charge and flexibility of the spacer molecule.

In bifunctional spacer building blocks a hydroxyl group which is protected with an acid labile protecting group is connected to a phosphoramidite group.

Bifunctional spacer building blocks in one embodiment are non-nucleosidic compounds. For example, such spacers are C2-C18 alkyl, alkenyl, alkinyl carbon chains, whereas said alkyl, alkenyl, alkinyl chains may be interrupted by additional ethyleneoxy and/or amide moieties or quarternized cationic amine moieties in order to increase hydrophilicity of the linker. Cyclic moieties like C5-C6-cycloalkyl, C4N, C5N, C4O, C5O-heterocycloalkyl, phenyl which are optionally substituted with one or two C1-C6 alkyl groups can also be used as nonnucleosidic bifunctional spacer moieties. Exemplary bifunctional building blocks comprise C3-C6 alkyl moieties and tri- to hexa-ethyleneglycol chains. Table I shows some examples of nucleotidic bifunctional spacer building blocks with different hydrophilicity, different rigidity and different charges. One oxygen atom is connected to an acid labile protecting group such as dimethoxytrityl and the other is part of a phosphoramidite.

TABLE I
Examples of non-nucleotidic bifunctional spacer building blocks
| Non-nucleotidic bifunctional spacer building blocks | Reference |
|---|---|
|  | Seela, F., Nucleic Acids Research 15 (1987) 3113-3129 |
| 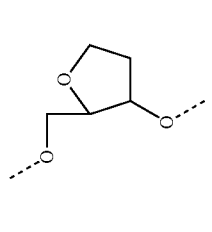 | Iyer, R. P., Nucleic Acids Research 18 (1990) 2855-2859 |
| 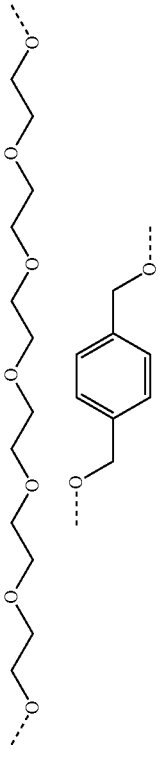 | WO 89/02931 A1 |
| 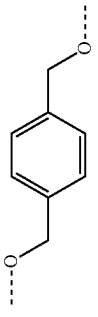 | EP 1 538 221 |

TABLE I-continued

Examples of non-nucleotidic bifunctional spacer building blocks

| Non-nucleotidic bifunctional spacer building blocks | Reference |
| --- | --- |
| (stilbene-based PEG structure) | U.S. 2004/224372 |
| (bis-trifluoroacetamide polyamine structure) | WO 2007/069092 |

A simple way to build the spacer S or to introduce spacing moieties into the spacer S is to use standard D or L nucleoside phosphoramidite building blocks. In one embodiment a single strand stretch of dT is used. This is advantageous, because dT does not carry a base protecting group.

Hybridization can be used in order to vary the spacer length (distance between the binding pair members a and b) and the flexibility of the spacer, because the double strand length is reduced compared to the single strand and the double strand is more rigid than a single strand.

For hybridization in one embodiment oligonucleotides modified with a functional moiety X are used. The oligonucleotide used for hybridization can have one or two terminal extentions not hybridizing with the spacer and/or is branched internally. Such terminal extensions that are not hybridizing with the spacer (and not interfering with the binding pairs a:a' and b:b') can be used for further hybridization events. In one embodiment an oligonucleotide hybridizing with a terminal extension is labeled oligonucleotide. This labeled oligonucleotide again may comprise terminal extensions or being branched in order to allow for further hybridization, thereby a polynucleotide aggregate or dendrimer can be obtained. A poly-oligonucleic acid dendrimer may be used in order to produce a polylabel or in order to get a high local concentration of X.

In one embodiment the spacer S has a backbone length of 1 to 100 nm. With other words here the groups a and b of Formula I are between 1 and 100 nm apart. In one embodiment a and b, respectively, each are a binding pair member and the spacer S has a backbone length of 1 to 95 nm.

"a':a" as well as "b:b'" each independently represent a binding pair or represent covalently bound a':a and/or b:b', respectively.

"a':a" as well as "b:b'" are different. The term different indicates that the binding of a to a' (intra-binding pair-binding or covalent coupling) does not interfere with the intra-binding pair-binding or covalent coupling of the other pair b to b', and vice versa.

In one embodiment either a':a or b:b' are bound covalently and the other, i.e., b:b' or a':a, respectively, represents a binding pair.

In one embodiment both a':a and b:b' are bound covalently.

The coupling chemistry between a':a and b:b' is different from one another and selected from standard protocols. Depending on the nature of the binding partner and of the spacer, appropriate conjugation chemistries are chosen.

The chemistry used in coupling (a') to (a), i.e. in coupling A-(a') to a linker comprising (a) does not interfere with the chemistry used in coupling (b) to (b'), i.e. in coupling (b')-B to a linker comprising (b). As the skilled artisan will appreciate, the reactive sites (a), (a'), (b) and (b'), respectively, leading to the covalent bond a':a as well as b:b', respectively, may also not interfere with any functional group that might be present on a monovalent binder (A and/or B of Formula I).

In case at least one of the monovalent binders is a protein, a peptide or a peptide mimic, it likely carries one or more OH, COOH, NH2 and/or SH groups, which could potentially react with certain coupling reagents. Such (side-) reaction can be avoided by selecting e.g. one of the coupling chemistries given in Table II.

Table II provides an overview over routinely used reactive groups for binding A-(a') and (b')-B, respectively, to (a) and (b), respectively, both being covalently bound to the linker (a-S-b).

TABLE II

| reactive site (a') within A-(a') | reactive site (a) of the linker L: (a)-S-(b) | reactive site (b) of the linker L: (a)-S-(b) | reactive site (b') within (b')-B |
|---|---|---|---|
| ONH2 (aminoxy) | C(H)=O (aldehyde) | —C≡C (alkyne) or triphenylphosphin carboxylic ester | N3 (azide) |
| C(H)=O (aldehyde) | ONH2 (aminoxy) | N3 (azide) | —C≡C (alkyne) or triphenylphosphin carboxylic ester |
| ONH2 (aminoxy) | C(H)=O (aldehyde) | Dien | Dienophil |
| C(H)=O (aldehyde) | ONH2 (aminoxy) | Dienophil | Dien |
| Dien | Dienophil | N3 (azide) | —C≡C (alkyne) or triphenylphosphin carboxylic ester |
| Dienophil | Dien | N3 (azide) | —C≡C (alkyne) or triphenylphosphin carboxylic ester |
| Dienophil | Dien | —C≡C (alkyne) or triphenylphosphin carboxylic ester | N3 (azide) |
| Dien | Dienophil | —C≡C (alkyne) or triphenylphosphin carboxylic ester | N3 (azide) |

The above bi-orthogonal coupling chemistries are e.g. appropriate if at least one of the monovalent binders is a polypeptide. If the two binding partners are not carrying certain reactive functional groups, e.g. in the case of combination of two aptamers, as the monovalent binders A an B, respectively, there is more freedom in selection of the reactive sites (a'), (a), (b) and (b'), respectively. Therefore in addition or in combination with the pairs of corresponding reactive sites given in the above table, amino/active ester (e.g. NHS ester), and SH/SH or SH/maleinimido can be used for orthogonal coupling.

As obvious from the above examples at least one of the covalent bonds between a':a and between b:b', respectively is not an alpha amino peptide bond. Also in some embodiments both covalent bonds are not alpha amino peptide bonds.

In one embodiment both a':a and b:b' are a binding pair. Consequently, in one embodiment the present embodiment relates to an at least bispecific binding agent of the Formula I: A-a':a-S-b:b'-B; wherein A is a first monovalent binder, binding to a polypeptide epitope of a target polypeptide, wherein B is a second monovalent binder, binding to a posttranslational polypeptide modification on a target polypeptide, wherein each monovalent binder A and B has a Kdiss in the range of $5 \times 10^{-3}$/sec to $10^{-4}$/sec, wherein a':a as well as b:b' independently are a binding pair and are different, wherein S is a spacer, wherein—represents a covalent bond, wherein the linker a-S-b has a length of 6 to 100 nm and wherein the bivalent binding agent has a Kdiss of $3 \times 10^{-5}$/sec or less.

In this embodiment a and a' are the members of the binding pair a':a and b and b' are the members of the binding pair b:b', respectively. In some embodiments each member of a binding pair is of a molecular weight of 10 kD or below. In further embodiments the molecular weight of each binder of such binding pair is 8, 7, 6, 5 or 4 kD or below.

In one embodiment a':a and b:b' are binding pairs and the members of the binding pairs a':a and b:b' are selected from the group consisting of leucine zipper domain dimers and hybridizing nucleic acid sequences. In one embodiment both binding pairs represent leucine zipper domain dimers. In one embodiment both binding pairs are hybridizing nucleic acid sequences.

In case a:a' or b':b represents a binding pair, the binding affinity for (within) such binding pair is at least $10^8$ l/mol. Both binding pairs are different. For a binding pair difference is e.g. acknowledged if the affinity for the reciprocal binding, e.g. binding of a as well as a' to b or b' is 10% of the affinity within the pair a:a' or lower. Also in some cases, the reciprocal binding, i.e. binding of a as well as a' to b or b', respectively, is 5% of the affinity within the pair a:a' or lower, or if it is 2% of the affinity within the pair a:a' or lower. In one embodiment the difference is so pronounced that the reciprocal (cross-reactive) binding is 1% or less as compared to the specific binding affinity within a binding pair.

The term "leucine zipper domain" is used to denote a commonly recognized dimerization domain characterized by the presence of a leucine residue at every seventh residue in a stretch of approximately 35 residues. Leucine zipper domains are peptides that promote oligomerization of the proteins in which they are found. Leucine zippers were originally identified in several DNA-binding proteins (Landschulz, W. H. et al., Science 240 (1988) 1759-1764), and have since been found in a variety of different proteins. Among the known leucine zippers are naturally occurring peptides and derivatives thereof that dimerize or trimerize. Examples of leucine zipper domains suitable for producing soluble multimeric proteins are described in PCT application WO 94/10308, and the leucine zipper derived from lung surfactant protein D (SPD) described in Hoppe, H. J. et al., FEBS Lett. 344 (1994) 191-195.

Leucine zipper domains form dimers (binding pairs) held together by an alpha-helical coiled coil. A coiled coil has 3.5 residues per turn, which means that every seventh residue occupies an equivalent position with respect to the helix axis. The regular array of leucines inside the coiled coil stabilizes the structure by hydrophobic and Van der Waals interactions.

If leucine zipper domains form the first binding pair (a':a) and the second binding pair (b:b'), both leucine zipper sequences are different, i.e. sequences a and a' do not bind to b and b'. Leucine zipper domains may be isolated from natural proteins known to contain such domains, such as transcription factors. One leucine zipper domain may e.g. come from the transcription factor fos and a second one from the transcription factor jun. Leucine zipper domains may also be designed and synthesized artificially, using standard techniques for synthesis and design known in the art.

In some embodiments both members of the binding pairs a':a and b:b', i.e. a, a', b and b' represent leucine zipper domains and the spacer S consists of amino acids. In this embodiment production of the construct a-S-b is easily possible. Varying the length of such spacer S as desired is straightforward for a person skilled in the art. Such polypeptide can be synthesized or recombinantly produced.

E.g., recombinant fusion proteins comprising a spacer polypeptide fused to a leucine zipper peptide at the N-terminus and to a leucine zipper peptide at the C-terminus can be expressed in suitable host cells according to standard techniques. A DNA sequence coding for a desired peptide spacer can be inserted between a sequence coding for a member of a first leucine zipper domain a and in the same reading frame a DNA sequence coding for a member of a second leucine zipper domain b.

The spacer S, if the linker a-S-b is a polypeptide in one embodiment comprises once or several times a GGGGS (SEQ ID NO:13) amino acid sequence motif. The spacer S may also comprise a tag sequence. The tag sequence may be selected from commonly used protein recognition tags such as YPYDVPDYA (HA-Tag) (SEQ ID NO:14) or GLN-DIFEAQKIEWHE (Avi-Tag) (SEQ ID NO:15).

In some embodiments both binding pairs (a':a) and (b:b') are hybridizing nucleic acid sequences.

As indicated already by nomenclature, a and a' as well as b and b' hybridize to one another, respectively. The nucleic acid sequences comprised in a and a' one the one hand and in b and b' on the other hand are different. With other words the sequences of in the binding pair a':a do not bind to the sequences of the binding pair b:b', respectively, and vice versa. In one embodiment the present embodiment relates to an at least dual binding agent of Formula I, wherein the binding pairs a:a' and b:b', respectively, both are hybridizing nucleic acid sequences and wherein the hybridizing nucleic acid sequences of the different binding pairs a':a and b:b' do not hybridize with one another. With other words a and a' hybridize to each other but do not bind to any of b or b' or interfere with their hybridization and vice versa. Hybridization kinetics and hybridization specificity can easily be monitored by melting point analyses. Specific hybridization of a binding pair (e.g. a:a') and non-interference (e.g. with b or b') is acknowledged, if the melting temperature for the pair a:a' as compared to any possible combination with b or b', respectively, (i.e. a:b; a:b'; a':b and a':b') is at least 20° C. higher.

The nucleic acid sequences forming a binding pair, e.g. (a:a') or any other nucleic acid sequence-based binding pair, may compromise any naturally occurring nucleobase or an analogue thereto and may have a modified or an un-modified backbone as described above, provided it is capable of forming a stable duplex via multiple base pairing. Stable means that the melting temperature of the duplex is higher than 37° C. The double strand may consist of two fully complementary single strands. However mismatches or insertions are possible as long as the a stability at 37° C. is given.

As the skilled artisan will appreciate a nucleic acid duplex can be further stabilized by interstrand crosslinking. Several appropriate cross-linking methods are known to the skilled artisan, e.g. methods using psoralen or based on thionucleosides.

The nucleic acid sequences representing the members of a binding pair may consist of between 12 and 50 nucleotides. Also such nucleic acid sequences will consist of between 15 and 35 nucleotides.

RNAses are ubiquitous and special care has to be taken to avoid unwanted digestion of RNA-based binding pairs and/or spacer sequences. While it certainly is possible to use, e.g. RNA-based binding pairs and/or spacers, binding pairs and/or spacers based on DNA represent exemplary embodiments.

Appropriate hybridizing nucleic acid sequences can easily be designed to provide for more than two pairs of orthogonal complementary oligonucleotides, allowing for an easy generation and use of more than two binding pairs. Another advantage of using hybridizing nucleic acid sequences in a dual binding agent of the present embodiment is that modifications can be easily introduced into a nucleic acid sequences. Modified building blocks are commercially available which e.g. allow for an easy synthesis of a linker comprising a functional moiety. Such functional moiety can be easily introduced at any desired position and in any of the structures a and a' as well as b and b' and/or S, provided they represent an oligonucleotide.

In some embodiments the spacer S comprised in a binding agent according to Formula I is a nucleic acid. In some embodiments both binding pairs are hybridizing nucleic acid sequences and the spacer S also is a nucleic acid. In this embodiment the linker L consisting of a-S-b is an oligonucleotide.

In case the spacer S as well as the sequences a, a', b and b' all are oligonucleotide sequences it is easily possible to provide for and synthesize a single oligonucleotide representing the linker L comprising S and the members a and b of the binding pairs a':a and b:b', respectively. In case the monovalent binders A and B, respectively, are polypeptides, they can each be coupled easily to the hybridizing nucleic acid sequences a' and b', respectively. The length of the spacer S comprised in such construct can easily be varied in any desired manner. Based on the three constructs a-S-b, A-a' and b'-B the binding agent of Formula I can be most easily obtained according to standard procedures by hybridization between a':a and b:b', respectively. When spacers of different length are used, the resulting constructs, provide for otherwise identical dual binding agents, yet having a different distance in between the monovalent binders A and B. This allows for optimal distance and/or flexibility.

In some embodiments the spacer S as well as the sequences a, a', b and b' are DNA.

The enantiomeric L-DNA, is known for its orthogonal hybridization behavior, its nuclease resistance and for ease of synthesis of oligonucleotides of variable length. This ease of variability in linker length via designing appropriate spacers is important for optimizing the binding of a binding agent as disclosed herein to its antigen or antigens.

In an exemplary embodiment the linker L (=a-S-b) is enantiomeric L-DNA or L-RNA. In an embodiment linker a-S-b is enantiomeric L-DNA. In an embodiment a, a', b and b' as well as the spacer S are enantiomeric L-DNA or L-RNA. In an embodiment a, a', b and b' as well as the spacer S are enantiomeric L-DNA.

In one embodiment the spacer S is an oligonucleotide and is synthesized in two portions comprising ends hybridizable with each other. In this case the spacer S can be simply constructed by hybridization of these hybridizable ends with one another. The resulting spacer construct comprises an oligonucleotide duplex portion. As obvious, in case the spacer is construed that way, the sequence of the hybridizable oligonucleotide entity forming said duplex is chosen in such a manner that no hybridization or interference with the binding pairs a:a' and b:b' can occur.

As already described above the monovalent specific binders A and B of Formula I may be nucleic acids. In one embodiment of the present embodiment a', a, b, b', A, B and S all are oligonucleotide sequences. In this embodiment the sub-units A-a', a-S-b and b'-B of Formula I can easily and independently be synthesized according to standard procedures and combined by hybridization according to convenient standard procedures.

As discussed in detail above, the coupling can be either co-valent or it can be via specific binding pairs.

As the skilled artisan will readily appreciate, the bivalent binding agent according to the present embodiment may be further modified to carry one or more functional moieties. Such functional moiety X may be selected from the group consisting of a binding group, a labeling group, an effector group and a reactive group.

If more than one functional moiety X is present, each such functional moiety can in each case be independently a binding group, a labeling group, an effector group or a reactive group.

In one embodiment the functional moiety X may be selected from the group consisting of a binding group, a labeling group and an effector group.

In one embodiment the group X is a binding group. As obvious to a person skilled in the art, the binding group X will be selected to have no interference with the pairs a':a and b:b'.

Examples of binding groups are the partners of a bioaffine binding pair which can specifically interact with the other partner of the bioaffine binding pair. Suitable bioaffine binding pairs are hapten or antigen and antibody; biotin or biotin analogues such as aminobiotin, iminobiotin or desthiobiotin and avidin or streptavidin; sugar and lectin, oligonucleotide and complementary oligonucleotide, receptor and ligand, e.g., steroid hormone receptor and steroid hormone. In one embodiment X is a binding group and is covalently bound to at least one of a', a, b, b' or S of the compound of Formula I. In some embodiments, the smaller partner of a bioaffine binding pair, e.g. biotin or an analogue thereto, a receptor ligand, a hapten or an oligonucleotide is covalently bound to at lest one of a', a, L, b or b' as defined above.

In one embodiment functional moiety X is a binding group selected from hapten; biotin or biotin analogues such as aminobiotin, iminobiotin or desthiobiotin; oligonucleotide and steroid hormone.

In one embodiment the functional moiety X is a reactive group. The reactive group can be selected from any known reactive group, like Amino, Sulfhydryl, Carboxylate, Hydroxyl, Azido, Alkinyl or Alkenyl. In one embodiment the reactive group is selected from Maleinimido, Succinimidyl, Dithiopyridyl, Nitrophenylester, Hexafluorophenylester.

In one embodiment the functional moiety X is a labeling group. The labeling group can be selected from any known detectable group. The skilled artisan will choose the number of labels as appropriate for best sensitivity with least quenching.

The labeling group can be selected from any known detectable group. In one embodiment the labeling group is selected from dyes like luminescent labeling groups such as chemiluminescent groups e.g. acridinium esters or dioxetanes or fluorescent dyes e.g. fluorescein, coumarin, rhodamine, oxazine, resorufin, cyanine and derivatives thereof, luminescent metal complexes such as ruthenium or europium complexes, enzymes as used for CEDIA (Cloned Enzyme Donor Immunoassay, e.g. EP 0 061 888), microparticles or nanoparticles e.g. latex particles or metal sols, and radioisotopes.

In one embodiment the labeling group is a luminescent metal complex and the compound has a structure of the general formula (II):

$$[M(L_1L_2L_3)]_n\text{-}Y\text{-}X_mA \qquad (II)$$

in which M is a divalent or trivalent metal cation selected from rare earth or transition metal ions, $L_1$, $L_2$ and $L_3$ are the same or different and denote ligands with at least two nitrogen-containing heterocycles in which $L_1$, $L_2$ and $L_3$ are bound to the metal cation via nitrogen atoms, X is a reactive functional group which is covalently bound to at least one of the ligands $L_1$, $L_2$ and $L_3$ via a linker Y, n is an integer from 1 to 10, for example 1 to 4, m is 1 or 2 and A denotes the counter ion which may be required to equalize the charge.

The metal complex may be a luminescent metal complex i.e. a metal complex which undergoes a detectable luminescence reaction after appropriate excitation. The luminescence reaction can for example be detected by fluorescence or by electrochemiluminescence measurement. The metal cation in this complex is for example a transition metal or a rare earth metal. The metal may be ruthenium, osmium, rhenium, iridium, rhodium, platinum, indium, palladium, molybdenum, technetium, copper, chromium or tungsten. Ruthenium, iridium, rhenium, chromium and osmium are utilized according to some embodiments.

The ligands $L_1$, $L_2$ and $L_3$ are ligands with at least two nitrogen-containing heterocycles. Aromatic heterocycles such as bipyridyl, bipyrazyl, terpyridyl and phenanthrolyl may be utilized. The ligands $L_1$, $L_2$ and $L_3$ may be selected from bipyridine and phenanthroline ring systems.

The complex can additionally contain one or several counter ions A to equalize the charge. Examples of suitable negatively charged counter ions are halogenides, $OH^-$, carbonate, alkylcarboxylate, e.g. trifluoroacetate, sulphate, hexafluorophosphate and tetrafluoroborate groups. Hexafluorophosphate, trifluoroacetate and tetrafluoroborate groups may be used. Examples of suitable positively charged counter ions are monovalent cations such as alkaline metal and ammonium ions.

In a further embodiment the functional moiety X is an effector group. An effector group is a therapeutically active substance.

Therapeutically active substances have different ways in which they are effective, e.g. in inhibiting cancer. They can damage the DNA template by alkylation, by cross-linking, or by double-strand cleavage of DNA. Other therapeutically active substances can block RNA synthesis by intercalation. Some agents are spindle poisons, such as vinca alkaloids, or anti-metabolites that inhibit enzyme activity, or hormonal and anti-hormonal agents. The effector group X may be selected from alkylating agents, antimetabolites, antitumor antibiotics, vinca alkaloids, epipodophyllotoxins, nitrosoureas, hormonal and antihormonal agents, and toxins.

Currently other alkylating agents may be exemplified by cyclophosphamide, chlorambucil, busulfan, Melphalan, Thiotepa, ifosphamide, Nitrogen mustard.

Currently antimetabolites may be exemplified by methotrexate, 5-Fluorouracil, cytosine arabinoside, 6-thioguanine, 6-mercaptopurin.

Currently antitumor antibiotics may be exemplified by doxorubicin, daunorubicin, idorubicin, nimitoxantron, dactinomycin, bleomycin, mitomycin, and plicamycin.

Currently spindle poisons may be exemplified by maytansine and maytansinoids, vinca alkaloids and epipodophyllotoxins may be exemplified by vincristin, vinblastin, vindestin, Etoposide, Teniposide.

Currently nitrosoureas may be exemplified by carmustin, lomustin, semustin, streptozocin.

Currently hormonal and antihormonal agents may be exemplified by adrenocorticorticoids, estrogens, antiestrogens, progestins, aromatase inhibitors, androgens, antiandrogens.

Additional random synthetic agents may be exemplified by dacarbazin, hexamethylmelamine, hydroxyurea, mitotane, procarbazide, cisplastin, carboplatin.

A functional moiety X is bound either covalently or via an additional binding pair, e.g., to at least one of (a'), (a), (b), (b') or S. The functional moiety X can occur once or several (n) times. (n) is an integer and 1 or more than one. In some embodiments (n) is between 1 and 100, for example (n) being 1-50 or in certain embodiments n is 1 to 10, or 1 to 5. In further embodiments n is 1 or 2.

For covalent binding of the functional moiety X to at least one of a', a, b, b' or S any appropriate coupling chemistry can be used. The skilled artisan can easily select such coupling chemistry from standard protocols. It is also possible to incorporate a functional moiety by use of appropriate building blocks when synthesizing a', a, b, b' or S.

In an embodiment functional moiety X is bound to a, b, or S of the binding agent as defined by Formula I.

In another embodiment functional moiety X is bound to the spacer S of the binding agent as defined by Formula I.

In an embodiment functional moiety X is covalently bound to a, b, or S of the binding agent as defined by Formula I.

If a functional moiety X is located within the a hybridizing oligonucleotide representing a, a', b or b', respectively, in some embodiments such functional moiety is bound to a modified nucleotide or is attached to the internucleosidic P atom (WO 2007/059816). Modified nucleotides which do not interfere with the hybridization of oligonucleotides are incorporated into those oligonucleotides. Such modified nucleotides may be C5 substituted pyrimidines or C7 substituted 7deaza purines.

Oligonucleotides can be modified internally or at the 5' or 3' terminus with non-nucleotidic entities which are used for the introduction of functional moiety. In some embodiments such non-nucleotidic entities are located within the spacer S, i.e. between the two binding pair members a and b.

Many different non-nucleotidic modifier building blocks for construction of a spacer are known in literature and a great variety is commercially available. For the introduction of a functional moiety either non-nucleosidic bifunctional modifier building blocks or non-nucleosidic trifunctional modified building blocks are either used as CPG for terminal labeling or as phosphroamidite for internal labeling (see: Wojczewski, C. et al., Synlett 10 (1999) 1667-1678).

Bifunctional Modifier Building Blocks

Bifunctional modifier building blocks connect a functional moiety or a—if necessary—a protected functional moiety to a phosphoramidite group for attaching the building block at the 5' end (regular synthesis) or at the 3'end (inverted synthesis) to the terminal hydroxyl group of a growing oligonucleotide chain.

Bifunctional modifier building blocks may be non-nucleosidic compounds. For example, such modified building blocks are C2-C18 alkyl, alkenyl, alkynyl carbon chains, whereas said alkyl, alkenyl, alkynyl chains may be interrupted by additional ethyleneoxy and/or amide moieties in order to increase hydrophilicity of the spacer and thereby of the whole linker structure. Cyclic moieties like C5-C6-cycloalkyl, C4N, C5N, C4O, C5O-heterocycloalkyl, phenyl which are optionally substituted with one or two C1-C6 alkyl groups can also be used as non-nucleosidic bifunctional modified building blocks. In some embodiments modified bifunctional building blocks comprise C3-C6 alkyl moieties and tri- to hexa-ethyleneglycol chains. Non-limiting, examples of bifunctional modifier building blocks are given in Table III below.

TABLE III

| Bifunctional non-nucleosidic modifier building block | Introduction of | Reference |
|---|---|---|
| ----O~~~~~~~~~~---- (hexyl ether linker) | ----NH-C(=O)-label | Pon, R. T., Tetrahedron Letters 32 (1991) 1715-1718 |
|  | ----NH-C(=O)-CF(F)-F (trifluoro amide) | Theisen, P. et al., Nucleic Acids Symposium Series (1992), 27 (Nineteenth Symposium on Nucleic Acids Chemistry, 1992), 99-100 EP 0 292 128 |
| ----O~~~~~~~~---- (hexyl diether) | ----S-S~~~~~~O~ | EP 0 523 978 |
| ----O~~~---- (propyl ether) | ----C≡CH (alkyne) | Meyer, A., et al., Journal of Organic Chemistry 75 (2010) 3927-3930 |
| ----O-(cyclohexyl)-NH-C(=O)-C(=O)-NH-CH$_2$CH$_2$CH$_2$-O-CH$_2$CH$_2$-O-CH$_2$CH$_2$-O-propyl---- | ----NH-C(=O)-label | Morocho, A. M. et al., Nucleosides, Nucleotides & Nucleic Acids 22 (2003) 1439-1441 |
| ----O-CH$_2$CH$_2$-(phenyl)---- | ----NH-C(=O)-label | Cocuzza, A. J., Tetrahedron Letters 30 (1989) 6287-6290 |

Trifunctional Modifier Building Blocks

Trifunctional building blocks connect (i) a functional moiety or a—if necessary—a protected functional moiety, (ii) a phosphoramidite group for coupling the reporter or the functional moiety or a—if necessary—a protected functional moiety, during the oligonucleotide synthesis to a hydroxyl group of the growing oligonucleotide chain and (iii) a hydroxyl group which is protected with an acid labile protecting group, for example, with a dimethoxytrityl protecting group. After removal of this acid labile protecting group a hydroxyl group is liberated which can react with further phosphoramidites. Therefore trifunctional building blocks allow for positioning of a functional moiety to any location within an oligonucleotide. Trifunctional building blocks are also a prerequisite for synthesis using solid supports, e.g. controlled pore glass (CPG), which are used for 3' terminal labeling of oligonucleotides. In this case, the trifunctional building block is connected to a functional moiety or a—if necessary—a protected functional moiety via an C2-C18 alkyl, alkenyl, alkinyl carbon chains, whereas said alkyl, alkenyl, alkiyinyl chains may be interrupted by additional ethyleneoxy and/or amide moieties in order to increase hydrophilicity of the spacer and thereby of the whole linker structure and comprises a hydroxyl group which is attached via a cleavable spacer to a solid phase and a hydroxyl group which is protected with an acid labile protecting group. After removal of this protecting group a hydroxyl group is liberated which could then react with a phosphoramidite.

Trifunctional building blocks may be non-nucleosidic or nucleosidic.

Non-nucleosidic trifunctional building blocks are C2-C18 alkyl, alkenyl, alkynyl carbon chains, whereas said alkyl, alkenyl, alkynyl are optionally interrupted by additional ethyleneoxy and/or amide moieties in order to increase hydrophilicity of the spacer and thereby of the whole linker structure. Other trifunctional building blocks are cyclic groups like C5-C6-cycloalkyl, C4N, C5N, C4O, C5O heterocycloalkyl, phenyl which are optionally substituted with one ore two C1-C6 alkyl groups. Cyclic and acyclic groups may be substituted with one —(C1-C18)alkyl-O-PG group, whereas said C1-C18 alkyl comprises (Ethyleneoxy)n, (Amide)m moieties with n and m independently from each other=0-6 and PG is an acid labile protecting group. Exemplary trifunctional building blocks are C3-C6 alkyl, cycloalkyl, C5O heterocycloalkyl moieties optionally comprising one amide bond and substituted with a C1-C6 alkyl O-PG group, wherein PG is an acid labile protecting group, for example monomethoxytrityl, dimethoxytrityl, pixyl, xanthyl.

Non-limiting, examples for non-nucleosidic trifunctional building blocks are e.g. summarized in Table IV.

TABLE IV
Examples for non-nucleosidic trifunctional modifier building blocks
| Trifunctional | Introduction of | Reference |
|---|---|---|
| 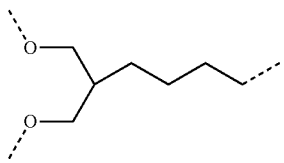 | 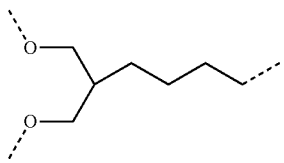 | Nelson, P. S. et al., Nucleic Acids Research 20 (1992) 6253-6259 |
| | 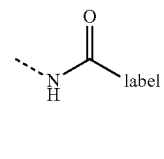 | EP 0 313 219; U.S. Pat. No. 5,585,481; U.S. Pat. No. 5,451,463; EP 0 786 468; WO 92/11388; WO 89/02439 |
| 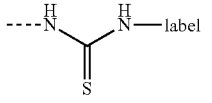 | 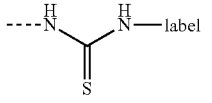 | Su, S. -H, et al., Bioorganic & Medicinal Chemistry Letters 7 (1997) 1639-1644 |
| | 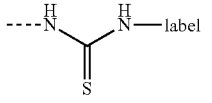 | WO 97/43451 |
|  |  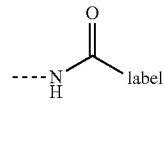 | Putnam, W. C. et al., Nucleosides, Nucleotides & Nucleic Acids 24 (2005) 1309-1323 |
| | 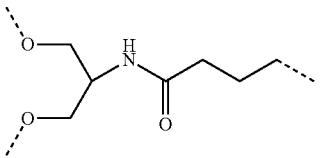 | US 2005/ 214833; EP 1 186 613 |
| 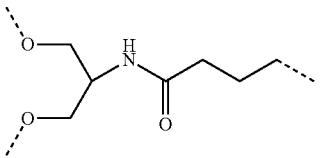 | 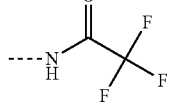 | EP 1 431 298 |
| | 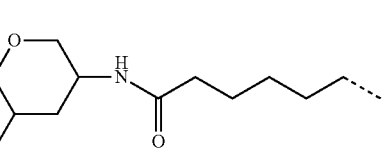 | |
| 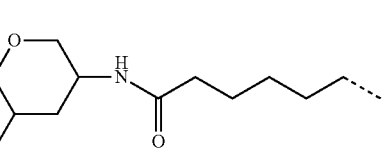 | 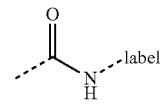 | WO 94/04550 Huynh, V. et al., Nucleic Acids Symposium |

TABLE IV-continued

Examples for non-nucleosidic trifunctional modifier building blocks

| Trifunctional | Introduction of | Reference |
|---|---|---|
| | | Series (1993), 29 (Second International Symposium on Nucleic Acids Chemistry), 19-20 |
| [structure] | ----N---label | WO 2003/019145 |
| [structure] | ----NH-C(=S)-NH----label | Behrens, C. and Dahl, O., Nucleosides & Nucleotides 18 (1999) 291-305<br>WO 97/05156 |
| [structure] | ----NH-C(=O)----label | Prokhorenko, I. A. et al., Bioorganic & Medicinal Chemistry Letters 5 (1995) 2081-2084<br>WO 2003/104249 |
| [structure] | ----NH-C(=O)----label | U.S. Pat. No. 5,849,879 |

Nucleosidic Modifier Building Blocks:

Nucleosidic modifier building blocks are used for internal labeling whenever it is necessary not to influence the oligonucleotide hybridization properties compared to a non-modified oligonucleotide. Therefore nucleosidic building blocks comprise a base or a base analog which is still capable of hybridizing with a complementary base. The general formula of a labeling compound for labeling a nucleic acid sequence of one or more of a, a', b, b' or S comprised in a binding agent according to Formula I of the present embodiment is given in Formula II.

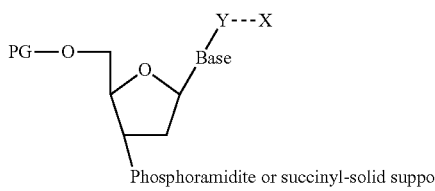

Formula II

Phosphoramidite or succinyl-solid support wherein PG is an acid labile protecting group, such as monomethoxytrityl, dimethoxytrityl, pixyl, xanthyl, wherein Y is C2-C18 alkyl, alkenyl alkinyl, wherein said alkyl, alkenyl, alkinyl may comprise ethyleneoxy and/or amide moieties, wherein Y may be C4-C18 alkyl, alkenyl or alkinyl and contains one amide moiety and wherein X is a functional moiety to which a label can be bound.

Specific positions of the base may be chosen for such substitution to minimize the influence on hybridization properties. Therefore, in some embodiments the following positions for substitution may be: a) with natural bases: Uracil substituted at C5; Cytosine substituted at C5 or at N4; Adenine substituted at C8 or at N6 and Guanine substituted at C8 or at N2 and b) with base analogs: 7 deaza A and 7 deaza G substituted at C7; 7 deaza 8 Aza A and 7 deaza 8 Aza G substituted at C7; 7 deaza Aza 2 amino A substituted at C7; Pseudouridine substituted at N1 and Formycin substituted at N2.

Non-limiting examples for nucleosidic trifunctional building blocks are given in Table V.

TABLE V

| Trifunctional nucleosidic | A | Reference |
|---|---|---|
|  |  | Roget, A. et al., Nucleic Acids Research 17 (1989) 7643-7651<br>WO 89/12642;<br>WO 90/08156;<br>WO 93/05060 |
|  |  | Silva, J. A. et al., Biotecnologia Aplicada 15 (1998) 154-158 |
|  |  | U.S. Pat. No. 6,531,581<br>EP 0 423 839 |
|  |  | U.S. Pat. No. 4,948,882;<br>U.S. Pat. No. 5,541,313;<br>U.S. Pat. No. 5,817,786 |

TABLE V-continued

| Trifunctional nucleosidic | A | Reference |
|---|---|---|
| [structure] | ----N---label with ethyl group | WO 2001/042505 |
| [structure] | ----N(H)-C(=O)-label | McKeen, C. M. et al., Organic & Biomolecular Chemistry 1 (2003) 2267-2275 |
| [structure] | ----N(H)-C(=S)-N(H)----label | Ramzaeva, N. et al., Helvetica Chimica Acta 83 (2000)1108-1126 |

In Tables III, IV and V, one of the terminal oxygen atom of a bifunctional moiety or one of the terminal oxygen atoms of a trifunctional moiety is part of a phosphoramidite that is not shown in full detail but obvious to the skilled artisan. The second terminal oxygen atom of trifunctional building block is protected with an acid labile protecting group PG, as defined for Formula II above.

Post-synthetic modification is another strategy for introducing a covalently bound functional moiety into a linker or a spacer molecule. In this approach an amino group is introduced by using bifunctional or trifunctional building block during solid phase synthesis. After cleavage from the support and purification of the amino modified oligonucleotide is reacted with an activated ester of a functional moiety or with a bifunctional reagent wherein one functional group is an active ester. Exemplary active esters include NHS ester or pentafluor phenyl esters.

Post-synthetic modification is especially useful for introducing a functional moiety which is not stable during solid phase synthesis and deprotection. Examples are modification with triphenylphosphincarboxymethyl ester for Staudinger ligation (Wang, C. C. et al., Bioconjugate Chemistry 14 (2003) 697-701), modification with digoxigenin or for introducing a maleinimido group using commercial available sulfo SMCC.

The functional moiety X in one embodiment is bound to at least one of a', a, b, b' or S via an additional binding pair.

The additional binding pair to which a functional moiety X can be bound is may be a leucine zipper domain or a hybridizing nucleic acid. In case the functional moiety X is bound to at least one of a', a, b, b' or S via an additional binding pair member, the binding pair member to which X is bound and the binding pairs a':a and b:b', respectively, all are selected to have different specificity. The binding pairs a:a', b:b' and the binding pair to which X is bound each bind to (e.g. hybridize with) their respective partner without interfering with the binding of any of the other binding pairs.

Covalent coupling of a member of a binding pair to a monovalent binder

Depending on the biochemical nature of the binder different conjugation strategies are at hand.

In case the binder is a naturally occurring protein or a recombinat polypeptide of between 50 to 500 amino acids, there are standard procedures in text books describing the chemistry for synthesis of protein conjugates, which can be easily followed by the skilled artisan (Hackenberger, C. P. and Schwarzer, D., Angew. Chem., Int. Ed., 47 (2008) 10030-10074).

In one embodiment the reaction of a maleinimido moiety with a cystein residue within the protein is used. This is an exemplary coupling chemistry in case e.g. an Fab or Fab'-fragment of an antibody is used a monovalent binder. Alternatively in one embodiment coupling of a member of a binding pair (a' or b', respectively, of Formula I) to the C-terminal end of the binder polypeptide is performed. C-terminal modification of a protein, e.g. of an Fab-fragment can e.g. be performed as described by Sunbul, M. et al., Organic & Biomolecular Chemistry 7 (2009) 3361-3371).

In general site specific reaction and covalent coupling of a binding pair member to a monovalent polypeptidic binder is based on transforming a natural amino acid into an amino acid with a reactivity which is orthogonal to the reactivity of the other functional groups present in a protein. For example, a specific cystein within a rare sequence context can be enzymatically converted in an aldehyde (see Formylglycine aldehyde tag -protein engineering through a novel post-translational modification (Frese, M.-A. et al., ChemBioChem 10 (2009) 425-427). It is also possible to obtain a desired amino acid modification by utilizing the specific enzymatic reactivity of certain enzymes with a natural amino acid in a given sequence context (see e.g.: Taki, M. et al., Protein Engineering, Design & Selection 17 (2004) 119-126; Gautier, A. et al., Chemistry & Biology 15 (2008) 128-136; Protease-catalyzed formation of C—N bonds is used by Bordusa, F., Highlights in Bioorganic Chemistry (2004) 389-403) and Sortase-mediated protein ligation is used by Mao, H. et al., in J. Am Chem Soc. 126 (2004) 2670-2671 and reviewed by Proft, T., in Biotechnol. Lett 32 (2010) 1-10).

Site specific reaction and covalent coupling of a binding pair member to a monovalent polypeptidic binder can also be achieved by the selective reaction of terminal amino acids with appropriate modifying reagents.

The reactivity of an N-terminal cystein with benzonitrils (Ren, Hongjun Xiao et al., Angewandte Chemie, International Edition 48 (2009) 9658-9662) can be used to achieve a site-specific covalent coupling.

Native chemical ligation can also rely on C-terminal cystein residues (Taylor, E. et al., Nucleic Acids and Molecular Biology 22 (2009) 65-96).

EP 1 074 563 describes a conjugation method which is based on the faster reaction of a cystein within a stretch of negatively charged amino acids with a cystein located in a stretch of positively charged amino acids.

The monovalent binder may also be a synthetic peptide or peptide mimic. In case a polypeptide is chemically synthesized, amino acids with orthogonal chemical reactivity can be incorporated during such synthesis (de Graaf, A. J. et al., Bioconjugate Chemistry 20 (2009) 1281-1295). Since a great variety of orthogonal functional groups is at stake and can be introduced into a synthetic peptide, conjugation of such peptide to a linker is standard chemistry.

In order to obtain a mono-labeled protein the conjugate with 1:1 stoichiometry may be separated by chromatography from other conjugation products. This procedure is facilitated by using a dye labeled binding pair member and a charged spacer. By using this kind of labeled and highly negatively charged binding pair member, mono conjugated proteins are easily separated from non labeled protein and proteins which carry more than one linker, since the difference in charge and molecular weight can be used for separation. The fluorescent dye is valuable for purifying the bivalent binding agent from un-bound components, like a labeled monovalent binder.

Therefore in one embodiment a binding pair member may be used (a' and/or b', respectively of Formula I) which is labeled with a fluorescent dye (e.g. synthesized using a bifunctional or trifunctional modifier building block in combination with bifunctional spacer building blocks during synthesis) for forming the bivalent binding agent of the present embodiment. In an exemplary embodiment the spacer S as well as the sequences a, a', b and b' are DNA and at least one of a' or b', respectively, is labeled with a fluorescent dye. In other embodiments the spacer S as well as the sequences a, a', b and b' are DNA and both a' and b', respectively, are labeled each with a different fluorescent dye.

In some embodiments a method of producing a bivalent binding agent that specifically binds a posttranslationally modified target polypeptide is disclosed. The method comprises the steps of (a) selecting a first monovalent binder that binds to a polypeptide epitope of said target polypeptide with a Kdiss of between $5 \times 10^{-3}$/sec to $10^{-4}$/sec, (b) selecting a second monovalent binder that binds to a posttranslational polypeptide modification with a Kdiss of $5 \times 10^{-3}$/sec to $10^{-4}$/sec, c) coupling both monovalent binders by a linker, and d) selecting a bivalent binding agent having a Kdiss-value of $3 \times 10^{-5}$/sec or less.

As the skilled artisan will appreciate the Kdiss is a temperature-dependent value. Logically, the Kdiss-values of both the monovalent binders as well as of the bivalent binding agent according to the present embodiment are determined at the same temperature. As will be appreciated a Kdiss-value may be determined at the same temperature at which the bivalent binding agent shall be used, e.g., an assay shall be performed. In one embodiment the Kdiss-values are established at room temperature, i.e. at 20° C., 21° C., 22° C., 23° C., 24° C. or 25° C., respectively. In one embodiment the Kdiss-values are established at 4 or 8° C., respectively. In one embodiment the Kdiss-values are established at 25° C. In one embodiment the Kdiss-values are established at 37° C. In one embodiment the Kdiss-values are established at 40° C. In an embodiment, Kdiss determinations, i.e. those for each monovalent binder and the Kdiss determination for the dual binder are made at 37° C.

Using a method as disclosed in the present embodiment it is now rather easy to produce various bivalent binding agents each comprising a linker of different length and to select those bivalent binding agents having the desired binding properties, i.e. a Kdiss-value of $3 \times 10^{-5}$/sec or less. Selection of a bivalent binding agent with the desired Kdiss is performed by BIACORE™-analysis as disclosed in Example 2.8.

In one embodiment the present embodiment relates to a method of forming a bivalent binding agent according to the present embodiment, wherein a first monovalent binder that binds to a polypeptide epitope of a target polypeptide with a Kdiss of between $10^{-3}$/sec to $10^{-4}$/sec that is coupled to a member of a first binding pair, a second monovalent binder that binds to a posttranslational polypeptide modification with a Kdiss of $10^{-3}$/sec to $10^{-4}$/sec that is coupled to a member of a second binding pair, wherein the first and the second binding pair do not interfere with each other and a linker comprising a spacer and the complementary binding pair member to the first and the second binding pair member are co-incubated, whereby a bivalent binding agent having a Kdiss-value of $10^{-5}$/sec or less is formed.

In one embodiment the above method further comprises the step of isolating the bivalent binding agent.

Exemplary stoichiometry for assembling the bivalent binding agent according to the present embodiment is 1:1:1.

In an embodiment the method of producing a bivalent binding reagent according to the present embodiment makes use of an L-DNA-linker. In an embodiment the method of producing a bivalent binding reagent according to the present embodiment makes use of two specific binding pairs consisting of DNA, for example L-DNA, and of an L-DNA-linker.

The formation and stoichiometry of the formed bivalent binding agent can be analyzed by Size Exclusion Chromatography according to state of the art procedures. If desired, the formed complexes can also be analyzed by SDS-PAGE.

The bivalent binding agent disclosed in this embodiment, if used in an immunohistochemical staining procedure only significantly binds and is not washed off during the various incubation steps of such procedure if it has a Kdiss of $3 \times 10^{-5}$/sec or better. This Kdiss can only be achieved, if both monovalent binder bind to their corresponding binding site. In case only the polypeptide epitope or only a posttranslational modification is present on a molecule in the sample no significant staining will be found. Thus, and this is of great advantage, immunohistochemical staining will be only observed if the posttranslationally modified target polypeptide—carrying the relevant modification—is present in the sample.

In a some embodiments, the instant disclosure relates to a histological staining method the method comprising the steps of (a) providing a cell or tissue sample, (b) incubating said sample with a bivalent binding agent consisting of two monovalent binders that are linked to each other via a linker, wherein one of the two monovalent binders binds to a polypeptide epitope of said target polypeptide, one of the two monovalent binders binds to a posttranslational polypeptide modification, each monovalent binder has a Kdiss in the range of $5 \times 10^{-3}$/sec to $10^{-4}$/sec and wherein the bivalent binding agent has a Kdiss of $3 \times 10^{-5}$/sec or less, and (c) detecting the bivalent binding agent, thereby staining said sample for a posttranslationally modified target polypeptide.

Use of a bivalent binding agent according to the present embodiment in the staining of a cell or tissue sample by an immunohistochemical method represents a further embodiment.

In more general terms the present embodiment relates to a bivalent binding agent consisting of two monovalent binders that are linked to each other via a linker, which binding agent binds a posttranslationally modified target polypeptide with a Kdiss meeting the requirements of an (automated) assay system or better, wherein (a) the first monovalent binder that binds to a polypeptide epitope of said target polypeptide with a Kdiss of at least 10-fold above the requirements of the (automated) assays system, (b) the second monovalent binder that binds to a posttranslational polypeptide modification with a Kdiss of at least 10-fold above the requirements of the (automated) assays system, and (c) wherein the product of the Kdiss-values of the two monovalent binders (a) and (b) is at least the Kdiss required by the (automated) system or less.

In general terms a method for obtaining a bivalent binding agent is described that specifically binds a posttranslationally modified target polypeptide with a Kdiss at least meeting the minimal assay requirements of an (automated) assay system or better, the method comprising the steps of (a) selecting a first monovalent binder that binds to a non-posttranslationally modified epitope of said target polypeptide with a Kdiss of at least 10-fold above the minimal assay requirements of the (automated) assays system, (b) selecting a second monovalent binder that binds to a posttranslational polypeptide modification with a Kdiss of at least 10-fold above the minimal assay requirements of the (automated) assays system, wherein the product of the Kdiss-values of the two monovalent binders in steps (a) and (b) is at least the Kdiss required by the (automated) system or less and (c) coupling both monovalent binders by a linker.

In one embodiment the automated system is the BENCH-MARK® analyzer as distributed by Ventana Medical Systems Inc., Tucson.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

Illustrative Embodiments

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. A bivalent binding agent binding a posttranslationally modified target polypeptide consisting of two monovalent binders that are linked to each other via a linker, wherein
   a) the first monovalent binder binds to a polypeptide epitope of said target polypeptide,
   b) the second monovalent binder binds to a posttranslational polypeptide modification,
   c) each monovalent binder has a Kdiss in the range of $5 \times 10^{-3}$/sec to $10^{-4}$/sec, and
   d) wherein the bivalent binding agent has a Kdiss of $3 \times 10^{-5}$/sec or less.
2. The bivalent binding agent of embodiment 1, wherein at least one of the monovalent binders is a single chain antibody, or an Fab-fragment or an Fab'-fragment of a monoclonal antibody.
3. The bivalent binding agent of embodiment 1, wherein the monovalent binders are derived from monoclonal antibodies and are Fab-fragments, or Fab'-fragments, or an Fab-fragment and an Fab'-fragment.
4. The bivalent binding agent according to any of embodiments 1 to 3, wherein said bivalent binding agent has a Kdiss of $10^{-5}$/sec or less.
5. The bivalent binding agent according to any of embodiments 1 to 4, wherein the linker has a length of 6 to 100 nm.
6. A method for obtaining a bivalent binding agent that specifically binds a posttranslationally modified target polypeptide, the method comprising the steps of
   a) selecting a first monovalent binder that binds to a non-posttranslationally modified epitope of said target polypeptide with a Kdiss of between $5 \times 10^{-3}$/sec to $10^{-4}$/sec, b) selecting a second monovalent binder that binds to a posttranslational polypeptide modification with a Kdiss of $5 \times 10^{-3}$/sec to $10^{-4}$/sec, c) coupling both monovalent binders by a linker, and d) selecting a bivalent binding agent having a Kdiss-value of $3 \times 10^{-5}$/sec or less.

7. The method of embodiment 6 further comprising the step e) of isolating the bivalent binding agent.

8. The bivalent binding agent according to any of embodiments 1 to 5 or the method according to embodiments 6 or 7, wherein the posttranslational modification is selected from the group consisting of acetylation, phosphorylation, acylation, methylation, glycosylation, ubiquitinylation, sumoylation, sulfatation and nitration.

9. The bivalent binding agent according to any of embodiments 1 to 5 or the method according to embodiments 6 or 7, wherein the posttranslational modification is selected from the group consisting of phosphorylation, glycosylation and acetylation.

10. The bivalent binding agent according to any of embodiments 1 to 5 or the method according to embodiments 6 or 7, wherein the target polypeptide is selected from the group consisting of membrane-bound receptor molecules having an intracellular phosphorylation site and intracellular cell signaling molecules.

11. A histological staining method the method comprising the steps of
    a) providing a cell or tissue sample,
    b) incubating said sample with a bivalent binding agent binding a posttranslationally modified target polypeptide consisting of two monovalent binders that are linked to each other via a linker, wherein one of the two monovalent binders binds to a polypeptide epitope of said target polypeptide, one of the two monovalent binders binds to a posttranslational polypeptide modification, each monovalent binder has a Kdiss in the range of $5 \times 10^{-3}$/sec to $10^{-4}$/sec and wherein the bivalent binding agent has a Kdiss of $3 \times 10^{-5}$/sec or less, and
    c) detecting the bivalent binding agent, thereby staining said sample for a posttranslationally modified target polypeptide.

12. Use of a bivalent binding agent according to any of embodiments 1 to 5 in the staining of a cell or tissue sample.

EXAMPLES

Example 1

Bivalent Binding Agent to Troponin T 1.1 Monoclonal Antibodies and Fab'-Fragments Two monoclonal antibodies binding to human cardiac Troponin T at different, non-overlapping epitopes, epitope A' and epitope B', respectively, were used. Both these antibodies are used in the current Roche ELECSYS™ Troponin T assay, wherein Troponin T is detected in a sandwich immuno assay format.

Purification of the monoclonal antibodies from culture supernatant was carried out using state of the art methods of protein chemistry.

The purified monoclonal antibodies are protease digested with either pre-activated papain (anti-epitope A' MAb) or pepsin (anti-epitope B' MAb) yielding F(ab')2 fragments that are subsequently reduced to Fab'-fragments with a low concentration of cysteamin at 37° C., i.e. A and B, respectively, in Formula I (A-a':a-S-b:b'-B). The reaction is stopped by separating the cysteamin on a SEPHADEX® G-25 column (GE Healthcare) from the polypeptide-containing part of the sample.

1.2 Conjugation of Fab'-Fragments to ssDNA-Oligonucleotides

The Fab'-fragments are conjugated with the below described activated ssDNAa and ssDNAb oligonucleotides, respectively.

Preparation of the Fab-Fragment-ssDNA Conjugates A" and B", Respectively:

a) Fab'-Anti-Troponin T<Epitope A'>-ssDNA-Conjugate (=A")

For preparation of the Fab'-anti-Troponin T<epitope A'>-ssDNA-conjugate A" a derivative of SED ID NO:5 is used, i.e. 5'-AGT CTA TTA ATG CTT CTG C(=SEQ ID NO:5)-XXX-Y-Z-3', wherein X=propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y=3"-Amino-Modifier C6 introduced via 3'-Amino Modifier TFA Amino C-6 lcaa CPG (ChemGenes) and wherein Z=4[N-maleinimidomethyl]cyclohexane-1-carboxy introduced via Sulfosuccinimidyl 4-[N-maleimidomethyl]cyclohexane-1-carboxylate (ThermoFischer).

b) Fab'-Anti-Troponin T<Epitope B'>-ssDNA-Conjugate (=B")

For the preparation of the Fab-anti-Troponin T<epitope B'>-ssDNAb-conjugate (B") a derivative of SEQ ID NO:6 is used, i.e. 5'-Y-Z-XXX-AGT TCT ATC GTC GTC CA-3', wherein X=propylene-phosphate introduced via Phosphoramidite C3 (3-(4,4'-Dimethoxytrityloxy)propyl-1-[(2-cyanoethyl)-(N,N-diisopropyl)]-phosphoramidite (Glen Research), wherein Y=5'-Amino-Modifier C6 introduced via (6-(4-Monomethoxytritylamino)hexyl-(2-cyanoethyl)-(N,N-diisopropyl)-phosphoramidite (Glen Research), and wherein Z=4[N-maleinimidomethyl]cyclohexane-1-carboxy introduced via Sulfosuccinimidyl 4-[N-maleimidomethyl]cyclohexane-1-carboxylate (ThermoFischer).

The oligonucleotides of SEQ ID NO:5 or 6, respectively, have been synthesized by state of the art oligonucleotide synthesis methods. The introduction of the maleinimido group was done via reaction of the amino group of Y with the succinimidyl group of Z which was incorporated during the solid phase oligonucleotide synthesis process.

The single-stranded DNA constructs shown above bear a thiol-reactive maleimido group that reacts with a cysteine of the Fab' hinge region generated by the cysteamine treatment. In order to obtain a high percentage of single-labeled Fab'-fragments the relative molar ratio of ssDNA to Fab'-fragment is kept low. Purification of single-labeled Fab'-fragments (ssDNA:Fab'=1:1) occurs via anion exchange chromatography (column: MONO Q®, GE Healthcare). Verification of efficient labeling and purification is achieved by analytical gel filtration chromatography and SDS-PAGE.

1.3 Biotinylated Linker Molecules

The oligonucleotides used in the ssDNA linkers L1, L2 and L3, respectively, have been synthesized by state of the art oligonucleotide synthesis methods and employing a biotinylated phosphoramidite reagent for biotinylation.

Linker 1 (=L1), a biotinylated ssDNA linker 1 with no spacer has the following composition:

5'-GCA GAA GCA TTA ATA GAC T (Biotin-dT)-TGG ACG ACG ATA GAA CT-3' (SEQ ID NO:27). It comprises ssDNA oligonucleotides of SEQ ID NO:7 and 8, respectively, and was biotinylated by using Biotin-dT (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite (Glen Research).

Linker 2 (=L2), a biotinylated ssDNA linker 2 with a 11 mer spacer has the following composition:

5'-GCA GAA GCA TTA ATA GAC T T5-(Biotin-dT)-T5 TGG ACG ACG ATA GAA CT-3' (SEQ ID NO:28). It comprises ssDNA oligonucleotides of SEQ ID NO:7 and 8, respectively, twice oligonucleotide stretches of five thymidines each and was biotinylated by using Biotin-dT (=T-Bi) (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite (Glen Research) in the middle of the spacer.

Linker 3 (=L3), a biotinylated ssDNA linker 3 with a 31 mer spacer has the following composition:

5'-GCA GAA GCA TTA ATA GAC T T15-(Biotin-dT)-T15 TGG ACG ACG ATA GAA CT-3' (SEQ ID NO:29). It comprises ssDNA oligonucleotides of SEQ ID NO:7 and 8, respectively, twice oligonucleotide stretches of fifteen thymidines each and was biotinylated by using Biotin-dT (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite (Glen Research) in the middle of the spacer.

1.4 Epitopes for Monovalent Troponin T Binders A and B, Respectively

Synthetic peptides have been construed that individually only have a moderate affinity to the corresponding Fab'-fragment derived from the anti-Troponin T antibodies a and b, respectively.

a) The epitope A' for antibody a is comprised in:
SEQ ID NO:9=ERAEQQRIRAER-EKEUUSLKDRIEKRRRAERAEamide, wherein U represents ß-Alanin.

b) The epitope B' for antibody b is comprised in:
SEQ ID NO:10=SLKDRIERRRAERAEOOER-AEQQRIRAEREKEamide, wherein O represents Aminotrioxa-octanoic-acid As the skilled artisan will appreciate it is possible to combine these two epitope-containing peptides in two ways and both variants have been designed and prepared by linear combining the epitopes A' and B'. The sequences of both variants, the linear sequences of epitopes A'-B' (=TnT-1) and B'-A' (=TnT-2), respectively have been prepared by state of the art peptide synthesis methods.

The sequences for epitopes A' and B', respectively, had been modified compared to the original epitopes on the human cardiac Troponin T sequence (P45379/UniProtKB) in order to reduce the binding affinity for each of the Fabs thereto. Under these circumstances the dynamics of the effect of hetero-bivalent binding is better visible, e.g. by analyzing binding affinity with the BIACORE™ Technology.

1.5 Biomolecular Interaction Analysis

For this experiment a BIACORE™ 3000 instrument (GE Healthcare) was used with a BIACORE™ SA sensor mounted into the system at T=25° C. Preconditioning was done at 100 µl/min with 3×1 min injection of 1 M NaCl in 50 mM NaOH and 1 min 10 mM HCl.

HBS-ET (10 mM HEPES pH 7.4, 150 mM NaCl, 1 mM EDTA, 0.05% TWEEN® 20 was used as system buffer. The sample buffer was identical to the system buffer.

The BIACORE™ 3000 System was driven under the control software V1.1.1. Flow cell 1 was saturated with 7 RU D-biotin. On flow cell 2, 1063 RU biotinylated ssDNA linker L1 was immobilized. On flow cell 3, 879 RU biotinylated ssDNA linker L2 was immobilized. On flow cell 4, 674 RU biotinylated ssDNA linker L3 was captured.

Thereafter, Fab' fragment DNA conjugate A" was injected at 600 nM. Fab' fragment DNA conjugate B" was injected into the system at 900 nM. The conjugates were injected for 3 min at a flow rate of 2 µl/min. The conjugates were consecutively injected to monitor the respective saturation signal of each Fab' fragment DNA conjugate on its respective linker. Fab' combinations were driven with a single Fab' fragment DNA conjugate A", a single Fab' fragment DNA conjugate B" and both Fab' fragment DNA conjugates A" and B" present on the respective linker. Stable baselines were generated after the linkers have been saturated by the Fab' fragment DNA conjugates, which was a prerequisite for further kinetic measurements.

The artificial peptidic analytes TnT-1 and TnT-2 were injected as analytes in solution into the system in order to interact with the surface presented Fab' fragments.

TnT-1 was injected at 500 nM, TnT-2 was injected at 900 nM analyte concentration. Both peptides were injected at 50 µl/min for 4 min association time. The dissociation was monitored for 5 min. Regeneration was done by a 1 min injection at 50 µl/min of 50 mM NaOH over all flow cells.

Kinetic data was determined using the Biaevaluation software (V.4.1). The dissociation rate kd (1/s) of the TnT-1 and TnT-2 peptides from the respective surface presented Fab' fragment combinations was determined according to a linear Langmuir 1:1 fitting model. The complex halftime in min were calculated according to the solution of the first order kinetic equation: $\ln(2)/(60*kd)$.

Results:

The experimental data given in Tables 1 and 2, respectively demonstrate an increase in complex stability between analyte (TnT-1 or TnT-2), respectively, and the various heterobivalent Fab'-Fab' dimers A"-B" as compared to the monovalent dsDNA Fab' A" or B" conjugate, respectively. This effect is seen in each Table in line 1 compared to lines 2 and 3.

TABLE 1

Analysis data using TnT-1 with linkers of various length

| Fab' fragment DNA conjugate A" | Fab' fragment DNA conjugate B" | kd (1/s) | t½ diss (min) |
|---|---|---|---|
| a) Linker L1 | | | |
| x | x | 6.6E−03 | 1.7 |
| x | — | 3.2E−02 | 0.4 |
| — | x | 1.2E−01 | 0.1 |
| b) Linker L2 | | | |
| x | x | 4.85E−03 | 2.4 |
| x | — | 2.8E−02 | 0.4 |
| — | x | 1.3E−01 | 0.1 |
| c) Linker L3 | | | |
| Fab' fragment DNA conjugate A" | Fab' fragment DNA conjugate B" | kd (/1/s) | t½ diss (min) |
| x | x | 2.0E−03 | 5.7 |
| x | — | 1.57E−02 | 0.7 |
| — | x | 1.56E−02 | 0.7 |

TABLE 2

Analysis data using TnT-2 with linkers of various length

| Fab' fragment DNA conjugate A" | Fab' fragment DNA conjugate B" | kd (/1/s) | t½ diss (min) |
|---|---|---|---|
| a) Linker L1 | | | |
| x | x | 1.4E−02 | 0.8 |
| x | — | 4.3E−02 | 0.3 |
| — | x | 1.4E−01 | 0.1 |
| b) Linker L2 | | | |
| x | x | 4.9E−03 | 2.3 |
| x | — | 3.5E−02 | 0.3 |
| — | x | 1.3E−01 | 0.1 |
| c) Linker L3 | | | |
| x | x | 8.0E−03 | 1.5 |
| x | — | 4.9E−02 | 0.2 |
| — | x | 3.2E−01 | 0.04 |

The avidity effect is further dependent on the length of the linker. In the sub-tables shown under Table 1, i.e. for the artificial analyte TnT-1, the linker L3 comprising a thymidine-based 31mer spacer shows the lowest dissociation rate or highest complex stability.

In the sub-tables shown under Table 2 the linker L2 comprising an thymidine-based 11 mer spacer exhibits the lowest dissociation rate or highest complex stability for the artificial analyte TnT-2.

These data taken together demonstrate that the flexibility in linker length as inherent to the approach given in the present embodiment is of great utility and advantage.

Example 2

Bivalent Binding Agent to Phosphorylated IGF-1R
2.1 Monoclonal Antibody Development (mAb 8.1.2, mAb 1.4.168 and mAB 30.4.33)
a) Immunization of Mice BALB/C mice are immunized at week 0, 3, 6 and 9, respectively. Per immunization 100 µg of the conjugate comprising the phosphorylated peptide pIGF-1R (1340-1366) (SEQ ID NO:11) is used. This peptide had been phosphorylated at tyrosine 1346 (=1346-pTyr) and coupled to KLH via the C-terminal cysteine (=Aoc-Cys-MP-KLH-1340) to yield the conjugate used for immunization. At weeks 0 and 6, respectively, the immunization is carried out intraperitoneally and at weeks 3 and 9, respectively, subcutaneously at various parts of the mouse body.

b) Fusion and Cloning

Spleen cells of immunized mice are fused with myeloma cells according to Galfre G., and Milstein C., Methods in Enzymology 73 (1981) 3-46. In this process ca $1 \times 10^8$ spleen cells of an immunized mouse are mixed with $2 \times 10^7$ myeloma cells a(P3×63-Ag8653, ATCC CRL1580) and centrifuged (10 min at 250 g and 37° C.). The cells are then washed once with RPMI 1640 medium without fetal calf serum (FCS) and centrifuged again at 250 g in a 50 ml conical tube. The supernatant is discarded, the cell sediment is gently loosened by tapping, 1 ml PEG (molecular weight 4000, Merck, Darmstadt) is added and mixed by pipetting. After 1 min incubation in a water bath at 37° C., 5 ml RPMI 1640 without FCS is added drop-wise at room temperature within a period of 4-5 min. This step is repeated with additional 10 ml RPMI 1640 without FCS. Afterwards 25 ml RPMI 1640 containing 10% FCS is added followed by an incubation step at 37° C., 5% $CO_2$ for 30 minutes. After centrifugation for 10 min at 250 g and 4° C. the sedimented cells are taken up in RPMI 1640 medium containing 10% FCS and seeded out in hypoxanthine-azaserine selection medium (100 mmol/l hypoxanthine, 1 µg/ml azaserine in RPMI 1640+10% FCS). Interleukin 6 at 100 U/ml is added to the medium as a growth factor. After 7 days the medium is exchanged with fresh medium. On day 10, the primary cultures are tested for specific antibodies. Positive primary cultures are cloned in 96-well cell culture plates by means of a fluorescence activated cell sorter.

c) Immunoglobulin Isolation from the Cell Culture Supernatants

The hybridoma cells obtained are seeded out at a density of $1 \times 10^7$ cells in CELLINE™ 1000 CL flasks (Integra). Hybridoma cell supernatants containing IgGs are collected twice a week. Yields typically range between 400 µg and 2000 µg of monoclonal antibody per 1 ml supernatant. Purification of the antibody from culture supernatant was carried out using conventional methods of protein chemistry (e.g. according to Bruck, C., Methods in Enzymology 121 (1986) 587-596).

2.2 Synthesis of Hybridizable Oligonucleotides

The following amino modified precursors, comprising the sequences given in SEQ ID NOs: 5 and 6, respectively, were synthesized according to standard methods. The below given oligonucleotides not only comprise the so-called aminolinker, but also a fluorescent dye. As the skilled artisan will readily appreciate, this fluorescent dye is very convenient to facilitate purification of the oligonucleotide as such, as well as of components comprising them.

a) 5'-Fluorescein-AGT CTA TTA ATG CTT CTG C-(Spacer C3)3-C7Aminolinker-;
b) 5'-CY5™ AGT CTA TTA ATG CTT CTG C-(Spacer C3)3-C7Aminolinker-;
c) 5'-Aminolinker-(Spacer C3)3-AGT TCT ATC GTC GTC CA-Fluorescein-3';
d) 5'-Fluorescein-(beta L AGT CTA TTA ATG CTT CTG C)-(Spacer C3)3-C7Aminolinker-; (beta L indicates that this is an L-DNA oligonucleotide) and
e) 5'-Aminolinker-(Spacer C3)3-(beta L-AGT TCT ATC GTC GTC CA)-Fluorescein-3' (beta L indicates that this is an L-DNA oligonucleotide).

Synthesis was performed on an ABI 394 synthesizer at a 10 µmol scale in the trityl on (for 5' amino modification) or trityl off mode (for 3' amino modification) using commercially available CPGs as solid supports and standard dA(bz), dT, dG (iBu) and dC(Bz) phosphoramidites (Sigma Aldrich).

The following amidites, amino modifiers and CPG supports were used to introduce the C3-spacer, a dye and amino moieties, respectively, during oligonucleotide synthesis:

Spacer Phosphoramidite C3 (3-(4,4'-Dimethoxytrityloxy) propyl-1-[(2-cyanoethyl)-(N,N-diisopropyl)]-phosphoramidite (Glen Research);

5' amino modifier is introduced by using 5'-Amino-Modifier C6 (6-(4-Monomethoxytritylamino)hexyl-(2-cyanoethyl)-(N,N-diisopropyl)-phosphoramidite (Glen Research);

5'-Fluorescein Phosphoramidite 6-(3',6'-dipivaloylfluoresceinyl-6-carboxamido)-hexyl-1-O-(2-cyanoethyl)-(N,N-diisopropyl)-phosphoramidite (Glen Research);

CY5™ Phosphoramidite 1-[3-(4-monomethoxytrityloxy) propyl]-1'-[3-[(2-cyanoethyl)-(N,N-diisopropyl phosphoramidityl]propyl]-3,3,3',3'-tetramethylindodicarbocyanine chloride (Glen Research);

LIGHTCYCLER® Fluoresceine CPG 500 A (Roche Applied Science); and

3'-Amino Modifier TFA Amino C-6 lcaa CPG 500 A (Chemgenes),

For CY5™ labeled oligonucleotides, dA(tac), dT, dG(tac) dC(tac) phosphoramidites, (Sigma Aldrich), were used and deprotection with 33% ammonia was performed for 2 h at room temperature.

L-DNA oligonucleotides were synthesized by using beta-L-dA(bz), dT, dG (iBu) and dC(Bz) phosphoramidites (Chemgenes)

Purification of fluorescein modified hybridizable oligonucleotides was performed by a two step procedure: First the oligonucleotides were purified on reversed-phase HPLC (Merck-Hitachi-HPLC; RP-18 column; gradient system [A: 0.1 M (Et3NH)OAc (pH 7.0)/MeCN 95:5; B: MeCN]: 3 min, 20% B in A, 12 min, 20-50% B in A and 25 min, 20% B in A with a flow rate of 1.0 ml/min, detection at 260 nm. The fractions (monitored by analytical RP HPLC) containing the desired product were combined and evaporated to dryness. (Oligonucleotides modified at the 5' end with monomethoxytrityl protected alkylamino group are detriylated by incubating with 20% acetic acid for 20 min). The oligomers containing fluorescein as label were purified again by IEX chromatography on a HPLC [MONO Q® column: Buffer A: Sodium hydroxide (10 mM/l; pH ~12) Buffer B 1M Sodium chloride dissolved in Sodium hydroxide (10 mM/l; pH ~12) gradient: in 30 minutes from 100% buffer A to 100% buffer B flow 1 ml/min detection at 260 nm]. The product was desalted via dialysis.

CY5™ labeled oligomers were used after the first purification on reversed-phase HPLC (Merck-Hitachi-HPLC; RP-18 column; gradient system [A: 0.1 M (Et3NH)OAc (pH 7.0)/MeCN 95:5; B: MeCN]: 3 min, 20% B in A, 12 min, 20-50% B in A and 25 min, 20% B in A with a flow rate of 1.0 ml/min, detection at 260 nm. The oligomers were desalted by dialysis and lyophilized on a SPEEDVAC® evaporator to yield solids which were frozen at −24° C.

2.3 Activation of Hybridizable Oligonucleotides

The amino modified oligonucleotides from Example 2 were dissolved in 0.1 M sodium borate buffer pH 8.5 buffer (c=600 μmol) and reacted with a 18-fold molar excess of Sulfo SMCC (Sulfosuccinimidyl 4-[N-maleimidomethyl] cyclohexane-1-carboxylate dissolved in DMF (c=3 mg/100 μl) from Thermo Scientific, The reaction product was thoroughly dialyzed against water in order to remove the hydrolysis product of sulfoSMCC 4-[N-maleimidomethyl]cyclohexane-1-carboxylate.

The dialysate was concentrated by evaporation and directly used for conjugation with a monovalent binder comprising a thiol group.

2.4 Synthesis of Linker Oligonucleotides Comprising Hybridizable Oligonucleotides at Both Ends Oligonucleotides were synthesized by standard methods on an ABI 394 synthesizer at a 10 μmol scale in the trityl on mode using commercially available dT-CPG as solid supports and using standard dA(bz), dT, dG (iBu) and dC(Bz) phosphoramidites (Sigma Aldrich).

L-DNA oligonucleotides were synthesized by using commercially available beta L-dT-CPG as solid support and beta-L-dA(bz), dT, dG (iBu) and dC(Bz) phosphoramidites (Chemgenes)

Purification of the oligonucleotides was performed as described under Example 2.3 on a reversed-phase HPLC. The fractions (analyzed/monitored by analytical RP HPLC) containing the desired product were combined and evaporated to dryness. Detriylation was performed by incubating with 80% acetic acid for 15 min) The acetic acid was removed by evaporation. The reminder was dissolved in water and lyophilized.

The following amidites and CPG supports were used to introduce the C18 spacer, digoxigenin and biotin group during oligonucleotide synthesis:

Spacer Phosphoramidite 18 (18-O-Dimethoxytritylhexaethyleneglycol, 1-[(2-cyanoethyl)-(N,N-diisopropyl)]-phosphoramidite (Glen Research);

Biotin-dT (5'-Dimethoxytrityloxy-5-[N-((4-t-butylbenzoyl)-biotinyl)-aminohexyl]-3-acrylimido]-2'-deoxyUridine-3'-[(2-cyanoethyl)-(N,N-diisopropyl)]-phosphoramidite (Glen Research);

Biotin Phosphoramidite1-Dimethoxytrityloxy-2-(N-biotinyl-4-aminobutyl)-propyl-3-O-(2-cyanoethyl)-(N,N-diisopropyl)-phosphoramidite and 5'-Dimethoxytrityl-5-[N-(trifluoroacetylaminohexyl)-3-acrylimido]-2'-deoxy uridine, 3'-[(2-cyanoethyl)-(N,N-diisopropyl)]-phosphoramidite for amino modification and postlabeling with Digoxigenin-N-Hydroxyl-succininimidyl ester.

The following bridging constructs or linkers were synthesized:

Linker 1:
5'-G CAG AAG CAT TAA TAG ACT-TGG ACG ACG ATA GAA CT-3'

Linker 2:
5'-G CAG AAG CAT TAA TAG ACT-(T40)-TGG ACG ACG ATA GAA CT-3'

Linker 3:
5'-[B-L]G CAG AAG CAT TAA TAG ACT-(Biotin-dT)-TGG ACG ACG ATA GAA CT-3'

Linker 4:
5'-[B-L]G CAG AAG CAT TAA TAG ACT-T5-(Biotin-dT)-T5-TGG ACG ACG ATA GAA CT-3'

Linker 5:
5'-[B-L]G CAG AAG CAT TAA TAG ACT-T20-(Biotin-dT)-T20-TGG ACG ACG ATA GAA CT-3'

Linker 6:
5'-[B-L] G CAG AAG CAT TAA TAG ACT-T30-(Biotin-dT)-T30-TGG ACG ACG ATA GAA CT-3'

Linker 7:
5'-GCA GAA GCA TTA ATA GAC T T5-(Biotin-dT)-T5 TG GAC GAC GAT AGA ACT-3'

Linker 8:
5'-GCA GAA GCA TTA ATA GAC T T10-(Biotin-dT)-T10 TGG ACG ACG ATA GAA CT-3'

Linker 9:
5'-GCA GAA GCA TTA ATA GAC T T15-(Biotin-dT)-T15 TGG ACG ACG ATA GAA CT-3'

Linker 10:
5'-GCA GAA GCA TTA ATA GAC T T20-(Biotin-dT)-T20 TGG ACG ACG ATA GAA CT-3'

Linker 11:
5'-G CAG AAG CAT TAA TAG ACT-Spacer C18-(Biotin-dT)-Spacer C18-TGG ACG ACG ATA GAA CT-3'

-continued

Linker 12:
5'-G CAG AAG CAT TAA TAG ACT-(Spacer C18)2-

(Biotin-dT)-(Spacer C18)2-TGG ACG ACG ATA GAA

CT-3'

Linker 13:
5'-G CAG AAG CAT TAA TAG ACT-(Spacer C18)3-

(Biotin-dT)-(Spacer C18)3-TGG ACG ACG ATA GAA

CT-3'

Linker 14:
5'-G CAG AAG CAT TAA TAG ACT-(Spacer C18)4-

(Biotin-dT)-(Spacer C18)4-TGG ACG ACG ATA GAA

CT-3'

Linker 15:
5'-G CAG AAG CAT TAA TAG ACT-T20-(Dig-dT)-T20-

TGG ACG ACG ATA GAA CT-3'

Linker 16:
5'-G CAG AAG CAT TAA TAG ACT-(Dig-dT)-TGG ACG

ACG ATA GAA CT-3'

Linker 17:
5'-G CAG AAG CAT TAA TAG ACT-(Biotin-dT)-TGG ACG

ACG ATA GAA CT-3'

The above bridging construct examples comprise at least a first hybridizable oligonucleotide and a second hybridizable oligonucleotide. Linkers 3 to 17 in addition to the hybridizable nucleic acid stretches comprise a central biotinylated or digoxigenylated thymidine, respectively, or a spacer consisting of thymidine units of the length given above.

The 5'-hybridizable oligonucleotide corresponds to SEQ ID NO:7 and the 3'-hybridizable oligonucleotide corresponds to SEQ ID NO:8, respectively. The oligonucleotide of SEQ ID NO:7 will readily hybridize with the oligonucleotide of SED ID NO:5. The oligonucleotide of SEQ ID NO:8 will readily hybridize with the oligonucleotide of SED ID NO:6.

In the above bridging construct examples [B-L] indicates that an L-DNA oligonucleotide sequence is given; spacer C 18, Biotin and Biotin dT respectively, refer to the C18 spacer, the Biotin and the Biotin-dT as derived from the above given building blocks; and T with a number indicates the number of thymidine residues incorporated into the linker at the position given.

2.5 Assembly of Dual Binder Construct

A) Cleavage of IgGs and Labeling of Fab' Fragments with ssDNA

Purified monoclonal antibodies were cleaved with the help of pepsin protease yielding F(ab')2 fragments that are subsequently reduced to Fab' fragments by treatment with low concentrations of cysteamine at 37° C. The reaction is stopped via separation of cysteamine on a PD 10 column. The Fab' fragments are labeled with an activated oligonucleotide as produced according to Example 3. This single-stranded DNA (=ssDNA) bears a thiol-reactive maleimido group that reacts with the cysteines of the Fab' hinge region. In order to obtain high percentages of single-labeled Fab' fragments the relative molar ratio of ssDNA to Fab'-fragment is kept low. Purification of single-labeled Fab' fragments (ssDNA:Fab'=1:1) occurs via ion exchange chromatography (column: SOURCE™ 15 Q PE 4.6/100, Pharmacia/GE). Verification of efficient purification is achieved by analytical gel filtration and SDS-PAGE.

B) Assembly of an Anti-pIGF-1R Dual Binder.

The anti-pIGF-1R dual binder is based on two Fab' fragments that target different epitopes of the intracellular domain of IGF-1R: Fab' 8.1.2 detects a phosphorylation site (pTyr 1346) and Fab' 1.4.168 a non-phospho site of the said target protein. The Fab' fragments have been covalently linked to single-stranded DNA (ssDNA): Fab' 1.4.168 to a 17mer ssDNA comprising SEQ ID NO:6 and containing fluorescein as an fluorescent marker and Fab' 8.1.2 to a 19mer ssDNA comprising SEQ ID NO:5 and containing CY5™ as fluorescent marker. In the following, these Fab's with covalently bound 17mer or 19mer ssDNA are named ssFab' 1.4.168 and ssFab' 8.1.2 respectively. Dual binder assembly is mediated by a linker (i.e. a bridging construct comprising two complementary ssDNA oligonucleotides (SEQ ID NOs:7 and 8, respectively) that hybridize to the corresponding ssDNAs of the ssFab' fragments. The distance between the two ssFab' fragments of the dual binder can be modified by using spacers, e.g. C18-spacer or DNAs of different length, respectively.

Figure 1D:
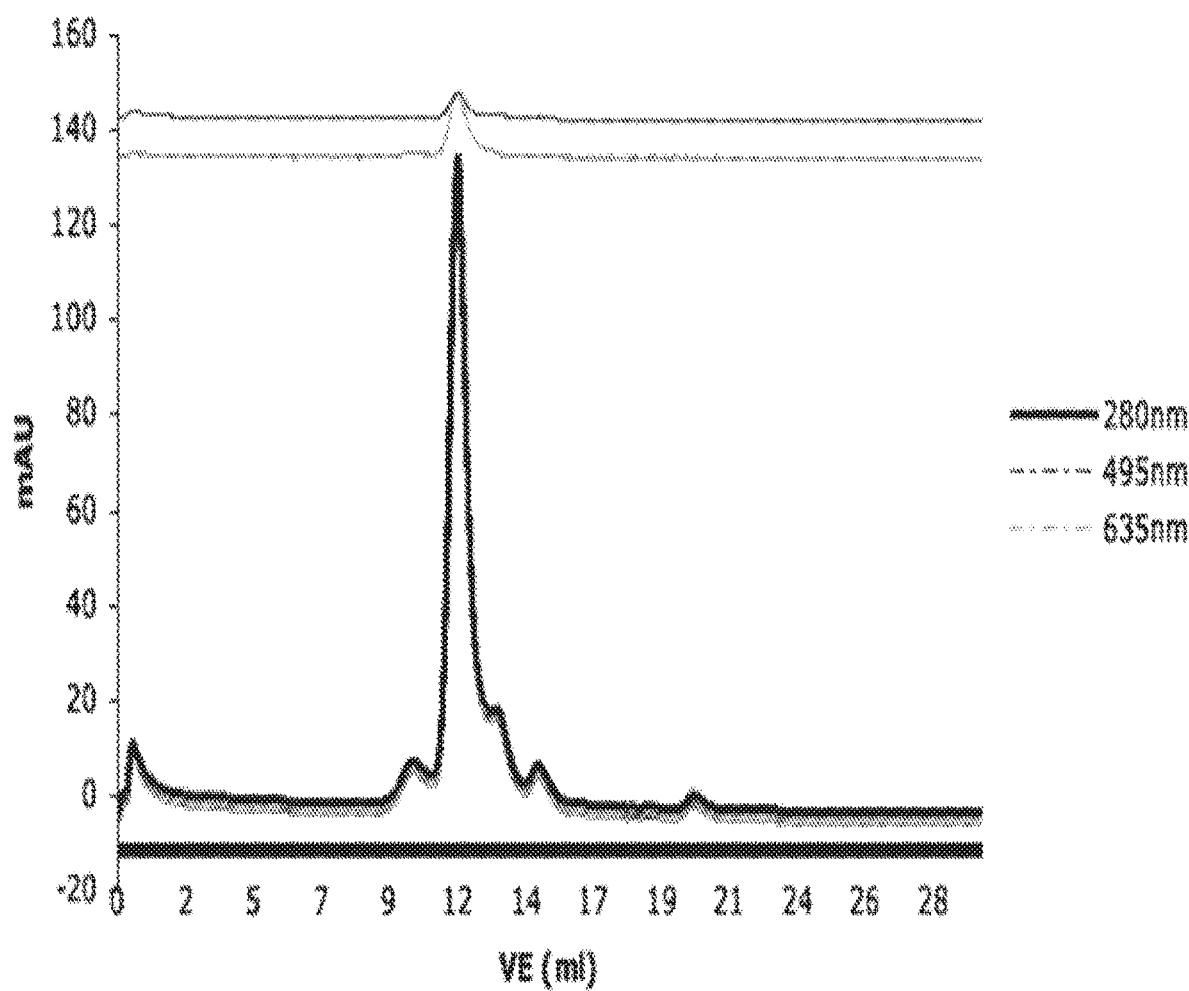

For assembly evaluation the dual binder components ssFab' 8.1.2, ssFab' 1.4.168 and the linker constructs (I) (=linker 17 of example 2.4) 5'-G CAG AAG CAT TAA TAG ACT T(-Bi)-TGG ACG ACG ATA GAA CT-3' and (II) (=linker 10 of example 2.4) 5'-G CAG AAG CAT TAA TAG ACT-(T 20)-T(-Bi)-(T20)-TGG ACG ACG ATA GAA CT-3' were mixed in equimolar quantities at room temperature. After a 1 minute incubation step the reaction mix was analyzed on an analytical gel filtration column (SUPERDEX™ 200, 10/300 GL, GE Healthcare). Comparison of the elution volumes ($V_E$) of the single dual binder components with the $V_E$ of the reaction mix demonstrates that the dual binder has been formed successfully (FIG. 1). (The biotinylated thymidine (T-(Bi)) in the middle of both of the linkers is without function in these experiments.)

2.6 BIACORE™ Experiment Assessing Binding of Anti-pIGF-1R Dual Binder to Immobilized IGF-1R and IR Peptides For this experiment a BIACORE™ 2000 instrument (GE Healthcare) was used with a BIACORE™ SA sensor mounted into the system at T=25° C. Preconditioning occurred at 100 µl/min with 3×1 min injection of 1 M NaCl in 50 mM NaOH and 1 min 10 mM HCl.

HBS-ET (10 mM HEPES pH 7.4, 150 mM NaCl, 1 mM EDTA, 0.05% TWEEN® 20 was used as system buffer. The sample buffer was identical with the system buffer.

The BIACORE™ 2000 System was driven under the control software V1.1.1.

Subsequently biotinylated peptides were captured on the SA surface in the respective flow cells. 16 RU of IGF-1R (1340-1366)[1346-pTyr; Glu(Bi-PEG-1340]amid (i.e. the -1346 tyrosine phosphorylated-peptide of SEQ ID NO:11 comprising a PEG-linker bound via glutamic acid corresponding to position 1340 and being biotinylated at the other end of the linker) was captured on flow cell 2. 18 RU of IGF-1R(1340-1366); Glu(Bi-PEG-1340]amid (i.e. the -1346 tyrosine non-phosphorylated-peptide of SEQ ID NO:11 comprising a PEG-linker bound via glutamic acid corresponding to position 1340 and being biotinylated at the other end of the linker) was captured on flow cell 3. 20 RU of hIR(1355-1382)[1361-pTyr; Glu(Bi-PEG-1355]amid (i.e. the -1361 tyrosine phosphorylated-peptide of SEQ ID NO:12 comprising a PEG-linker bound via glutamic acid corresponding to position 1355 of human insulin receptor and being biotinylated at the other end of the linker) was captured on flow cell 4. Finally all flow cells were saturated with d-biotin.

For the dual binder formation the assembly protocol as described in Example 2.5 was used. When individual runs with only one of the two ssFab's were performed, the absence or presence of linker DNA did not affect the association or dissociation curves (data not shown).

100 nM of analyte (i.e. in these experiments a bivalent dual binding agent) in solution was injected at 50 μl/min for 240 sec association time and dissociation was monitored for 500 sec. Efficient regeneration was achieved by using a 1 min injection step at 50 μl/min with 80 mM NaOH. Flow cell 1 served as a reference. A blank buffer injection was used instead of an antigen injection to double reference the data by buffer signal subtraction.

In each measurement cycle one of the following analytes in solution was injected over all 4 flow cells: 100 nM ssFab' 8.1.2, 100 nM ssFab' 1.4.168, a mixture of 100 nM ssFab' 8.1.2 and 100 nM ssFab', 100 nM bivalent binding agent consisting of ssFab' 8.1.2 and ssFab' 1.4.168 hybridized on linker III) (5'-G CAG AAG CAT TAA TAG ACT-T(20)-T(-Dig)-(T20)-TGG ACG ACG ATA GAA CT-3'(=linker 15 of example 2.4)), and 100 nM bivalent binding agent consisting of ssFab' 8.1.2 and ssFab' 1.4.168 hybridized on linker (IV) (5'-G CAG AAG CAT TAA TAG ACT-T(-Dig)-TGG ACG ACG ATA GAA CT-3'(=linker 16 of example 2.4)), respectively. (The digoxigenylation of the middle thymidine (T(-Dig)) in the above linkers is without relevance to these experiments.)

The signals were monitored as time-dependent BIACORE™ sensorgrams.

Report points were set at the end of the analyte association phase (Binding Late, BL) and at the end of the analyte dissociation phase (Stability Late, SL) to monitor the response unit signal heights of each interaction. The dissociation rates kd (1/s) were calculated according to a linear 1:1 Langmuir fit using the BIACORE™ evaluation software 4.1. The complex halftimes in minutes were calculated upon the formula ln(2)/(60*kd).

Figure 3:
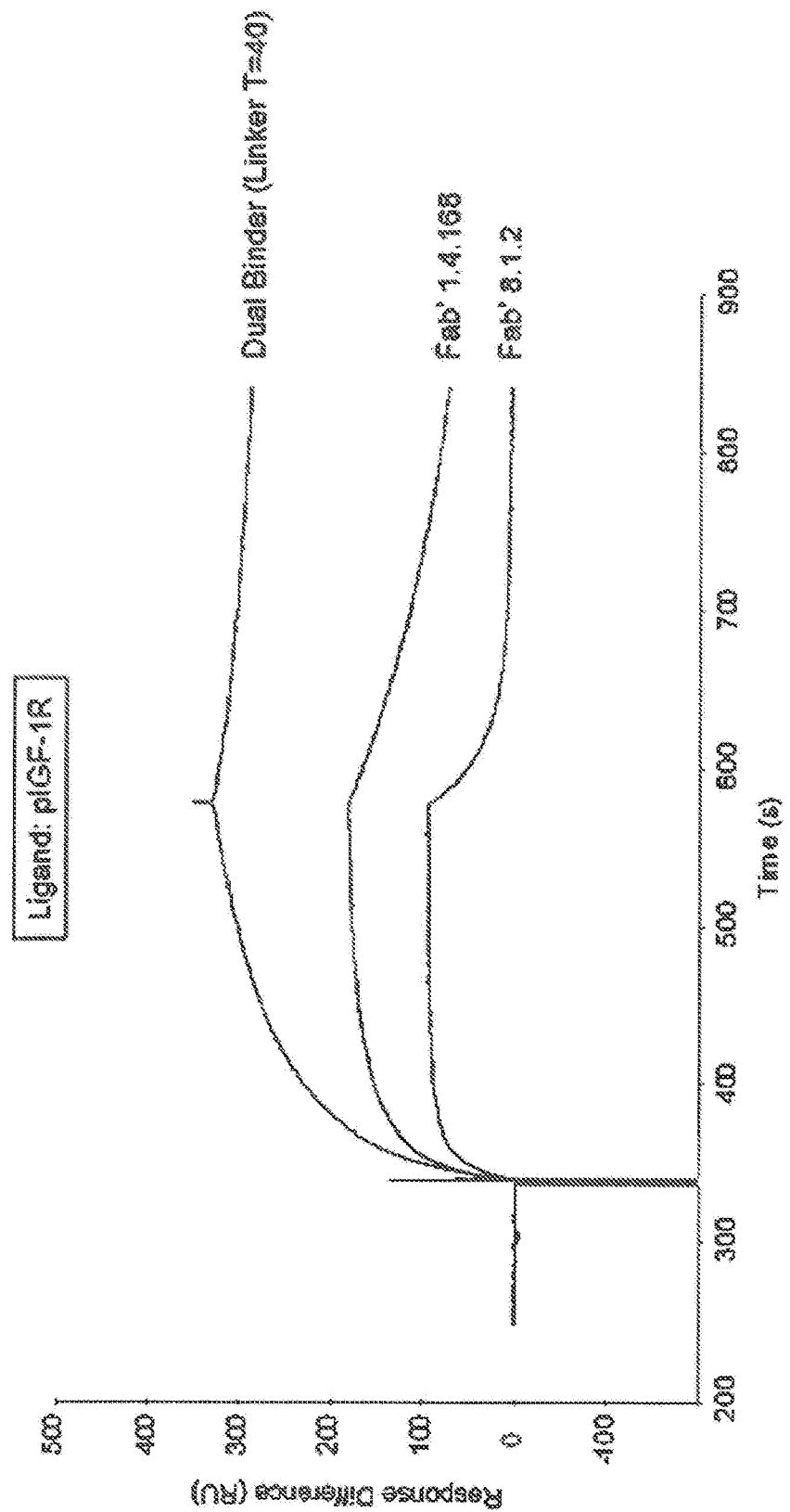
FIG. 3 shows a BIACORE™ sensorgram with overlay plot of three kinetics showing the interaction of 100 nM bivalent binding agent (consisting of ssFab' 8.1.2 and ssFab' 1.4.168 hybridized on the T40-T-Dig ssDNA-linker, i.e. linker 15) with the immobilized peptide pIGF-1R compared to the binding characteristics of 100 nM ssFab' 1.4.168 or 100 nM ssFab' 8.1.2 to the same peptide. Highest binding performance is obtained with the dual binder construct, clearly showing, that the cooperative binding effect of the dual binder increases affinity versus the target peptide pIGF-1R
Figure 4:
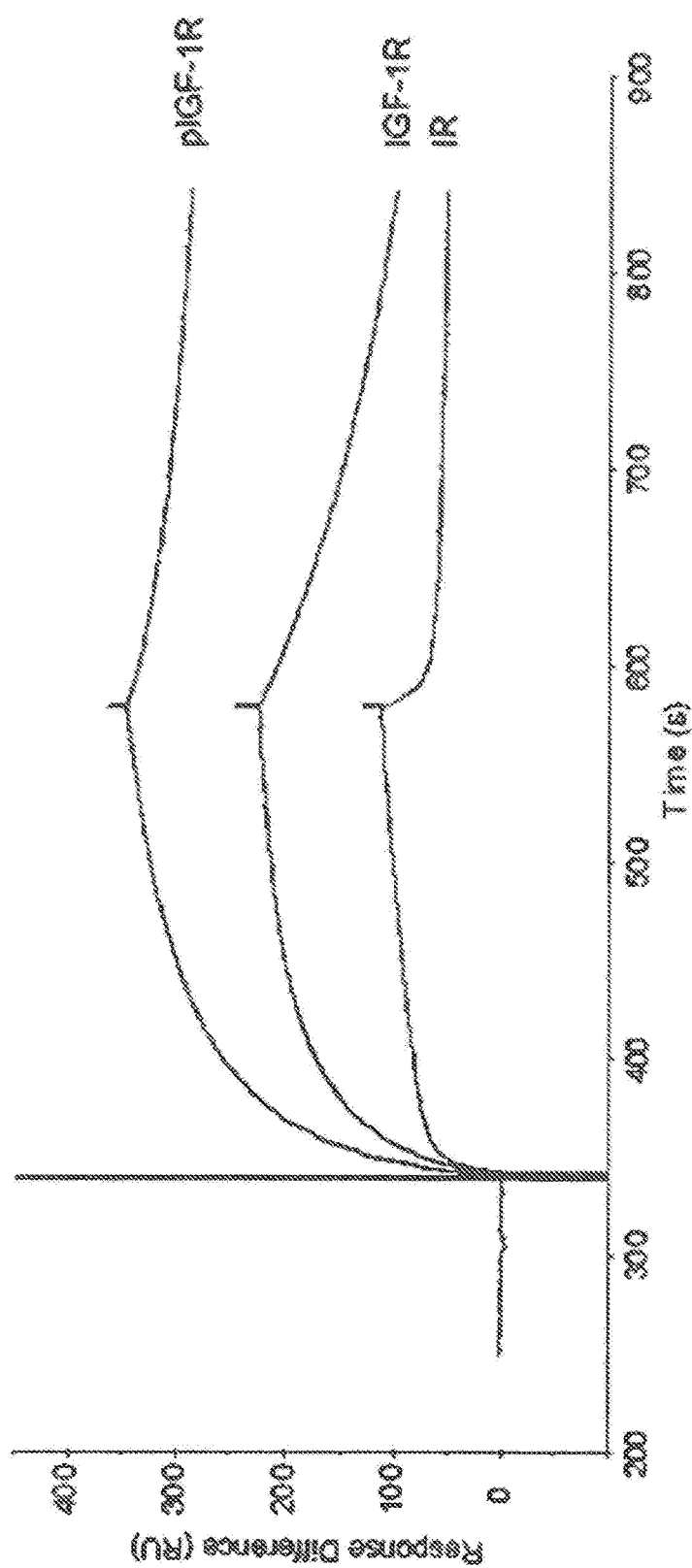
FIG. 4 is a BIACORE™ sensorgram with overlay plot of three kinetics showing the interactions of the bivalent binding agent consisting of ssFab' 8.1.2 and ssFab' 1.4.168 hybridized on the T40-T-Dig ssDNA-linker, i.e. linker 15, with immobilized peptides pIGF-1R (phosphorylated IGF-1R), IGF-1R or pIR (phosphorylated insulin receptor). Highest binding performance is obtained with the pIGF-1R peptide, clearly showing, that the cooperative binding effect of the dual binder increases specificity versus the target peptide pIGF-1R as compared to e.g. the phosphorylated insulin receptor peptide (pIR).
Figure 5:
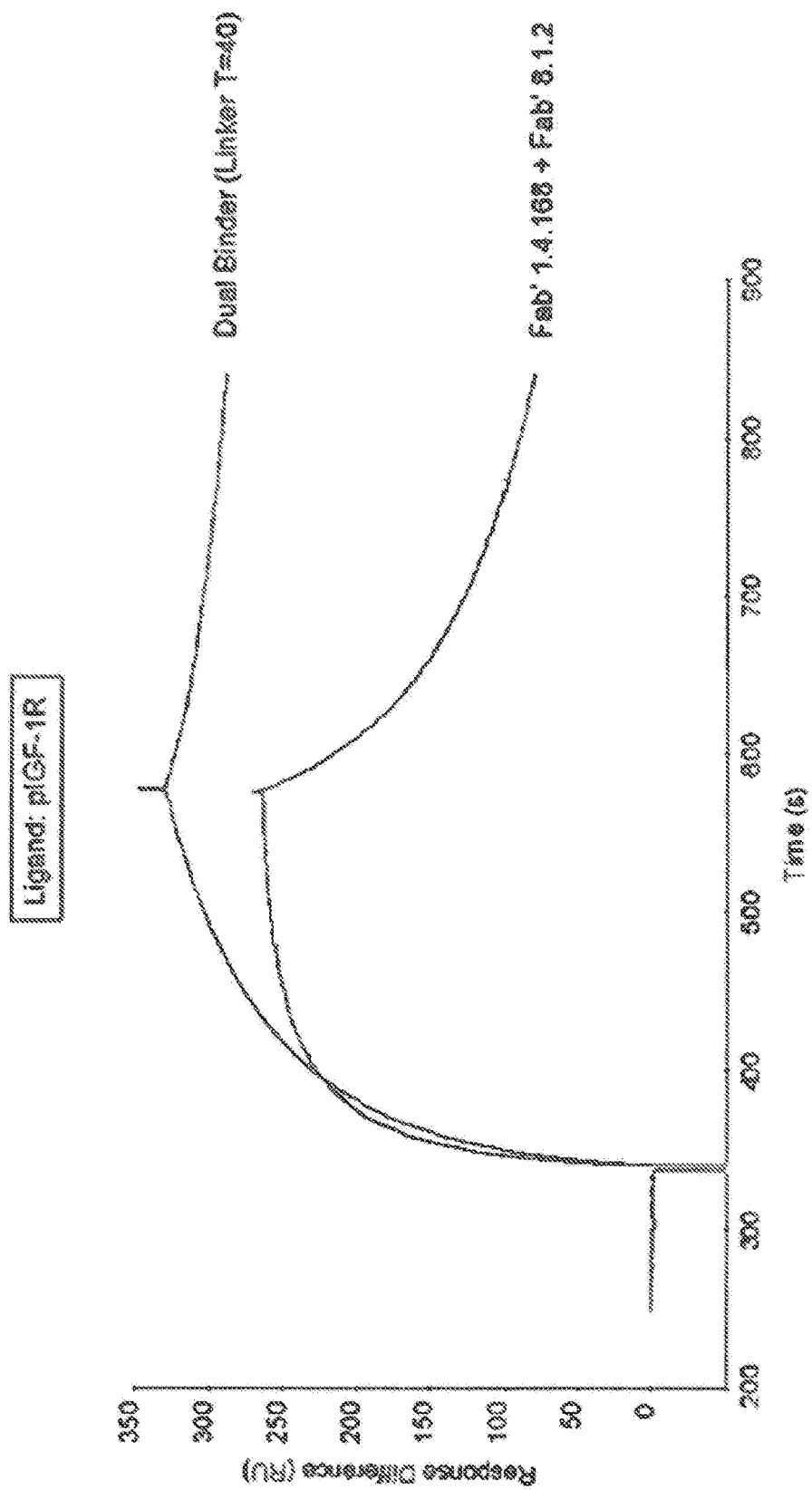
FIG. 5 is a BIACORE™ sensorgram with overlay plot of two kinetics showing the interactions of 100 nM bivalent binding agent consisting of ssFab' 8.1.2 and ssFab' 1.4.168 hybridized on the T40-T-Dig ssDNA-linker, i.e. linker 15, and a mixture of 100 nM ssFab' 8.1.2 and 100 nM ssFab' 1.4.168 without linker DNA. Best binding performance is only obtained with the bivalent binding agent, whereas the mixture of the ssFab's without linker doesn't show an observable cooperative binding effect, despite the fact that the total concentration of these ssFab's had been at 200 nM.

The sensorgrams (FIG. 2-5) show a gain in both specificity and complex stability in pIGF-1R binding when ssFab' 1.4.168 and ssFab' 1.4.168 are used in form of a dual binder (=bivalent binding agent), probably due to the underlying cooperative binding effect. Fab' 1.4.168 alone shows no cross reactivity for the pIR peptide but does not discriminate between the phosphorylated and unphosphorylated form of IGF-1R (T1/2 dis=3 min in both cases). Fab' 8.1.2, however, binds only to the phosphorylated version of the IGF1-R peptide but exhibits some undesired cross reactivity with phosphorylated Insulin Receptor. The dual binder discriminates well between the pIGF-1R peptide and both other peptides (see FIG. 4) and thus helps to overcome issues of unspecific binding. Note that the gain in specificity is lost when both Fab's are applied without linker DNA (FIG. 5). The gain in affinity of the dual binder towards the pIGF-1R peptide manifests in increased dissociation half times compared to individual Fab's and the Fab' mix omitting the linker DNA (FIG. 3 and FIG. 5). Although the tested dual binders with two different DNA linker lengths share an overall positive effect on target binding specificity and affinity, the longer linker ((III) with T40-T-Dig as a spacer) (i.e. linker 15 of example 2.4) seems to be advantageous with respect to both criteria.

2.7 BIACORE™ Assay Sandwich of M-1.4.168-IgG and M-8.1.2-IgG

A BIACORE™ T100 instrument (GE Healthcare) was used with a BIACORE™ CM5 sensor mounted into the system. The sensor was preconditioned by a 1 min injection at 100 μl/min of 0.1% SDS, 50 mM NaOH, 10 mM HCl and 100 mM H3PO4.

The system buffer was HBS-ET (10 mM HEPES pH 7.4, 150 mM NaCl, 1 mM EDTA, 0.05% TWEEN® 20). The sample buffer was the system buffer.

The BIACORE™ T100 System was driven under the control software V1.1.1. Polyclonal rabbit IgG antibody <IgGFCγM>R (Jackson ImmunoResearch Laboratories Inc.) at 30 μg/ml in 10 mM Na-Acetate pH 4.5 was immobilized at 10 000 RU on the flow cells 1, 2, 3, and 4, respectively, via EDC/NHS chemistry according to the manufacturer's instructions. Finally, the sensor surface was blocked with 1M ethanolamine. The complete experiment was driven at 13° C.

500 nM primary mAb M-1.004.168-IgG was captured for 1 min at 10 μl/min on the <IgGFCγM>R surface. 3 μM of an IgG fragment mixture (of IgG classes IgG1, IgG2a, IgG2b, IgG3) containing blocking solution was injected at 30 μl/min for 5 min. The peptide IGF-1R(1340-1366)[1346-pTyr; Glu(Bi-PEG-1340]amid was injected at 300 nM for 3 min at 30 μl/min. 300 nM secondary antibody M-8.1.2-IgG was injected at 30 μl min. The sensor was regenerated using 10 mM Glycine-HCl pH 1.7 at 50 μl/min for 3 min.

Figure 6:
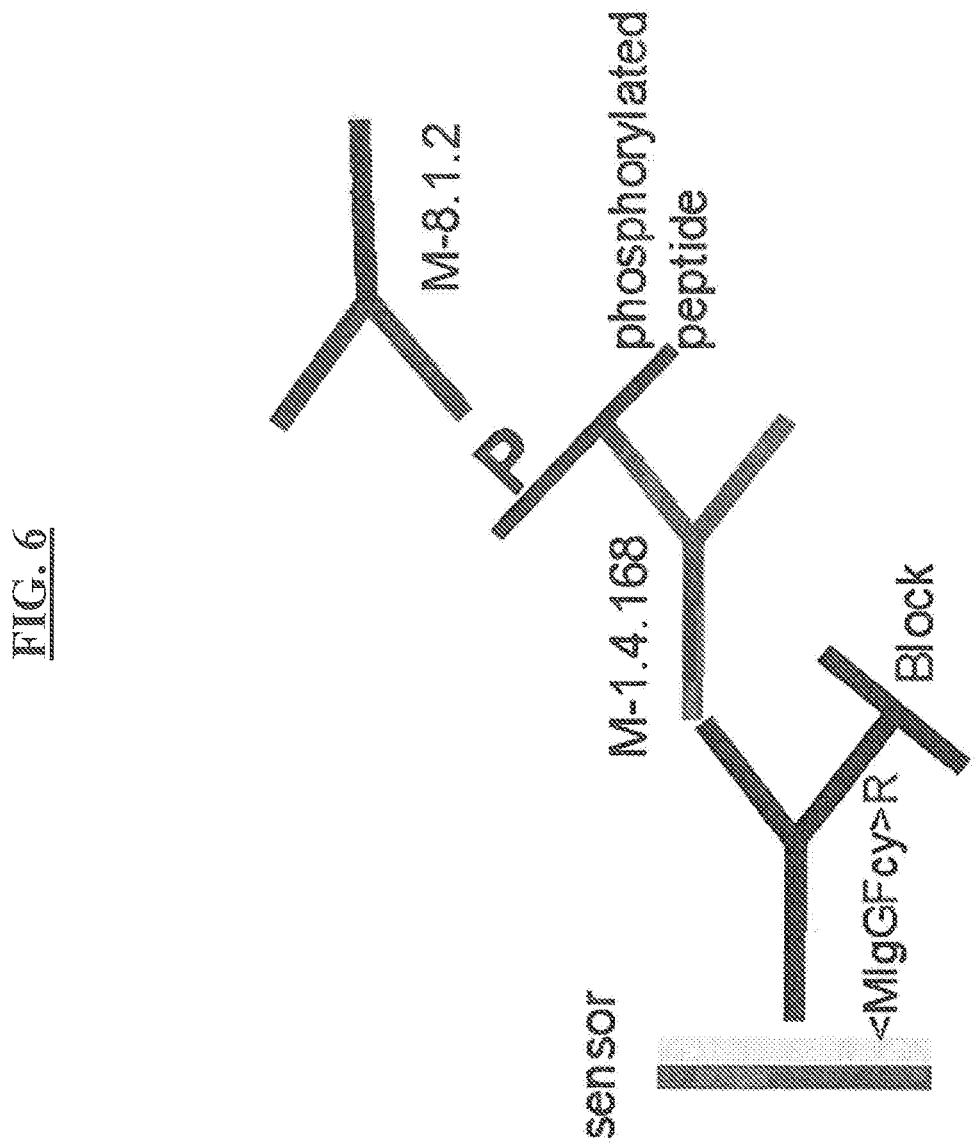
FIG. 6 is a schematic drawing of a BIACORE™ sandwich assay. This assay has been used to investigate the epitope accessibility for both antibodies on the phosphorylated IGF-1R peptide. <MIgGFcy>R presents a rabbit anti-mouse antibody used to capture the murine antibody M-1.4.168. M-1.4.168 then is used to capture the pIGF-1R peptide. M-8.1.2 finally forms the sandwich consisting of M-1.4.168, the peptide and M-8.1.2
Figure 7:
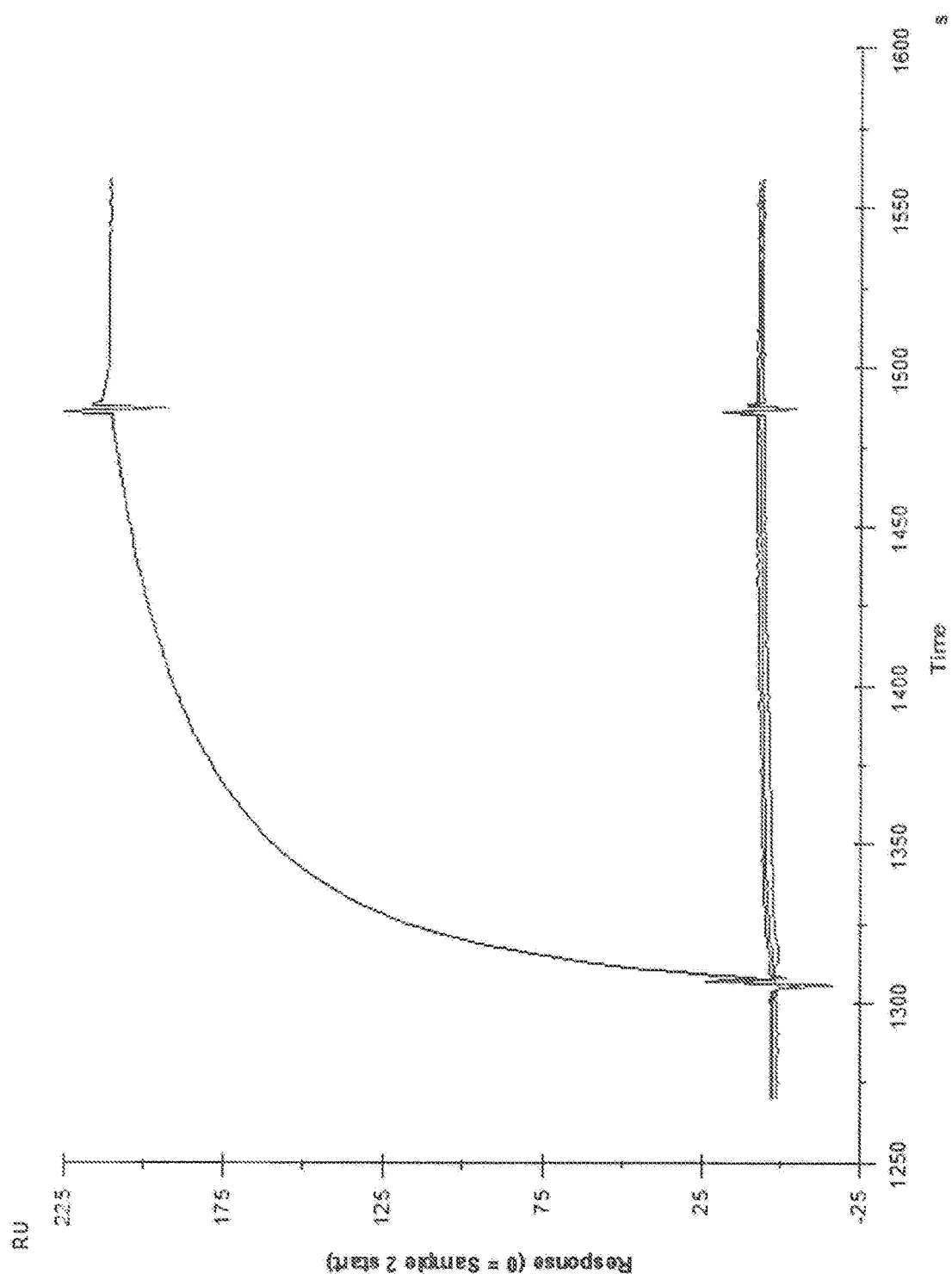
FIG. 7 is a BIACORE™ sensorgram showing the binding signal (thick line) of the secondary antibody 8.1.2. to the pIGF-1R peptide after this was captured by antibody 1.4.168 on the BIACORE™ chip. The other signals (thin lines) are control signals: given are the lines from top to bottom 500 nM 8.1.2, 500 nM 1.4.168; 500 nM target unrelated antibody <CKMM>M-33-IgG; and 500 nM target unrelated control antibody <TSH>M-1.20-IgG, respectively. No binding event could be detected in any of these controls

FIG. 6 describes the assay setup. In FIG. 7. the measurement results are given. The measurements clearly indicate, that both monoclonal antibodies are able to simultaneously bind two distinct, unrelated epitopes on their respective target peptide. This is a prerequisite to any latter experiments with the goal to generate cooperative binding events.

2.8 BIACORE™ Assay Dual Binder on Sensor Surface

A BIACORE™ 3000 instrument (GE Healthcare) was used with a BIACORE™ SA sensor mounted into the system at T=25° C. The system was preconditioned at 100 μl/min with 3×1 min injection of 1 M NaCl in 50 mM NaOH and 1 min 10 mM HCl.

The system buffer was HBS-ET (10 mM HEPES pH 7.4, 150 mM NaCl, 1 mM EDTA, 0.05% TWEEN® 20). The sample buffer was the system buffer.

The BIACORE™ 3000 System was driven under the control software V4.1.

124 RU amino-PEO-biotin were captured on the reference flow cell 1. 1595 RU biotinylated 14.6 kDa T0-Bi 37-mer ssDNA-Linker (I) (5'-G CAG AAG CAT TAA TAG ACT-T(-Bi)-TGG ACG ACG ATA GAA CT-3') (=linker 17 of example 2.4) and 1042 RU biotinylated 23.7 kDa T40-Bi 77-mer ssDNA-Linker (II) (5'-G CAG AAG CAT TAA TAG ACT-T(20)-(Biotin-dT)-(T20)-TGG ACG ACG ATA GAA CT-3'=linker 10 of example 2.4) were captured on different flow cells.

300 nM ssFab' 8.1.2 and 300 nM ssFab' 1.004.168 were injected into the system at 50 μl/min for 3 min. As a control only 300 nM ssFab' 8.1.2 or 300 nM ssFab' 1.004.168 was injected to test the kinetic contribution of each ssFab. As a control, buffer was injected instead of the ssFabs. The peptides pIR(1355-1382)[1361-pTyr]amid and IGF-1R (1340-1366)amid, respectively, were injected into system at 50 μl/min for 4 min, free in solution, in concentration steps of 0 nM, 4 nM, 11 nM, 33 nM (twice), 100 nM and 300 nM. In another set of experiments to measure the affinities versus peptide pIGF-1R(1340-1366)[1346-pTyr]amid the concentration steps of 0 nM, 0.4 nM, 1.1 nM, 3.3 nM (twice), 10 nM and 30 nM were used.

The dissociation was monitored at 50 µl/min for 5.3 min. The system was regenerated after each concentration step with a 12 sec pulse of 250 mM NaOH and was reloaded with ssFab' ligand.

Figure 8:
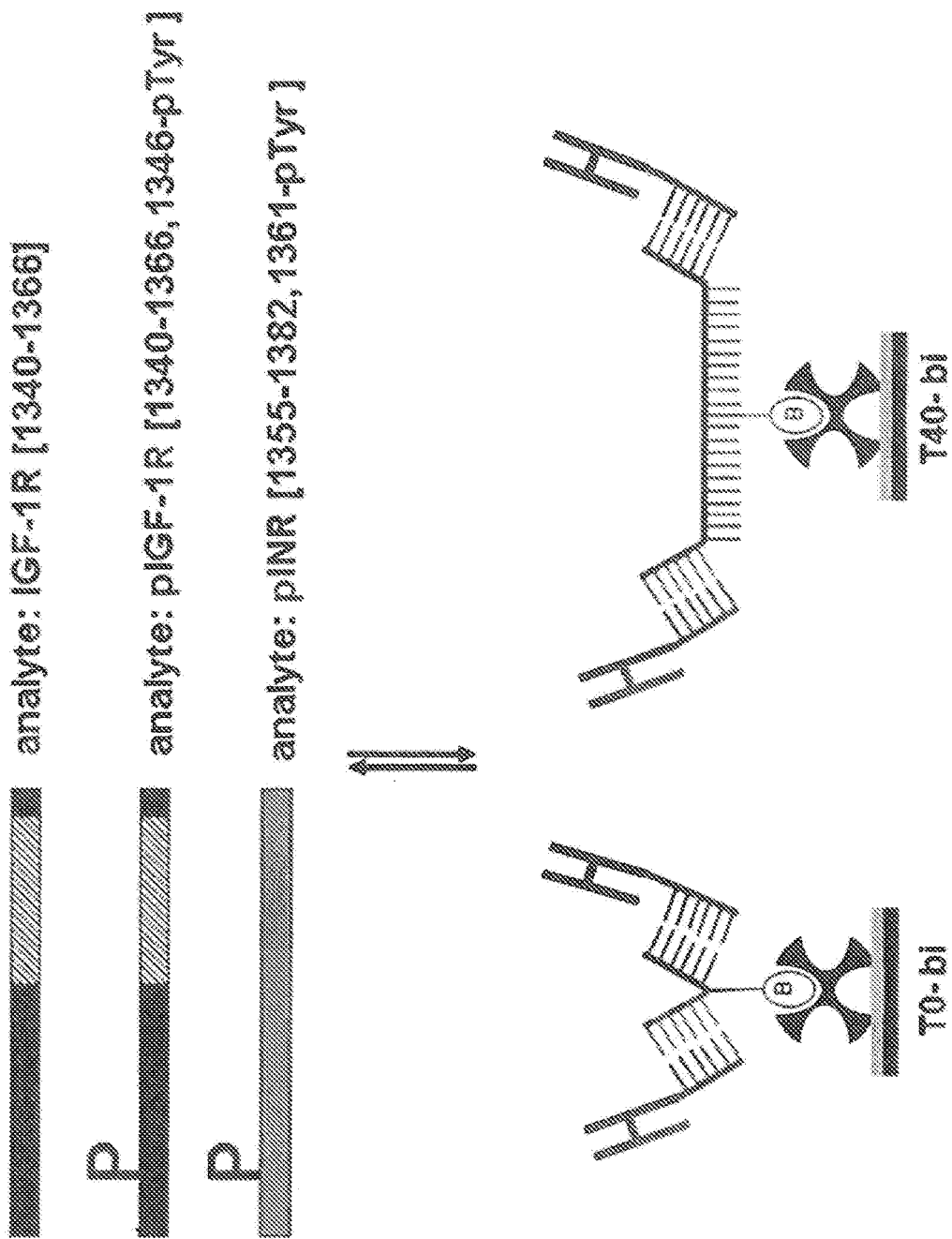
FIG. 8 is a schematic drawing of the BIACORE™ assay, presenting the biotinylated dual binders on the sensor surface. On Flow Cell 1 (=FC1) (not shown) amino-PEO-biotin was captured. On FC2, FC3 and FC4 bivalent binding agents with increasing linker length were immobilized (shown are the dual binders on FC2 (T0-bi=only one central T-Bi) and FC4 (T40-bi=one central T-Bi and 20 Ts each up- and downstream), respectively). Analyte 1: IGF-1R-peptide containing the M-1.4.168 ssFab' epitope at the right hand end of the peptide (top line)—the M-8.1.2 ssFab' phospho-epitope is not present, because this peptide is not phosphorylated; analyte 2: pIGF-1R peptide containing the M-8.1.2 ssFab' phospho-epitope (P) and the M-1.4.168 ssFab' epitope (second line); analyte 3: pIR peptide, containing the cross reacting M-8.1.2 ssFab' phospho-epitope, but not the epitope for M-1.4.168 (third line)
Figure 10:
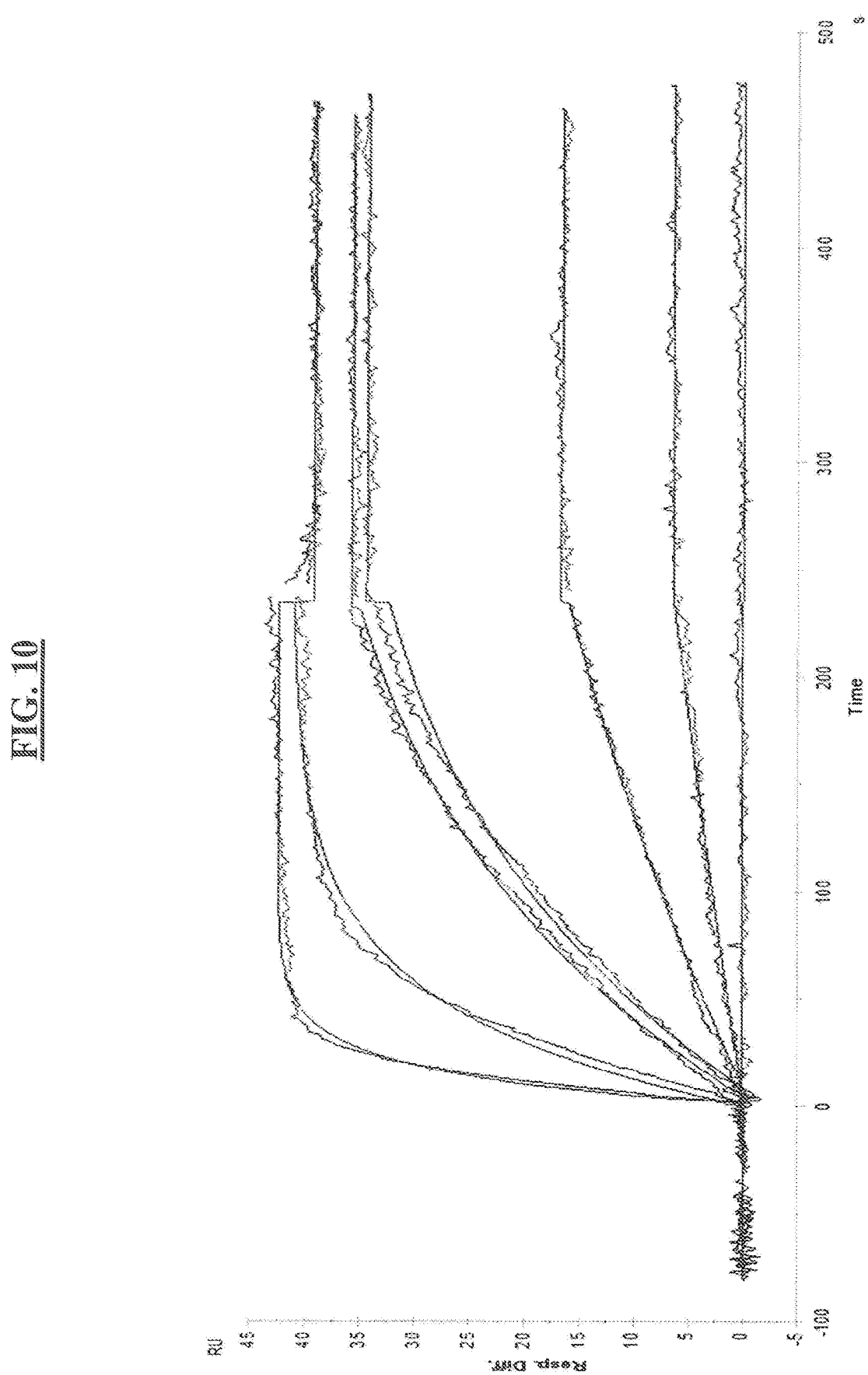
FIG. 10 is a BIACORE™ sensorgram, showing concentration dependent measurement of the T40-T-Bi dual binding agent vs. the pIGF-1R peptide (the phosphorylated IGF-1R peptide). The assay setup was as depicted in FIG. 8. A concentration series of the pIGF-1R peptide was injected at 30 nM, 10 nM, 2×3.3 nM, 1.1 nM, 0.4 nM, 0 nM. The corresponding data are given in the table of FIG. 9
Figure 11:
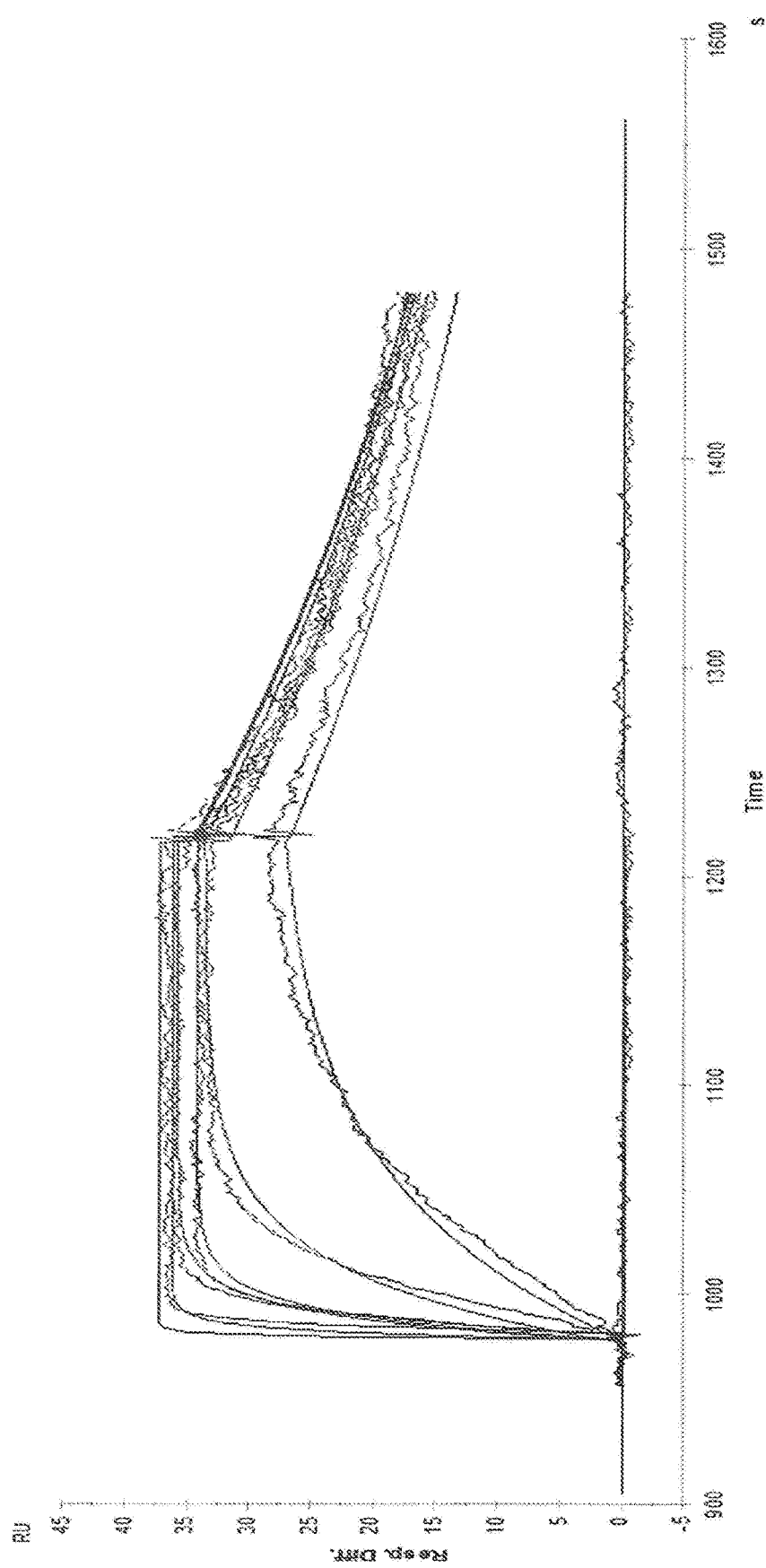
FIG. 11 is a BIACORE™ sensorgram, showing concentration dependent measurement of the T40-T-Bi dual binding agent vs. the IGF-1R peptide (the non-phosphorylated IGF-1R peptide). The assay setup was as depicted in FIG. 8. A concentration series of the IGF-1R peptide was injected at 300 nM, 100 nM, 2×33 nM, 11 nM, 4 nM, 0 nM. The corresponding data are given in the table of FIG. 9
Figure 12:
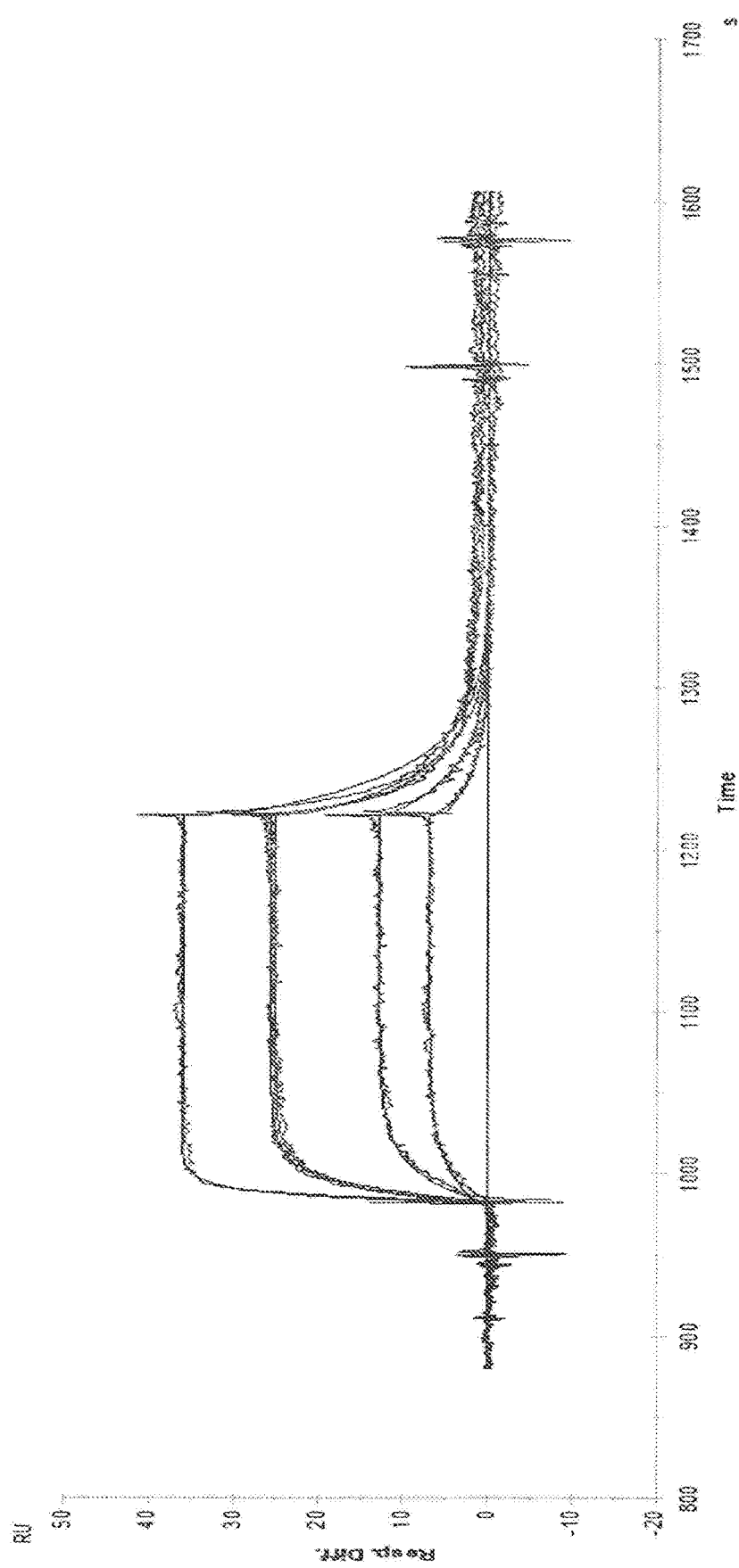
FIG. 12 is a BIACORE™ sensorgram, showing concentration dependent measurement of the T40-T-Bi dual binding agent vs. the pIR peptide (the phosphorylated insulin receptor peptide). The assay setup was as depicted in FIG. 8. A concentration series of the pIR peptide was injected at 100 nM, 2×33 nM, 11 nM, 4 nM, 0 nM. The corresponding data are given in the table of FIG. 9

FIG. 8 schematically describes the assay setup on the BIACORE™ instrument. The table given in FIG. 9 shows the quantification results from this approach. FIGS. 10, 11 and 12 depict exemplary BIACORE™ results from this assay setup using the T40 dual binding agent.

The table in FIG. 9 demonstrates the benefits of the dual binder concept. The T40 dual binding agent (a dual binding agent with linker 10 of example 2.4, i.e. a linker with a spacer of T20-Biotin-dT-T20) results in a 2-fold improved antigen complex halftime (414 min) and a 3-fold improved affinity (10 pM) as compared to the T0 dual binding agent (i.e. a dual binding agent with linker 16 of example 2.4) with 192 min and 30 pM, respectively. This underlines the necessity to optimize the linker length to generate the optimal cooperative binding effect.

The T40 dual binding agent (i.e. the dual binding agent comprising the T40-Bi linker (linker 10 of example 2.4)) exhibits a 10 pM affinity versus the phosphorylated IGF-1R peptide (table in FIG. 9, FIG. 10). This is a 2400-fold affinity improvement versus the phosphorylated insulin receptor peptide (24 nM) and a 100-fold improvement versus the non-phosphorylated IGF-1R peptide.

Therefore, the goal to increase specificity and affinity by the combination of two distinct and separated binding events is achieved.

The cooperative binding effect especially becomes obvious from the dissociation rates against the phosphorylated IGF-1R peptide, where the dual binder shows 414 min antigen complex halftime, versus 0.5 min with the monovalent binder 8.1.2 alone and versus 3 min with the monovalent binder 1.4.168 alone, respectively.

Furthermore, the fully assembled construct roughly multiplies its dissociation rates kd (1/s), when compared to the singly Fab' hybridized constructs (FIGS. 10, 11, 12 and table in FIG. 9). Interestingly, also the association rate ka (1/Ms) slightly increases when compared to the single Fab' interaction events, this may be due to an increase of the construct's molecular flexibility.

A diagnostic system using an intense washing procedure should definitely foster the high performance of the T40 dual binding agent, in contrast to individual (monovalent) Fab' molecules. The hybridized construct, i.e. a bivalent binding agent according to the present embodiment, generates a specific and quite stable binding event, while the monovalent binders more rapidly dissociate, e.g. they are more rapidly washed away.

2.9 Evaluation of an Anti-pIGF-1R Dual Binder Molecule in Immunohistochemistry (INC) Experiments:

The here described IHC experiments were performed on the BENCHMARK® XT platform from Ventana. For the assay an anti-pIGF-1R dual binder was used that consisted of ssFab' 1.4.168 (binding a non-phospho epitope of the intracellular domain of IGF-1R), ssFab' 30.4.33 (binding the pTyr1346 phospho-epitope of the intracellular domain of IGF-1R) and a flexible linker. The generation of antibody 1.4.168 has been described in Example 2.1 and antibody 30.4.33 (variable region heavy chain shown in SEQ ID NO:19 and variable region light chain shown in SEQ ID NO:20, respectively) has been produced using the same procedures as described there. The Fab'-fragment of 30.4.33 has a higher affinity towards the pTyr 1346 IGF-1R phosphorylation site than the previously used Fab'-fragment of antibody 8.1.2 (T1/2 diss of ssFab' 8.1.2 ~0.5 min, T1/2 diss of ssFab' 30.4.33 ~7 min).

Flexible linkers with spacers of different length (=linker 11, 12, 13, 14 of example 2.4) were used in this assay. A biotin label within the linker molecule served as a detection tag for the streptavidin-based Ventana iVIEW DAB detection kit.

In order to test the specificity of the anti-pIGF-1R dual binder molecule an elaborate test system based on formalin-fixed paraffin-embedded (FFPE) 3T3 cells was used. 3T3 cells had been stably transfected with either IGF-1R or IR expression vectors. Cells were fixed with formalin and embedded in paraffin according to standard protocols. Prior to fixation cells were stimulated with 100 ng/ml of either IGF-1 or Insulin to induce IGF1-R or IR phosphorylation or were left untreated. Western blotting experiments (FIG. 13 A) proved successful stimulation of receptor phosphorylation.

0.5 µg/ml per ssFab' fragment of only ssFab' 1.4.168 or only ssFab' 30.4.33, respectively, and an equimolar amount of 8×C18 linker, as well as a mixture of both ssFab' fragments of ssFab' 1.4.168 and ssFab' 30.4.33 (both at 0.5 µg/ml) and an equimolar amount of 8×C18 linker, respectively, were used for detection. A biotin label within the linker molecule served as a detection tag for the streptavidin-based Ventana iVIEW DAB detection kit. BENCHMARK® protocol details: pretreatment occurred with cell conditioning buffer 1 (CC1), the incubation time of the binding molecule was 32 min and the incubation temperature 37° C.

Figure 13A:
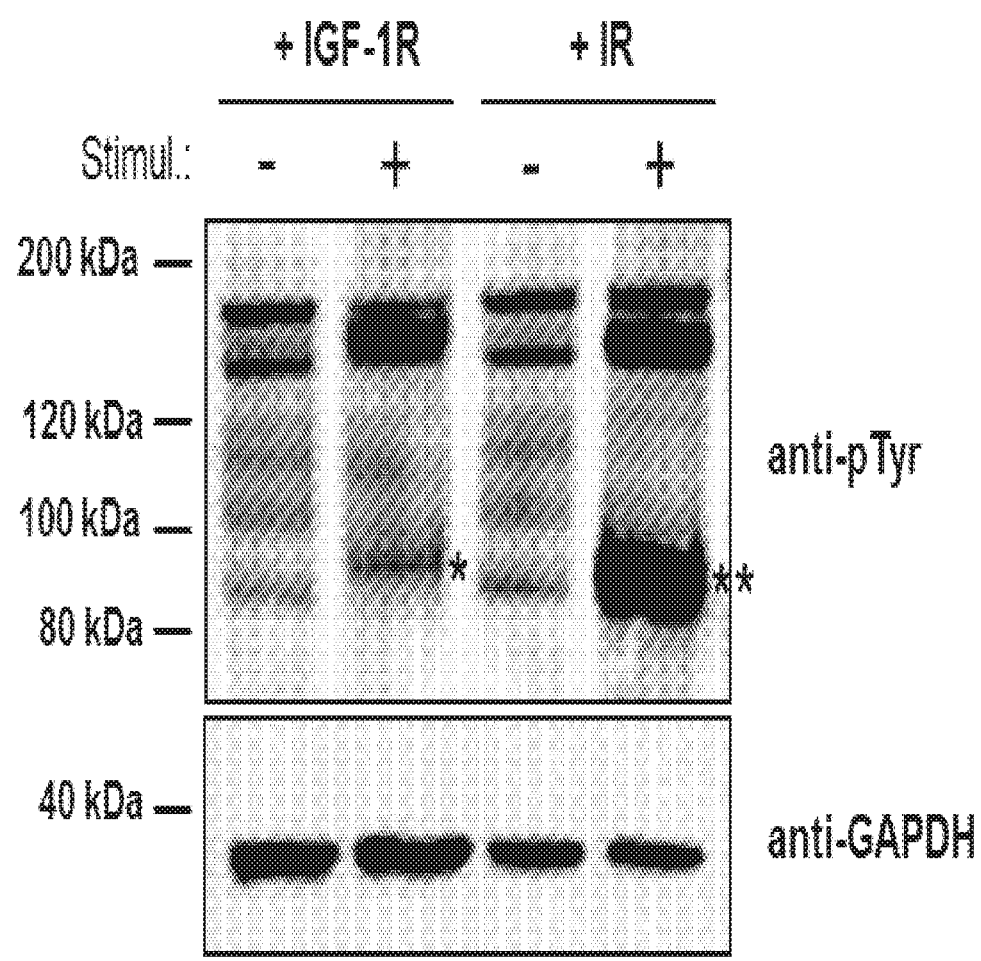
FIG. 13 A presents Western Blotting experiment with lysates of 3T3 cells that were used for the generation of formalin-fixed paraffin-embedded (FFPE) 3T3 cell pellets. 5 μg total protein of each lysate was subjected to SDS-PAGE and Western Blotting. Detection occurred with an anti-phosphotyrosine antibody (Millipore, clone 4G10). The asterisk (*) or the pair of asterisks (**) indicate the position of the bands for phosphorylated IGF-1R or phosphorylated IR proteins.
Figure 13:
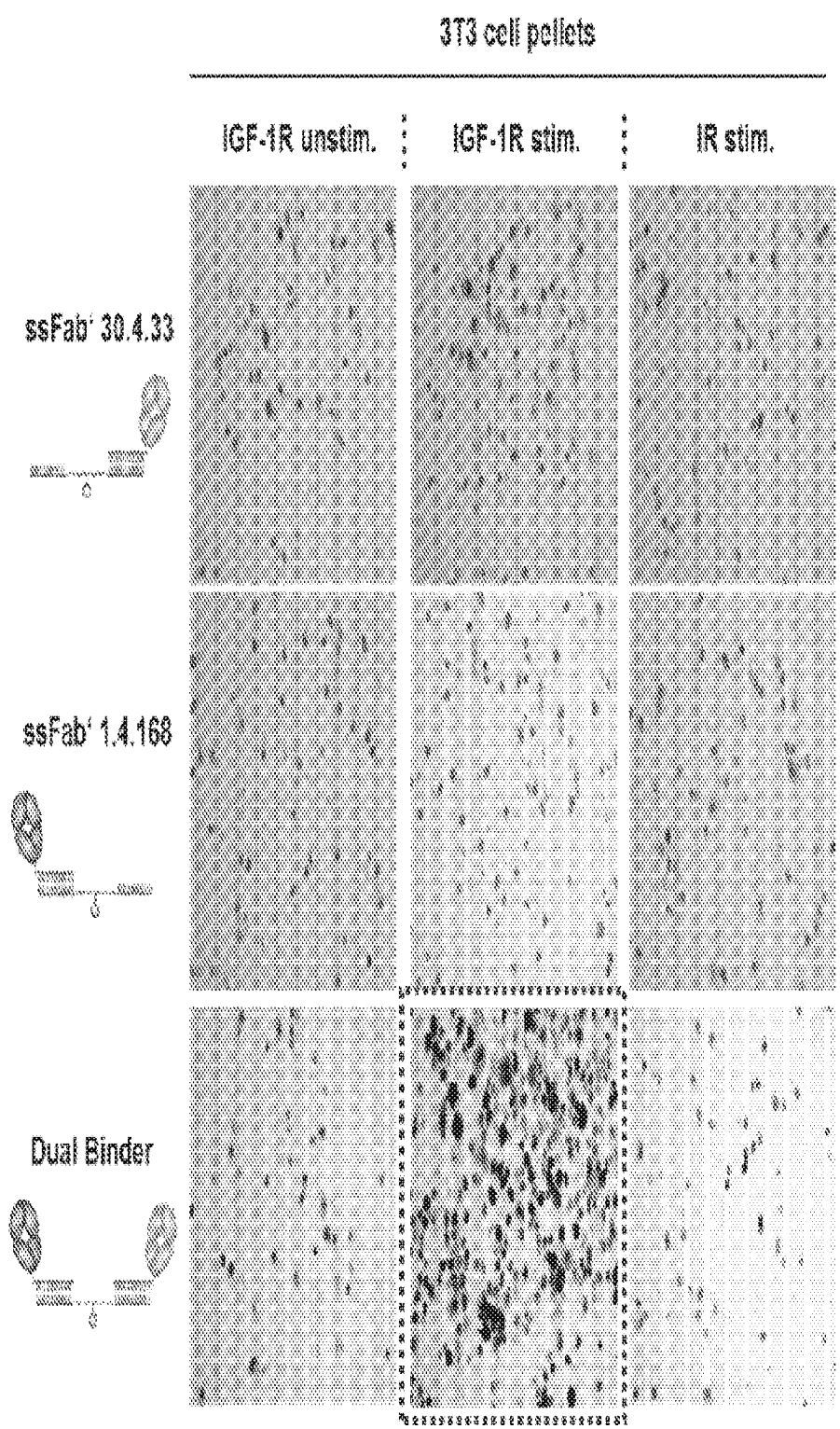
Figure 13:
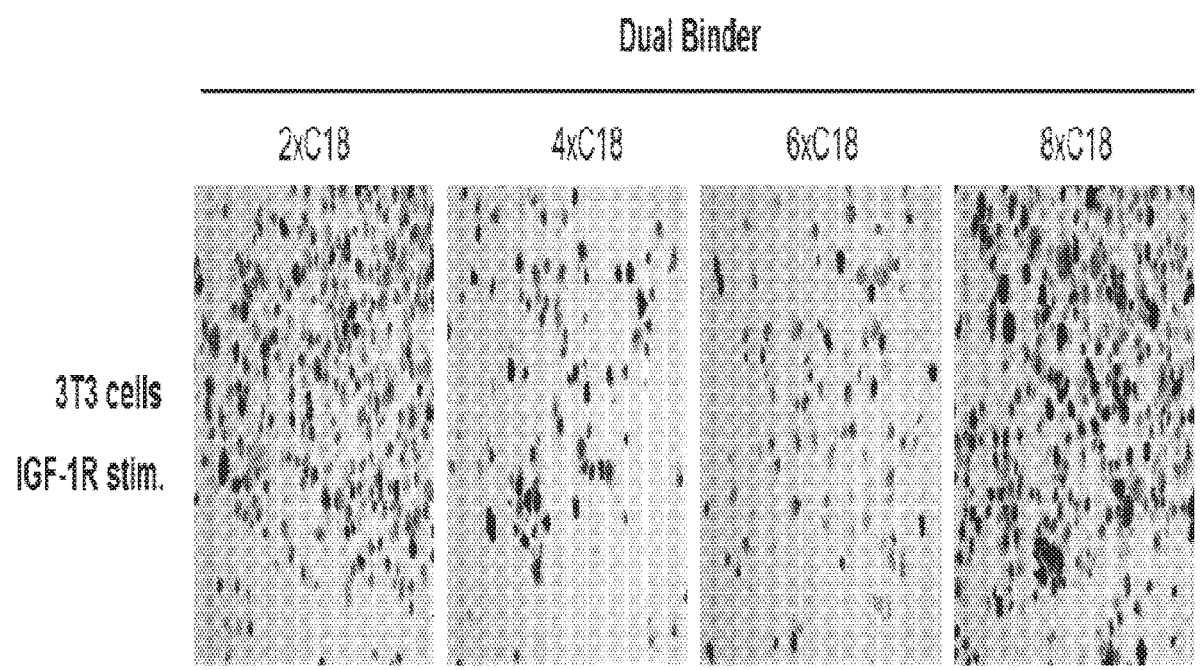

A detection molecule composed of an 8×C18 linker molecule (linker 14 of example 2.4) and only ssFab' 1.4.168 or only ssFab' 30.4.33 did not produce a staining on any of the tested FFPE 3T3 cell pellets (FIG. 13 B, rows 1&2). In contrast, detection with the full dual binder molecule (consisting of both ssFab' fragments+8×C18 linker) led to a staining—but only on IGF-1R overexpressing cells that were stimulated with IGF-1 (FIG. 13 B, row 3). No cross-reactivity was observed on cells overexpressing IR even when phosphorylation of IR had been induced. The experiment proves high specificity of the dual binder for phosphorylated IGF-1R.

In order to assess the influence of the linker length on staining performance 2×C18, 4×C18, 6×C18 and 8×C18 linker molecules (linker 11, 12, 13, 14 of example 2.4) have been used in the same IHC setup. Of the tested dual binders the one with the longest linker (8×C18) shows superior staining results (FIG. 13 C). This indicates that at least in this case a long flexible linker facilitates simultaneous binding of both dual binder arms to the two different epitopes on pIGF-1R.

The dual binder composed of ssFab' 1.4.168, ssFab' 30.4.33 and an 8×C18 linker molecule (linker 14 of example 2.4) was further tested on FFPE H322M xenograft tissue. BENCHMARK® protocol details: pretreatment occurred with cell conditioning buffer 1 (CC1), the incubation time of the binding molecule was 32 min and the incubation temperature 25° C. Again no pIGF-1R staining was observed with a detection molecule composed of the 8×C18 linker and only one of either ssFab' 1.4.168 or ssFab' 30.4.33. Detection with the full dual binder molecule (consisting of both ssFab' fragments+8×C18 linker), however, led to characteristic pIGF-1R membrane staining (FIG. 14).

2.10 BIACORE™ Assay Dual Binder on Sensor Surface

To obtain kinetic data also for the optimized version of the anti-pIGF-1R dual binder of Example 2.9 an additional BIACORE™ experiment was conducted.

A BIACORE™ 3000 instrument (GE Healthcare) was used with a BIACORE™ SA sensor mounted into the system at T=25° C. The system was preconditioned at 100 µl/min with 3×1 min injection of 1 M NaCl in 50 mM NaOH and 1 min 10 mM HCl.

The system buffer was HBS-ET (10 mM HEPES pH 7.4, 150 mM NaCl, 1 mM EDTA, 0.05% TWEEN® 20). The sample buffer was the system buffer.

The BIACORE™ 3000 System was driven under the control software V4.1.

89 RU amino-PEO-biotin were captured on the reference flow cell 1. 595 RU biotinylated 8×C18-Linker (I) (5'-G CAG AAG CAT TAA TAG ACT-(Spacer C18)4-(Biotin-dT)-(Spacer C18)4-TGG ACG ACG ATA GAA CT-3') (=linker 14 of example 2.4) were captured on a second flow cell.

300 nM ssFab' 30.4.33 and 300 nM ssFab 1.004.168 were injected into the system at 50 µl/min for 3 min. As a control only 300 nM ssFab' 30.4.33 or 300 nM ssFab' 1.004.168, respectively, was injected to test the kinetic contribution of each ssFab'. Peptide IGF-1R(1340-1366)[1346-pTyr]amid (the -1346 tyrosine phosphorylated-peptide of SEQ ID NO:11=synthetic analyte) was injected into system at 50 µl/min for 4 min, free in solution, in concentration steps of 0 nM, 0.4 nM, 1.1 nM, 3.3 nM (twice), 10 nM and 30 nM. The dissociation was monitored at 50 µl/min for 5.3 min. The system was regenerated after each concentration step with a 12 sec pulse of 250 mM NaOH and was reloaded with ssFab ligand.

As a further controls, a) buffer was injected instead of the ssFab's and b) a flow cell on which amino-PEO-biotin was immobilized has been used (data not shown). In these experiments no non-specific binding of the "analyte" was observed.

Figure 15:
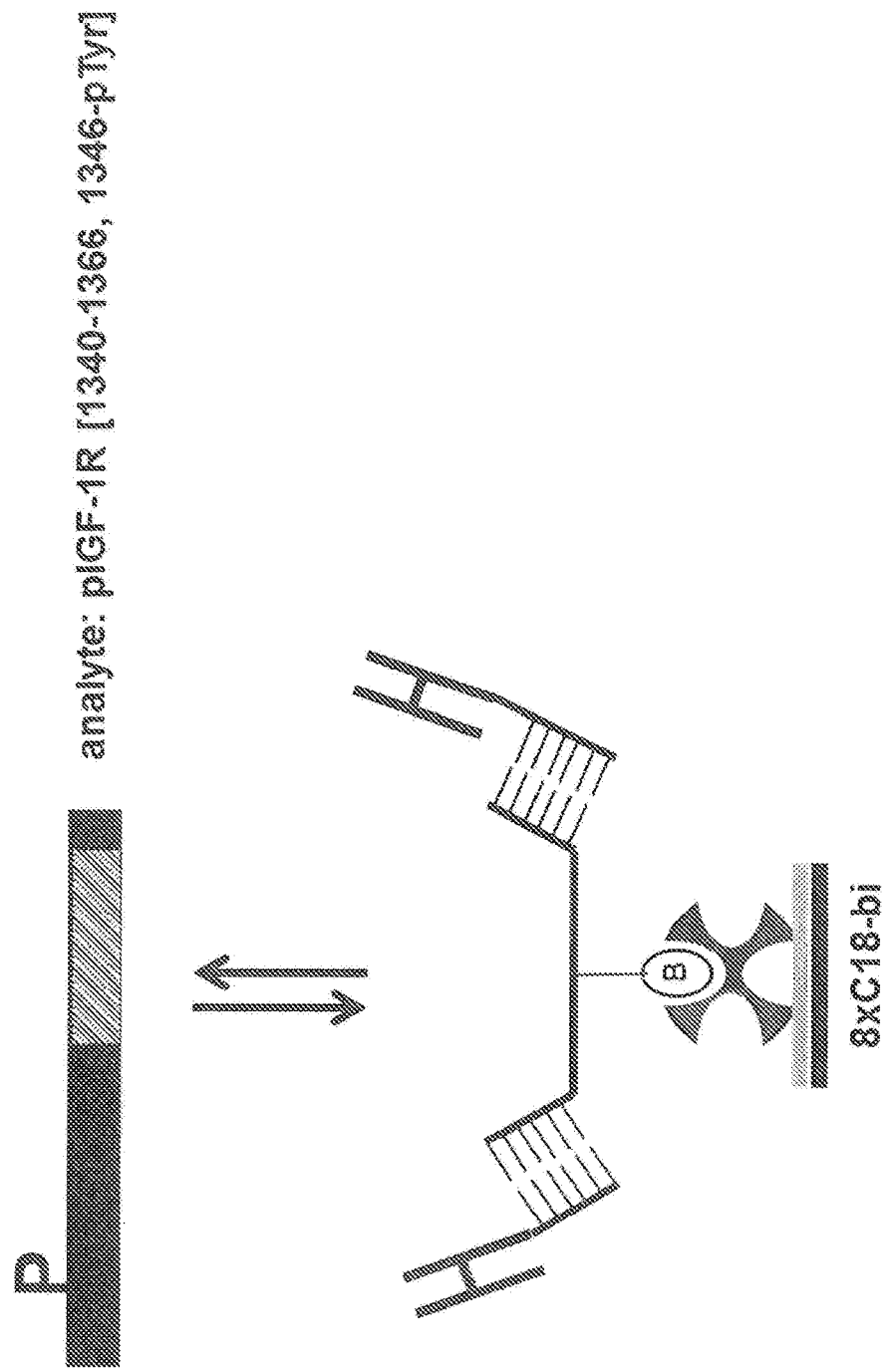
FIG. 15 is a schematic drawing of the BIACORE™ assay, presenting the biotinylated dual binders on the sensor surface An biotinylated 8×C18 linker molecule was immobilized that was used to capture ssFab' 1.4.168 and/or ssFab' 30.4.33, respectively. The analyte was a pIGF-1R-peptide containing the M-1.4.168 ssFab epitope at one end of the peptide and the M-30.4.33 ssFab phospho-epitope on the other end
Figure 17:
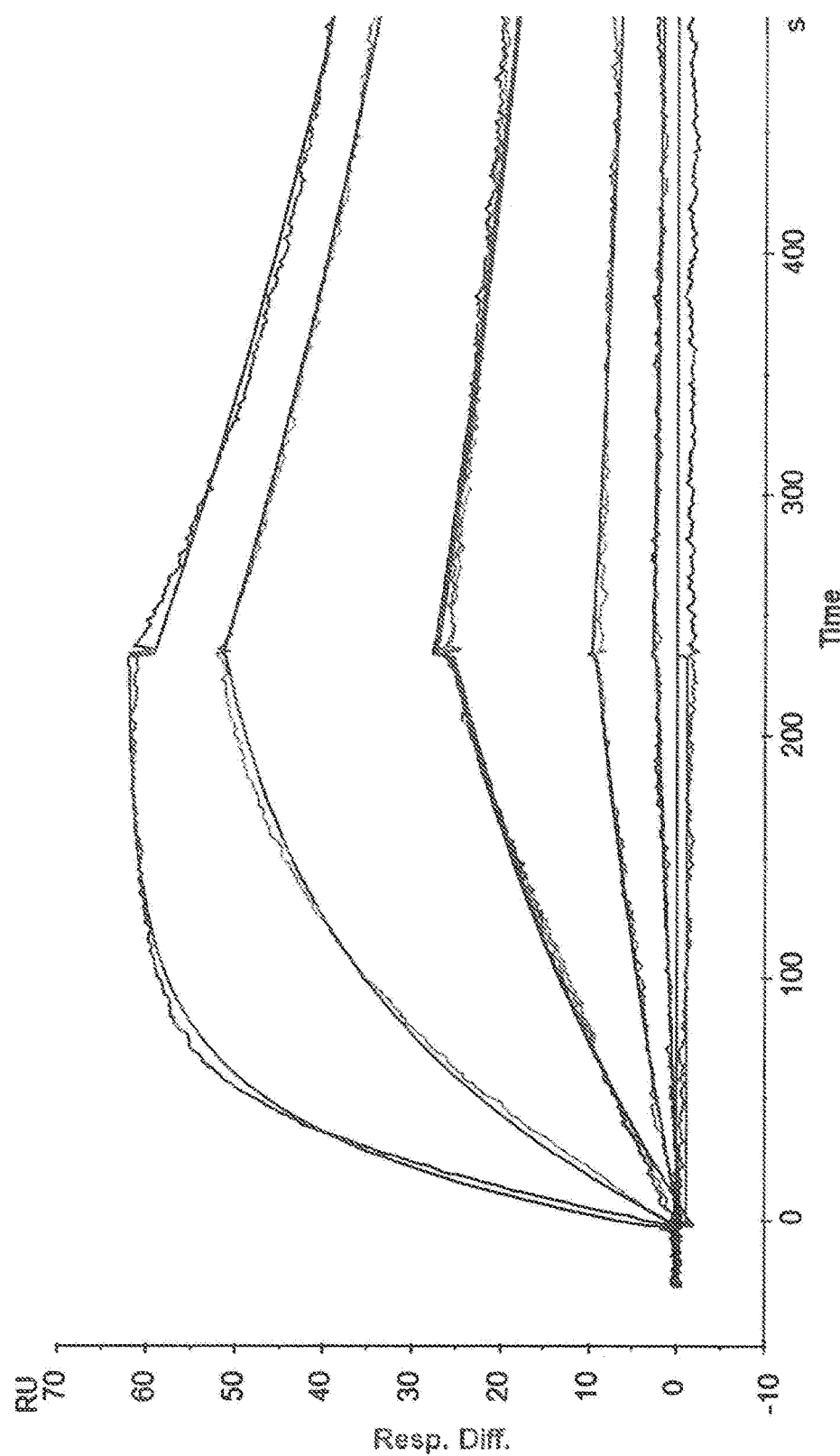
FIG. 17 is a BIACORE™ sensorgram, showing concentration dependent measurement of a monovalent binding agent composed of an 8×C18 linker molecule and ssFab' 30.4.33 versus the phosphorylated IGF-1R peptide. The assay setup was as depicted in FIG. 15. A concentration series of the synthetic, phosphorylated pIGF-1R peptide of SEQ ID NO:11 was injected at 30 nM, 10 nM, 2×3.3 nM, 1.1 nM, 0.4 nM, 0 nM. The corresponding kinetic data are given in FIG. 16
Figure 18:
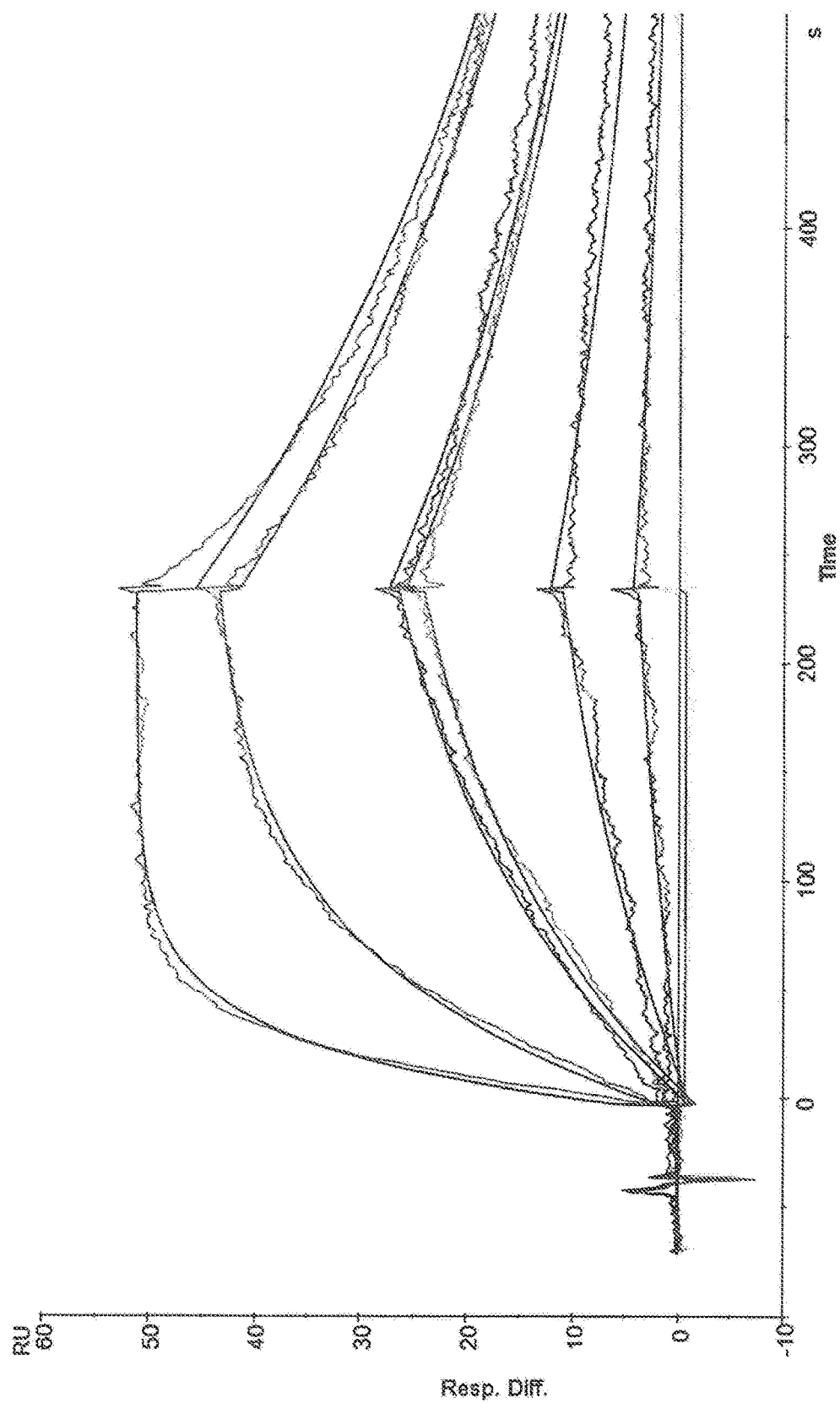
FIG. 18 is a BIACORE™ sensorgram, showing concentration dependent measurement of a monovalent binding agent composed of an 8×C18 linker molecule and ssFab' 1.4.168 versus the phosphorylated IGF-1R peptide. The assay setup was as depicted in FIG. 15. A concentration series of the pIGF-1R peptide was injected at 30 nM, 10 nM, 2×3.3 nM, 1.1 nM, 0.4 nM, 0 nM. The corresponding kinetic data are given in FIG. 16
Figure 19:
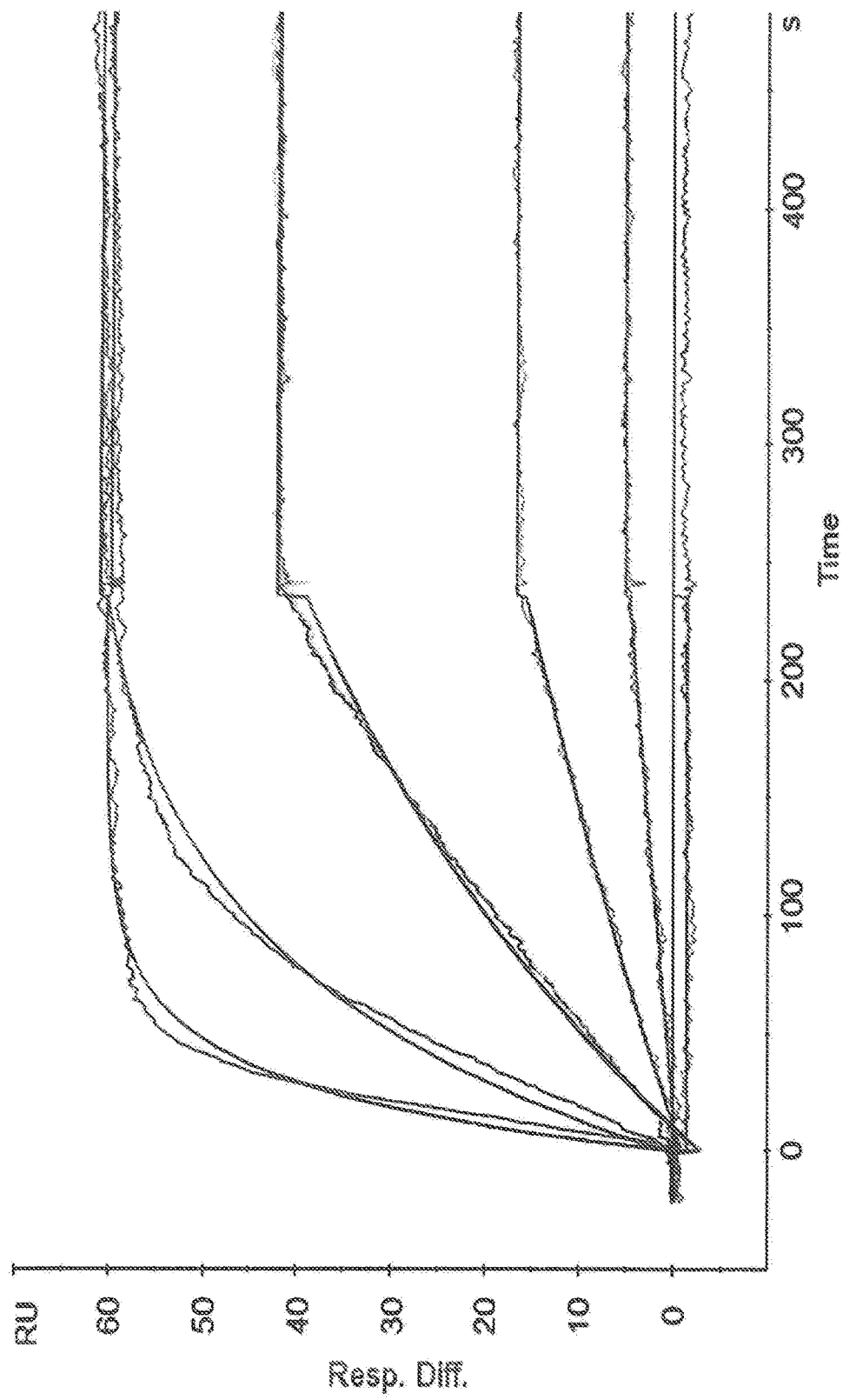
FIG. 19 is a BIACORE™ sensorgram, showing concentration dependent measurement of a bivalent binding agent composed of an 8×C18 linker molecule, ssFab' 30.4.33 and ssFab' 1.4.168 versus the phosphorylated IGF-1R peptide. The assay setup was as depicted in FIG. 15. A concentration series of the pIGF-1R peptide was injected at 30 nM, 10 nM, 2×3.3 nM, 1.1 nM, 0.4 nM, 0 nM. The corresponding kinetic data are given in FIG. 16

FIG. 15 schematically describes the assay setup on the BIACORE™ instrument. The table given in FIG. 16 shows the quantification results from this approach. FIGS. 17, 18 and 19 depict the BIACORE™ results from this assay setup.

As seen in FIG. 16 the dual binding molecule exhibits a ~10 pM affinity versus the phosphorylated, synthetic IGF-1R analyte. This is a 200-fold or 300-fold affinity improvement compared to a binding molecule that consists of ssFab' 30.4.33 or ssFab' 1.4.168 alone. The determined dissociation rates are 830 min for the dual binder, 7.3 min for the monovalent binder ssFab' 30.4.33 and 3.5 min for the monovalent binder ssFab' 1.4.168. These data clearly demonstrate the cooperative binding effect of the used dual binder molecule.

Example 3

Bivalent Binding Agent to Phosphorylated HER3

The receptor tyrosine kinase family of HER proteins consists of four members: HER1, HER2, HER3 and HER4. Upon ligand binding, the receptors dimerize as homo- or heterodimers in various ways to trigger different signal transduction pathways, depending on the ligand and the expression levels of each of the four family members. For example, HER3 undergoes a conformational shift when it is bound to its ligands Neuregulin1 (NRG1) or Neuregulin2 (NRG2) and the HER3 dimerization domain is exposed and it can interact with other HER receptors. Upon dimerization, HER3 becomes phosphorylated. In this example, we developed a dual binder to detect the phosphorylated form of HER3.

3.1 Monoclonal Antibody Development (mAb 7.2.32 and mAb 4.1.15)

a) Immunization of Mice

Balb/c and NMRI mice are immunized with HER3(1243-1267)[KLH-MP-Cys-UZU-1243]amide or pHER3(1283-1295)[pTyr1289; KLH-MP-Cys-UZU-1283]amide. The initial immunization dose is 100 µg. The mice are further immunized with 100 µg of the immunogen after 6 and 10 weeks.

b) Fusion and Cloning

Fusion and cloning steps were performed as described in 2.1 b)

c) Immunoglobulin Isolation from the Cell Culture Supernatants

Immunoglobulin isolation was performed as described in 2.1 c)

d) Biophysical Characterization of Monoclonal Antibodies

The kinetic properties of the interaction between the monoclonal antibodies and HER3 or the phosphorylated form of pHER3 are investigated by surface plasmon resonance kinetic screening using BIACORE™ technology.

A BIACORE™ A100 instrument under control of the software version V1.1 is used. A BIACORE™ CM5 chip is mounted into the instrument and is hydrodynamically addressed conditioned according to the manufacturer's instructions. As a running buffer an HBS-EP buffer is used (10 mM HEPES (pH 7.4), 150 mM NaCl, 1 mM EDTA, 0.05% (w/v) P20). A polyclonal rabbit anti-mouse IgG Fc capture antibody is immobilized at 30 µg/ml in 10 mM sodium acetate buffer (pH 4.5) to spots 1, 2, 4 and 5 in flow cells 1, 2, 3 and 4 at 10,000 RU. The antibody is covalently immobilized via NHS/EDC chemistry. The sensor is deactivated thereafter with a 1 M ethanolamine solution. Spots 1 and 5 are used for the determination and spots 2 and 4 are used as reference. Prior to application to the sensor chip the hybridoma supernatants containing mAbs are diluted 1:2 in HBS-EP buffer. The diluted solution is applied at a flow rate of 30 µl/min for 1 min. Immediately thereafter the analyte, human_HER3(1242-1267)-Bi-PEG-amide (SEQ ID NO:17), human pHER3(1283-1295[pTyr1289])-PEG2-EDA-Btn (SEQ ID NO:18) or human_HER3(1283-1295)-PEG2-EDA-Btn (SEQ ID NO:18), singly grafted on streptavidin, is injected at a flow rate of 30 µl/min for 2 min. Thereafter, the signal is recorded for 5 min dissociation time. The sensor is regenerated by injecting a 10 mM glycine-HCl solution (pH 1.7) for 2 min, at a flow rate of 30 µl/min. The dissociation rate constant kd (1/s) is calculated according to a Langmuir model using the evaluation software according to the manufacturer's instructions. The selected monoclonal antibodies interact with the HER3 epitope comprising amino acids 1242-1267 or with the phosphorylated (pTyr1289) HER3 epitope comprising amino acids 1283-1295 with a dissociation rate constant that lies within the boundaries of the patent claim. Antibodies that bound the unphosphorylated form of epitope HER3(1283-1295) were rejected from further studies.

The selected antibody directed against HER3(1242-1267) was called 7.2.32 (variable region heavy chain shown in SEQ ID NO:21 and variable region light chain shown in SEQ ID NO:22, respectively) and its dissociation rate constant was determined as $2.3 \times 10^{-3}$ 1/s and, consequently, within the necessary range required for the dual-binder approach. The selected antibody directed against pHER3

(1283-1295[pTyr1289]) was called 4.1.15 (variable region heavy chain shown in SEQ ID NO:23 and variable region light chain shown in SEQ ID NO:24, respectively) and the dissociation rate constant was $2.5 \times 10^{-3}$ 1/s, and thus, also within the defined range required for the dual-binder approach.

e) Sequencing of Variable Regions of Selected Antibodies

The variable regions of the selected antibodies were sequenced using standard molecular biology methods. Sequences are shown in SEQ ID NO:21-24.

3.2 Development of a Dual Binder Recognizing Phosphorylated HER3 (pTyr1289)

a) Recombinant Expression of Fab Fusion Proteins

Fab-fragments 7.2.32 and 4.1.15 were expressed in Hek293F cells as fusion proteins bearing an 8×HIS-Tag and a sortase cleavage recognition sequence (SEQ ID NO:16). 1 L $1 \times 10^6$ HEK 293 cells/ml with a viability of >90% were transfected in a ratio of 1:1 with the plasmids encoding the heavy chain and light chain of 7.2.32 or 4.1.15 using 293FECTIN™ Transfection Reagent (Invitrogen) according to the manufacturer's instructions. After transfection, the HEK293F cells were incubated for 7 days at 130 rpm, 37° C. and 8% $CO_2$. Cells were then centrifuged at 4° C., 8000 rpm for 20 min. The supernatant, containing the recombinant protein, was further filtered using a 0.22 µm STERI-FLIP® (Millipore) vacuum filtration system. Fab fragments were purified by Nickel affinity-column chromatography and preparative gel filtration using the ÄKTA EXPLORER FPLC system using standard purification methods. Purity was assessed by SDS-PAGE and analytical gel filtration.

a) DNA-Oligo Conjugation Using the Enzyme Sortase in a Transpeptidase Reaction

The enzyme sortase is a prokaryotic proteolytic enzyme that also has transpeptidase activity (Ton-That et al, PNAS 1999). Here, the enzyme catalyzes a transpeptidase reaction between an LPXTG a sortase cleavage motif and a glycine residue that is attached to a DNA-oligo. 17mer (oligo for 4.1.15 labeling shown in SEQ ID NO:25) and 19mer (oligo for 7.2.32 labeling shown in SEQ ID NO:26) oligos were used for the labeling reaction. The labeling was performed with 20 µM recombinant Sortase, 50 µM Fab fragment and 200 µM Oligo in a buffer of 20 mM Tris pH 8, 200 mM NaCl, 5 mM $CaCl_2$, at 37° C. overnight. Next, the labeling reaction is diluted 10 times in 20 mM Tris pH 8.0 and applied to a RESOURCE™ Q Q ion exchange column (GE Healthcare) which is equilibrated in 20 mM Tris pH 8.0. The strongly negatively charged Oligo and the Oligo-Fab fragments are eluted with a high salt gradient of 20 mM Tris pH 8.0 and 1M NaCl, and thus separated from the Sortase and the unlabeled Fab fragment that elute at a low salt concentration. The elution is monitored following the absorbance at 495 nm, detecting the fluorescein-label of the Oligo. The eluted fractions containing Oligo and Fab-Oligo are pooled and the Fab-Oligo is separated from the unconjugated Oligo by preparative gel filtration on a HiLoad 16/60 column SUPERDEX™ 200 column (GE Healthcare) using 20 mM Tris 8.0, 200 mM NaCl as equilibration and running buffer. The purity of the final product is assessed using analytical gel filtration and SDS-PAGE and only >90% pure end product will be used in the assembly of dual binders. In the following, a Fab-Oligo is referred to as "ssFab".

a) Assembly of an Anti-pHER3 Dual Binder.

The anti-pHER3 dual binder is based on an ssDNA linker molecule and two ssFab fragments that target different epitopes of the intracellular domain of HER3: ssFab 4.1.15 detects a phosphorylation site (pTyr 1289) and ssFab 7.2.32 a non-phospho site of the said target protein. Assembly evaluation was performed as described in 2.5.B. Experiments showed efficient assembly of the dual binder molecule.

3.3 Evaluation of an Anti-pHER3 Dual Binder Molecule in Immunohistochemistry (INC) Experiments:

The IHC experiments were performed on the BENCH-MARK® XT platform from Ventana. For the assay an anti-pHER3 dual binder was used that consisted of ssFab 7.2.32 (binding a non-phospho epitope of the intracellular domain of HER3), ssFab 4.1.15 (binding the pTyr1289 phospho-epitope of the intracellular domain of HER3) and a flexible linker. A flexible linker with a 4×C18 spacer (=linker 12 of example 2.4) was used in this assay. A biotin label within the linker molecule served as a detection tag for the streptavidin-based Ventana iVIEW DAB detection kit.

In order to test the specificity of the anti-pHER3 dual binder molecule an elaborate test system based on formalin-fixed paraffin-embedded (FFPE) Hek293 cells was used. Hek293 cells had been transiently transfected with both HER2 and HER3 expression vectors. In one case an HER3 expression vector was used that encodes an mutated version of HER3, in which 14 tyrosines of the intracellular domain that serve as phosphorylation sites are replaced with phenylalanines (Y975F, Y1054F, Y1132F, Y1159F, Y1197F, Y1199F, Y1222F, Y1224F, Y1260F, Y1262F, Y1276F, Y1289F, Y1307F, Y1328F). Cells were fixed with formalin and embedded in paraffin according to standard protocols. Prior to fixation, cells were stimulated with 20 nM NRG1-β1 (Peprotech) for 15 min at 37° C. to induce HER3 phosphorylation or were left untreated. Western blotting experiments (FIG. 20 A) proved successful stimulation of receptor phosphorylation.

1 µg/ml per ssFab fragment of only ssFab 7.2.32 or only ssFab 4.1.15, respectively, and an equimolar amount of 4×C18 linker, as well as a mixture of both ssFab' fragments of ssFab 7.2.32 and ssFab 4.1.15 (both at 1 µg/ml) and an equimolar amount of 4×C18 linker, respectively, were used for detection. A biotin label within the linker molecule served as a detection tag for the streptavidin-based Ventana iVIEW DAB detection kit. BENCHMARK® protocol details: pretreatment occurred with cell conditioning buffer 1 (CC1), the incubation time of the binding molecule was 32 min and the incubation temperature 37° C.

Figure 20A:
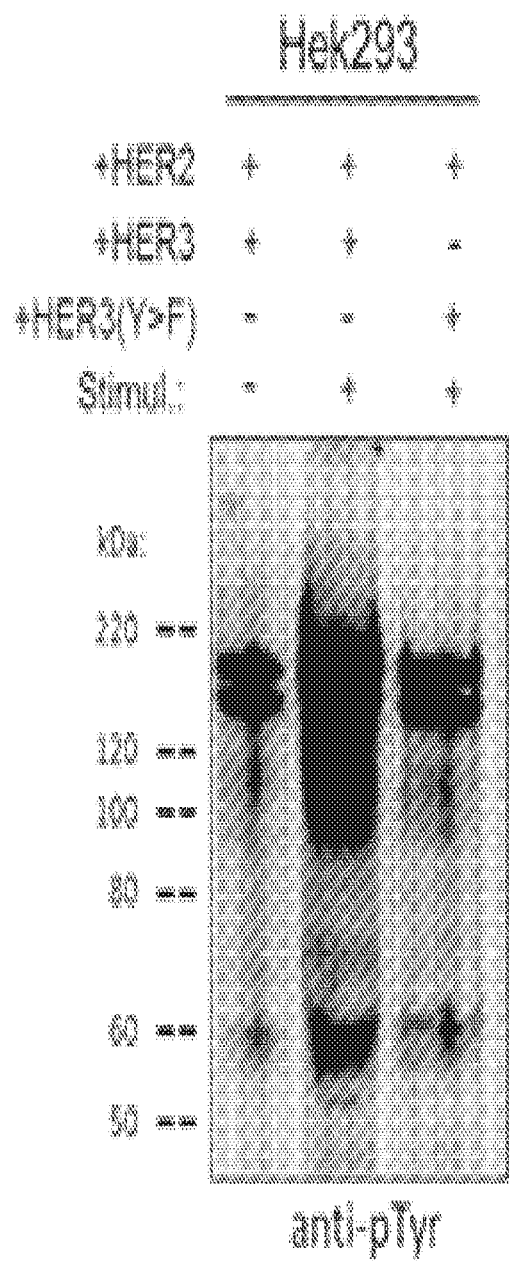
FIG. 20 A presents Western Blotting experiment with lysates of Hek293 cells that were used for the generation of formalin-fixed paraffin-embedded (FFPE) 293 cell pellets. 5 µg total protein of each lysate was subjected to SDS-PAGE and Western Blotting. Detection occurred with an anti-phosphotyrosine antibody (Millipore, clone 4G10).
Figure 20:
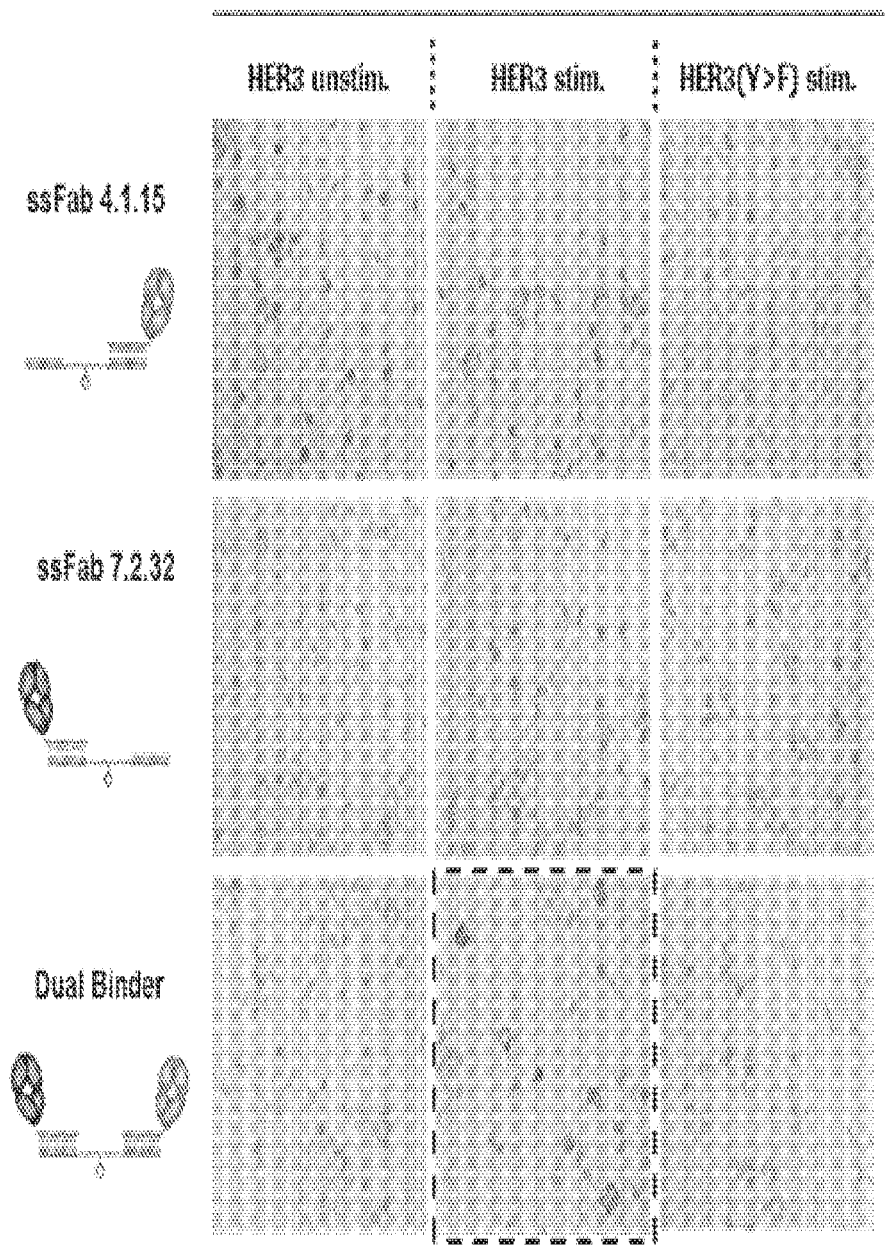

A detection molecule composed of a 4×C18 linker molecule (linker 12 of example 2.4) and only ssFab 7.2.32 or only ssFab 4.1.15 did not produce a staining on any of the tested FFPE cell pellets (FIG. 20 B, rows 1&2). In contrast, detection with the full dual binder molecule (consisting of both ssFab fragments+4×C18 linker) led to a staining—but only on cells that were stimulated with NRG1-β1 and express wild-type HER3 (FIG. 20 B, row 3). No staining was observed on NRG1-β1-stimulated cells that overexpress the mutated version of HER3 lacking the Tyr1289 phosphorylation site. The experiment proves high specificity of the dual binder for phosphorylated HER3.

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure.

This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. A bivalent binding agent capable of binding at least a first epitope and a second epitope of phosphorylated insulin-like growth factor-1 receptor (pIGF-1R) wherein the bivalent binding agent consists of: a first monovalent binder that specifically binds to a polypeptide epitope of SEQ ID NO:11, wherein the first monovalent binder consists of: a Fab'-fragment of mAb 1.4.168 and a first ssDNA of SEQ ID NO:6, the first monovalent binder having a dissociation constant (Kdiss) ranging from $5 \times 10^{-3}$/sec to $1 \times 10^{-4}$/sec; a second monovalent binder that specifically binds to a post-translational polypeptide modification of SEQ ID NO:11 corresponding to phosphorylation of tyrosine residue 1346, wherein the second monovalent binder consists of: a Fab'-fragment selected from the group consisting of mAb 8.1.2 and mAb 30.4.33 and a second ssDNA of SEQ ID NO:5, the second monovalent binder having a Kdiss ranging from $5 \times 10^{-3}$/sec to $1 \times 10^{-4}$/sec; and a linker selected from the group consisting of SEQ ID NO:27, SEQ ID NO:28, and SEQ ID NO:29, linking the first monovalent binder to the second monovalent binder, the bivalent binding agent having a Kdiss of $3 \times 10^{-5}$/sec or less.

2. The bivalent binding agent of claim 1, wherein the linker has a length of 6 to 100 nm.

3. The bivalent binding agent of claim 1, wherein the linker is an L-DNA-linker.

* * * * *

SEQUENCE LISTING

<160> NUMBER OF SEQ ID NOS: 29

<210> SEQ ID NO 1
<211> LENGTH: 122
<212> TYPE: PRT
<213> ORGANISM: Artificial Sequence
<220> FEATURE:
<223> OTHER INFORMATION: Synthetic

<400> SEQUENCE: 1

Gln Cys Asp Val Lys Leu Val Glu Ser Gly Gly Gly Leu Val Lys Pro
1               5                   10                  15

Gly Gly Ser Leu Lys Leu Ser Cys Ala Ala Ser Gly Phe Thr Phe Ser
            20                  25                  30

Asp Tyr Pro Met Ser Trp Val Arg Gln Thr Pro Glu Lys Arg Leu Glu
        35                  40                  45

Trp Val Ala Thr Ile Thr Thr Gly Gly Thr Tyr Thr Tyr Tyr Pro Asp
50                  55                  60

Ser Ile Lys Gly Arg Phe Thr Ile Ser Arg Asp Asn Ala Lys Asn Thr
65                  70                  75                  80

Leu Tyr Leu Gln Met Gly Ser Leu Gln Ser Glu Asp Ala Ala Met Tyr
                85                  90                  95

Tyr Cys Thr Arg Val Lys Thr Asp Leu Trp Trp Gly Leu Ala Tyr Trp
            100                 105                 110

Gly Gln Gly Thr Leu Val Thr Val Ser Ala
        115                 120

<210> SEQ ID NO 2
<211> LENGTH: 116
<212> TYPE: PRT
<213> ORGANISM: Artificial Sequence
<220> FEATURE:
<223> OTHER INFORMATION: Synthetic

<400> SEQUENCE: 2

Gln Leu Val Leu Thr Gln Ser Ser Ser Ala Ser Phe Ser Leu Gly Ala
1               5                   10                  15

Ser Ala Lys Leu Thr Cys Thr Leu Ser Ser Gln His Ser Thr Tyr Thr
            20                  25                  30

Ile Glu Trp Tyr Gln Gln Pro Leu Lys Pro Pro Lys Tyr Val Met
        35                  40                  45

Glu Leu Lys Lys Asp Gly Ser His Thr Thr Gly Asp Gly Ile Pro Asp
50                  55                  60

Arg Phe Ser Gly Ser Ser Ser Gly Ala Asp Arg Tyr Leu Ser Ile Ser
65                  70                  75                  80

Asn Ile Gln Pro Glu Asp Glu Ser Ile Tyr Ile Cys Gly Val Gly Asp
                85                  90                  95

Thr Ile Lys Glu Gln Phe Val Tyr Val Phe Gly Gly Gly Thr Lys Val
            100                 105                 110

Thr Val Leu Gly
        115

<210> SEQ ID NO 3
<211> LENGTH: 121
<212> TYPE: PRT
<213> ORGANISM: Artificial Sequence
<220> FEATURE:
<223> OTHER INFORMATION: Synthetic

<400> SEQUENCE: 3

Glu Val Gln Leu Gln Gln Ser Gly Pro Ala Leu Val Lys Pro Gly Ala
1               5                   10                  15

Ser Val Lys Met Ser Cys Lys Ala Ser Gly Phe Thr Phe Thr Ser Tyr
            20                  25                  30

Val Ile His Trp Val Lys Gln Lys Pro Gly Gln Gly Leu Glu Trp Ile
        35                  40                  45

Gly Tyr Leu Asn Pro Tyr Asn Asp Asn Thr Lys Tyr Asn Glu Lys Phe
    50                  55                  60

Lys Gly Lys Ala Thr Leu Thr Ser Asp Arg Ser Ser Thr Val Tyr
65                  70                  75                  80

Met Glu Phe Ser Ser Leu Thr Ser Glu Asp Ser Ala Val Tyr Phe Cys
                85                  90                  95

Ala Arg Arg Gly Ile Tyr Ala Tyr Asp His Tyr Phe Asp Tyr Trp Gly
            100                 105                 110

Gln Gly Thr Ser Leu Thr Val Ser Ser
        115                 120

<210> SEQ ID NO 4
<211> LENGTH: 106
<212> TYPE: PRT
<213> ORGANISM: Artificial Sequence
<220> FEATURE:
<223> OTHER INFORMATION: Synthetic

<400> SEQUENCE: 4

Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Asn Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Val Thr Ser Tyr Ser Leu Thr Ile Ser Arg Met Glu Ala Glu
65                  70                  75                  80

Asp Ala Ala Thr Tyr Tyr Cys Gln Gln Trp Ser Thr Tyr Pro Leu Thr
                85                  90                  95

Phe Gly Ala Gly Thr Lys Leu Glu Leu Lys
            100                 105

<210> SEQ ID NO 5
<211> LENGTH: 19
<212> TYPE: DNA
<213> ORGANISM: Artificial Sequence
<220> FEATURE:
<223> OTHER INFORMATION: Synthetic

<400> SEQUENCE: 5
agtctattaa tgcttctgc                                         19

<210> SEQ ID NO 6
<211> LENGTH: 17
<212> TYPE: DNA
<213> ORGANISM: Artificial Sequence
<220> FEATURE:
<223> OTHER INFORMATION: Synthetic

<400> SEQUENCE: 6
agttctatcg tcgtcca                                           17

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
gcagaagcat taatagact                                                    19

<210> SEQ ID NO 8
<211> LENGTH: 17
<212> TYPE: DNA
<213> ORGANISM: Artificial Sequence
<220> FEATURE:
<223> OTHER INFORMATION: Synthetic

<400> SEQUENCE: 8
tggacgacga tagaact                                                      17

<210> SEQ ID NO 9
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (16)..(17)
<223> OTHER INFORMATION: bAla

<400> SEQUENCE: 9

Glu Arg Ala Glu Gln Gln Arg Ile Arg Ala Glu Arg Glu Lys Glu Xaa
1               5                   10                  15

Xaa Ser Leu Lys Asp Arg Ile Glu Lys Arg Arg Arg Ala Glu Arg Ala
            20                  25                  30

Glu

<210> SEQ ID NO 10
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (16)..(17)
<223> OTHER INFORMATION: Amino-trioxa-octanoic-acid (Xaa represents
      Amino-trioxa-octanoic-acid)

<400> SEQUENCE: 10

Ser Leu Lys Asp Arg Ile Glu Arg Arg Arg Ala Glu Arg Ala Glu Xaa
1               5                   10                  15

Xaa Glu Arg Ala Glu Gln Gln Arg Ile Arg Ala Glu Arg Glu Lys Glu
            20                  25                  30

<210> SEQ ID NO 11
<211> LENGTH: 27
<212> TYPE: PRT
<213> ORGANISM: Artificial Sequence
<220> FEATURE:
<223> OTHER INFORMATION: Synthetic

<400> SEQUENCE: 11

Phe Asp Glu Arg Gln Pro Tyr Ala His Met Asn Gly Gly Arg Lys Asn

```
                1               5                   10                  15
Glu Arg Ala Leu Pro Leu Pro Gln Ser Ser Thr
            20                  25

<210> SEQ ID NO 12
<211> LENGTH: 28
<212> TYPE: PRT
<213> ORGANISM: Artificial Sequence
<220> FEATURE:
<223> OTHER INFORMATION: Synthetic

<400> SEQUENCE: 12

Tyr Glu Glu His Ile Pro Tyr Thr His Met Asn Gly Gly Lys Lys Asn
1               5                   10                  15

Gly Arg Ile Leu Thr Leu Pro Arg Ser Asn Pro Ser
            20                  25

<210> SEQ ID NO 13
<211> LENGTH: 5
<212> TYPE: PRT
<213> ORGANISM: Artificial Sequence
<220> FEATURE:
<223> OTHER INFORMATION: Synthetic

<400> SEQUENCE: 13

Gly Gly Gly Gly Ser
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Tyr Pro Tyr Asp Val Pro Asp Tyr Ala
1               5

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Gly Leu Asn Asp Ile Phe Glu Ala Gln Lys Ile Glu Trp His Glu
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Leu Pro Glu Thr Gly Gly Gly Ser Gly Ser
1               5                   10

<210> SEQ ID NO 17
<211> LENGTH: 26
<212> TYPE: PRT
<213> ORGANISM: Artificial Sequence
<220> FEATURE:
```

```
<223> OTHER INFORMATION: Synthetic

<400> SEQUENCE: 17

Pro Leu His Pro Val Pro Ile Met Pro Thr Ala Gly Thr Thr Pro Asp
1               5                   10                  15

Glu Asp Tyr Glu Tyr Met Asn Arg Gln Arg
            20                  25

<210> SEQ ID NO 18
<211> LENGTH: 13
<212> TYPE: PRT
<213> ORGANISM: Artificial Sequence
<220> FEATURE:
<223> OTHER INFORMATION: Synthetic

<400> SEQUENCE: 18

Pro Ala Ser Glu Gln Gly Tyr Glu Glu Met Arg Ala Phe
1               5                   10

<210> SEQ ID NO 19
<211> LENGTH: 120
<212> TYPE: PRT
<213> ORGANISM: Artificial Sequence
<220> FEATURE:
<223> OTHER INFORMATION: Synthetic

<400> SEQUENCE: 19

Glu Val Gln Leu Gln Glu Ser Gly Pro Glu Val Ala Lys Pro Gly Ala
1               5                   10                  15

Ser Val Lys Met Ser Cys Lys Ala Ser Gly Tyr Thr Phe Thr Asp Tyr
            20                  25                  30

Ile Ile His Trp Val Lys Gln Arg Pro Gly Gln Asp Leu Glu Trp Ile
        35                  40                  45

Gly Tyr Ile Asn Pro Tyr Asn Asp Lys Ser Lys Tyr Asn Glu Lys Phe
    50                  55                  60

Lys Asp Lys Ala Thr Leu Thr Ser Asp Arg Ser Ser Thr Ser Thr Tyr
65                  70                  75                  80

Met Asp Leu Ser Thr Leu Thr Ser Asp Asp Ser Ala Val Tyr Tyr Cys
                85                  90                  95

Thr Arg His Gly Tyr Tyr Arg Ser Asp Gly Phe Asp Tyr Trp Gly Gln
            100                 105                 110

Gly Thr Thr Leu Thr Val Ser Ser
        115                 120

<210> SEQ ID NO 20
<211> LENGTH: 108
<212> TYPE: PRT
<213> ORGANISM: Artificial Sequence
<220> FEATURE:
<223> OTHER INFORMATION: Synthetic

<400> SEQUENCE: 20

Asp Ile Val Leu Thr Gln Ser Pro Thr Ile Met Ser Ala Ser Pro Gly
1               5                   10                  15

Glu Lys Val Thr Met Thr Cys Arg Ala Ser Ser Ser Val Ser Ser Ser
            20                  25                  30

Ser Leu His Trp Tyr Gln Gln Lys Pro Gly Ser Ser Pro Lys Leu Trp
        35                  40                  45

Ile Tyr Ser Thr Ser Thr Leu Ala Ser Gly Val Pro Ala Arg Phe Ser
    50                  55                  60
```

Gly Ser Gly Ser Gly Thr Ser Tyr Ser Leu Thr Ile Ser Gly Val Glu
65                  70                  75                  80

Thr Glu Asp Ala Ala Thr Tyr Tyr Cys Gln Gln Tyr Gly Thr Ser Pro
                85                  90                  95

Tyr Thr Phe Gly Ser Gly Thr Lys Val Asp Ile Lys
            100                 105

<210> SEQ ID NO 21
<211> LENGTH: 120
<212> TYPE: PRT
<213> ORGANISM: Artificial Sequence
<220> FEATURE:
<223> OTHER INFORMATION: Synthetic

<400> SEQUENCE: 21

Glu Phe Glu Val Gln Leu Gln Glu Ser Gly Gly Leu Val Gln Pro
1               5                   10                  15

Lys Gly Ser Leu Gln Leu Ser Cys Ala Ala Ser Gly Phe Thr Phe Asn
                20                  25                  30

Thr Tyr Ala Met His Trp Val Arg Gln Ala Pro Gly Lys Gly Leu Glu
                35                  40                  45

Trp Val Ala Arg Ile Arg Thr Glu Ser Ser Asp Tyr Ala Thr Asp Tyr
50                  55                  60

Ala Asp Ser Val Lys Asp Arg Phe Ile Ile Ser Arg Asp Asp Ser Gln
65                  70                  75                  80

Asn Met Leu Tyr Leu Gln Met Asn Asn Leu Lys Ser Glu Asp Thr Ala
                85                  90                  95

Ile Tyr Tyr Cys Val Arg Ser Ser Gly Phe Asp Tyr Trp Gly Gln Gly
                100                 105                 110

Thr Thr Leu Thr Val Ser Ser Ser
            115                 120

<210> SEQ ID NO 22
<211> LENGTH: 110
<212> TYPE: PRT
<213> ORGANISM: Artificial Sequence
<220> FEATURE:
<223> OTHER INFORMATION: Synthetic

<400> SEQUENCE: 22

Asp Ile Gln Met Thr Gln Ser Pro Ser Leu Pro Val Ser Leu Gly Asp
1               5                   10                  15

Gln Ala Ser Ile Ser Cys Arg Ser Ser Gln Ser Leu Val His Asp Asn
                20                  25                  30

Gly Asn Thr Tyr Leu His Trp Phe Leu Gln Lys Pro Gly Gln Ser Pro
            35                  40                  45

Lys Leu Leu Ile Tyr Lys Val Ser Asn Arg Phe Ser Gly Val Pro Asp
50                  55                  60

Arg Phe Gly Gly Ser Gly Ser Gly Thr Asp Phe Thr Leu Lys Ile Ser
65                  70                  75                  80

Gly Val Glu Ala Glu Asp Leu Gly Val Tyr Phe Cys Ser Gln Gly Thr
                85                  90                  95

His Val Pro Thr Phe Gly Gly Gly Thr Lys Leu Glu Ile Lys
            100                 105                 110

<210> SEQ ID NO 23
<211> LENGTH: 123
<212> TYPE: PRT
<213> ORGANISM: Artificial Sequence

```
<220> FEATURE:
<223> OTHER INFORMATION: Synthetic

<400> SEQUENCE: 23
```

| Glu | Phe | Glu | Val | Gln | Leu | Gln | Glu | Ser | Gly | Pro | Glu | Leu | Val | Lys | Pro |
|---|---|---|---|---|---|---|---|---|---|---|---|---|---|---|---|
| 1 | | | | 5 | | | | | 10 | | | | | 15 | |

| Gly | Thr | Ser | Val | Thr | Ile | Ser | Cys | Lys | Thr | Ser | Gly | Tyr | Ala | Phe | Ser |
|---|---|---|---|---|---|---|---|---|---|---|---|---|---|---|---|
| | | | 20 | | | | | 25 | | | | | 30 | | |

| Asn | Ser | Trp | Met | Ser | Trp | Val | Lys | Gln | Arg | Pro | Gly | Gln | Gly | Leu | Glu |
|---|---|---|---|---|---|---|---|---|---|---|---|---|---|---|---|
| | | | | 35 | | | | | 40 | | | | | 45 | |

| Trp | Ile | Gly | Arg | Ile | Phe | Pro | Gly | Asn | Gly | Asp | Thr | Asp | Tyr | Asn | Gly |
|---|---|---|---|---|---|---|---|---|---|---|---|---|---|---|---|
| | 50 | | | | | 55 | | | | | 60 | | | | |

| Asn | Phe | Arg | Ala | Lys | Ala | Thr | Leu | Thr | Ala | Asp | Lys | Ser | Ser | Ser | Thr |
|---|---|---|---|---|---|---|---|---|---|---|---|---|---|---|---|
| 65 | | | | | 70 | | | | | 75 | | | | | 80 |

| Ala | Phe | Met | Gln | Leu | Ser | Arg | Leu | Thr | Ser | Val | Asp | Ser | Ala | Val | Tyr |
|---|---|---|---|---|---|---|---|---|---|---|---|---|---|---|---|
| | | | | 85 | | | | | 90 | | | | | 95 | |

| Phe | Cys | Ala | Arg | Ser | Arg | Gly | Leu | Arg | Gln | Gly | Ala | Gly | Phe | Ala | Tyr |
|---|---|---|---|---|---|---|---|---|---|---|---|---|---|---|---|
| | | | 100 | | | | | 105 | | | | | 110 | | |

| Trp | Gly | Gln | Gly | Thr | Leu | Val | Thr | Val | Ser | Ala |
|---|---|---|---|---|---|---|---|---|---|---|
| | | | 115 | | | | | 120 | | |

```
<210> SEQ ID NO 24
<211> LENGTH: 113
<212> TYPE: PRT
<213> ORGANISM: Artificial Sequence
<220> FEATURE:
<223> OTHER INFORMATION: Synthetic

<400> SEQUENCE: 24
```

| Asp | Ile | Val | Met | Thr | Gln | Ser | Pro | Ser | Ser | Leu | Ala | Met | Ser | Val | Gly |
|---|---|---|---|---|---|---|---|---|---|---|---|---|---|---|---|
| 1 | | | | 5 | | | | | 10 | | | | | 15 | |

| Gln | Lys | Ala | Thr | Met | Ser | Cys | Lys | Ser | Ser | Gln | Ser | Leu | Leu | Asn | Ser |
|---|---|---|---|---|---|---|---|---|---|---|---|---|---|---|---|
| | | | 20 | | | | | 25 | | | | | 30 | | |

| Ser | Thr | Gln | Arg | Asn | Tyr | Leu | Ala | Trp | Tyr | Gln | Gln | Lys | Pro | Gly | Gln |
|---|---|---|---|---|---|---|---|---|---|---|---|---|---|---|---|
| | | | | 35 | | | | | 40 | | | | | 45 | |

| Ser | Pro | Lys | Leu | Leu | Val | Tyr | Phe | Ala | Ser | Thr | Arg | Glu | Ser | Gly | Val |
|---|---|---|---|---|---|---|---|---|---|---|---|---|---|---|---|
| | 50 | | | | | 55 | | | | | 60 | | | | |

| Pro | Asp | Arg | Phe | Ile | Gly | Ser | Gly | Ser | Gly | Thr | Asp | Phe | Thr | Leu | Thr |
|---|---|---|---|---|---|---|---|---|---|---|---|---|---|---|---|
| 65 | | | | | 70 | | | | | 75 | | | | | 80 |

| Ile | Ser | Ser | Val | Gln | Ala | Glu | Asp | Leu | Ala | Ala | Tyr | Phe | Cys | Gln | Gln |
|---|---|---|---|---|---|---|---|---|---|---|---|---|---|---|---|
| | | | | 85 | | | | | 90 | | | | | 95 | |

| His | Tyr | Ser | Asn | Pro | Arg | Thr | Phe | Gly | Gly | Gly | Thr | Lys | Leu | Glu | Ile |
|---|---|---|---|---|---|---|---|---|---|---|---|---|---|---|---|
| | | | 100 | | | | | 105 | | | | | 110 | | |

Lys

```
<210> SEQ ID NO 25
<211> LENGTH: 17
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Gly-Gly-Aminolinker-(Spacer C3)3
<220> FEATURE:
<221> NAME/KEY: misc_feature
<222> LOCATION: (17)..(17)
<223> OTHER INFORMATION: 'A' is fluorescein labeled

<400> SEQUENCE: 25
```
agttctatcg tcgtcca                                                17

<210> SEQ ID NO 26
<211> LENGTH: 19
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 'A' is fluorescein labeled
<220> FEATURE:
<221> NAME/KEY: misc_feature
<222> LOCATION: (19)..(19)
<223> OTHER INFORMATION: (Spacer C3)3-Aminolinker-Gly-Gly

<400> SEQUENCE: 26
agtctattaa tgcttctgc                                              19

<210> SEQ ID NO 27
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(20)
<223> OTHER INFORMATION: Biotin-dT (=T-Bi)
      (5'-Dimethoxytrityloxy-5-[N-((4-t-butylbenzoyl)-biotinyl)-aminohe
      xyl)-3-acrylimido]-2'-deoxyUridine-3'-[(2-cyanoethyl)-(N,N-diisop
      ropyl)]-phosphoramidite

<400> SEQUENCE: 27
gcagaagcat taatagactt tggacgacga tagaact                          37

<210> SEQ ID NO 28
<211> LENGTH: 47
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(25)
<223> OTHER INFORMATION: Biotin-dT (=T-Bi)
      (5'-Dimethoxytrityloxy-5-[N-((4-t-butylbenzoyl)-biotinyl)-aminohe
      xyl)-3-acrylimido]-2'-deoxyUridine-3'-[(2-cyanoethyl)-(N,N-diisop
      ropyl)]-phosphoramidite

<400> SEQUENCE: 28
gcagaagcat taatagactt tttttttttt tggacgacga tagaact                47

<210> SEQ ID NO 29
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (35)..(35)
<223> OTHER INFORMATION: Biotin-dT (=T-Bi)
      (5'-Dimethoxytrityloxy-5-[N-((4-t-butylbenzoyl)-biotinyl)-aminohe
      xyl)-3-acrylimido]-2'-deoxyUridine-3'-[(2-cyanoethyl)-(N,N-diisop
      ropyl)]-phosphoramiditee

```
<400> SEQUENCE: 29
gcagaagcat taatagactt ttttttttt ttttttttt ttttttttt tggacgacga        60 tagaact                                                              67
```